United States Patent
Storkus et al.

(10) Patent No.: US 9,345,770 B2
(45) Date of Patent: May 24, 2016

(54) IMMUNOGENIC TUMOR ASSOCIATED STROMAL CELL ANTIGEN PEPTIDES AND METHODS OF THEIR USE

(71) Applicant: University of Pittsburgh—Of the Commonwealth System of Higher Education, Pittsburgh, PA (US)

(72) Inventors: Walter J. Storkus, Pittsburgh, PA (US); Anamika Bose, Kolkata (IN); Jennifer Lynn Taylor, McDonald, PA (US); Xi Zhao, Pittsburgh, PA (US); Devin B. Lowe, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/358,705

(22) PCT Filed: Nov. 15, 2012

(86) PCT No.: PCT/US2012/065327
§ 371 (c)(1),
(2) Date: May 15, 2014

(87) PCT Pub. No.: WO2013/074820
PCT Pub. Date: May 23, 2013

(65) Prior Publication Data
US 2014/0314758 A1    Oct. 23, 2014

Related U.S. Application Data

(60) Provisional application No. 61/560,597, filed on Nov. 16, 2011.

(51) Int. Cl.
| | | |
|---|---|---|
| A61K 45/06 | (2006.01) | |
| A61K 38/08 | (2006.01) | |
| A61K 38/17 | (2006.01) | |
| G01N 33/574 | (2006.01) | |
| A61K 39/00 | (2006.01) | |
| A61K 31/506 | (2006.01) | |

(52) U.S. Cl.
CPC .............. *A61K 45/06* (2013.01); *A61K 31/506* (2013.01); *A61K 38/08* (2013.01); *A61K 38/1709* (2013.01); *A61K 39/0011* (2013.01); *G01N 33/574* (2013.01); *G01N 33/5743* (2013.01); *G01N 33/57438* (2013.01); *G01N 33/57446* (2013.01); *A61K 2039/5154* (2013.01); *A61K 2039/5158* (2013.01); *A61K 2039/5256* (2013.01); *A61K 2039/53* (2013.01); *A61K 2039/55538* (2013.01)

(58) Field of Classification Search
None
See application file for complete search history.

(56) References Cited

U.S. PATENT DOCUMENTS

| | | |
|---|---|---|
| 7,981,424 B2 | 7/2011 | Mjalli et al. |
| 2009/0299038 A1 | 12/2009 | Nakamura et al. |

FOREIGN PATENT DOCUMENTS

| | | | |
|---|---|---|---|
| AU | 2003218603 B2 | | 10/2003 |
| AU | 2007318483 A1 | | 5/2008 |
| WO | WO9955865 | * | 11/1999 |
| WO | WO 03/075921 A2 | | 9/2003 |
| WO | WO03086450 | * | 10/2003 |

OTHER PUBLICATIONS

Zhao et al, Molecular therapy 19:805-814, Apr. 2011.*
Gonzalez et al, Eur J Immunol 45:2615-27, 2015.*
International Search Report from parent PCT Application No. PCT/US2012/065327, 7 pages (mailed Dec. 19, 2012).
Written Opinion from parent PCT Application No. PCT/US2012/065327, 6 pages. (mailed Dec. 19, 2012).
Yan et al., "RAGE and amyloid-beta peptide neurotoxicity in Alzheimer's disease," *Nature* 22;382(6593):685-691 (1996) (Abstract only).
Zhao et al., "Intratumoral IL-12 Gene Therapy Results in the Crosspriming of Tc1 Cells Reactive Against Tumor-associated Stromal Antigens," *Mol Ther.* 19(4):805-814 (2011).

\* cited by examiner

*Primary Examiner* — Lei Yao
(74) *Attorney, Agent, or Firm* — Klarquist Sparkman, LLP

(57) ABSTRACT

Immunogenic peptides from tumor associated stromal cell antigens, including combinations of such peptides, are disclosed herein. In some examples the peptides are useful for methods of eliciting an immune response. In additional examples the peptides are useful for methods of treating cancer. Methods for decreasing vascularization of a tumor using a Protein Delta Homolog 1 (DLK1) protein or a nucleic acid encoding the protein are also disclosed.

17 Claims, 27 Drawing Sheets

FIG. 8A FIG. 8B FIG. 8C

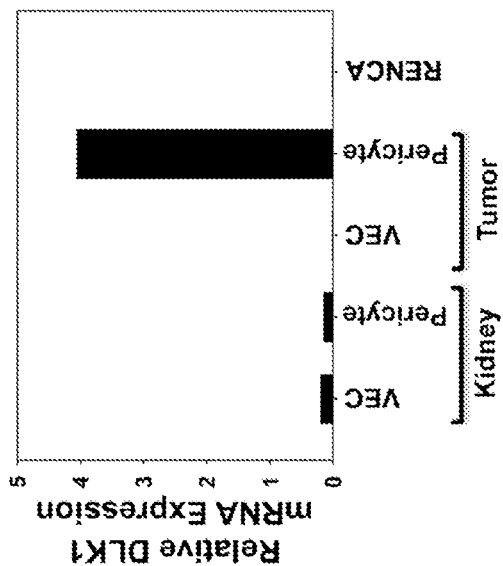
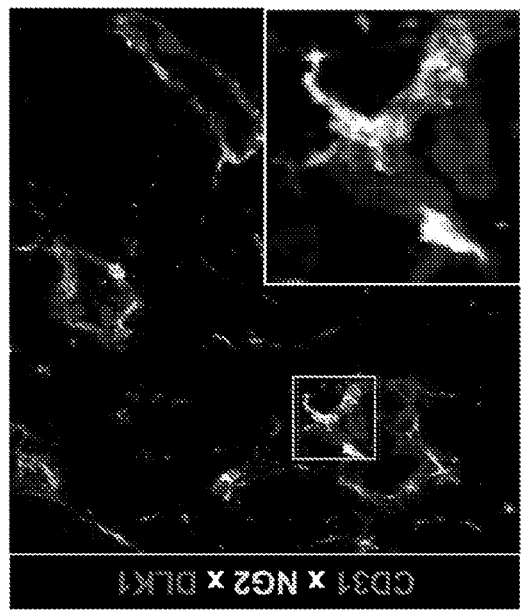
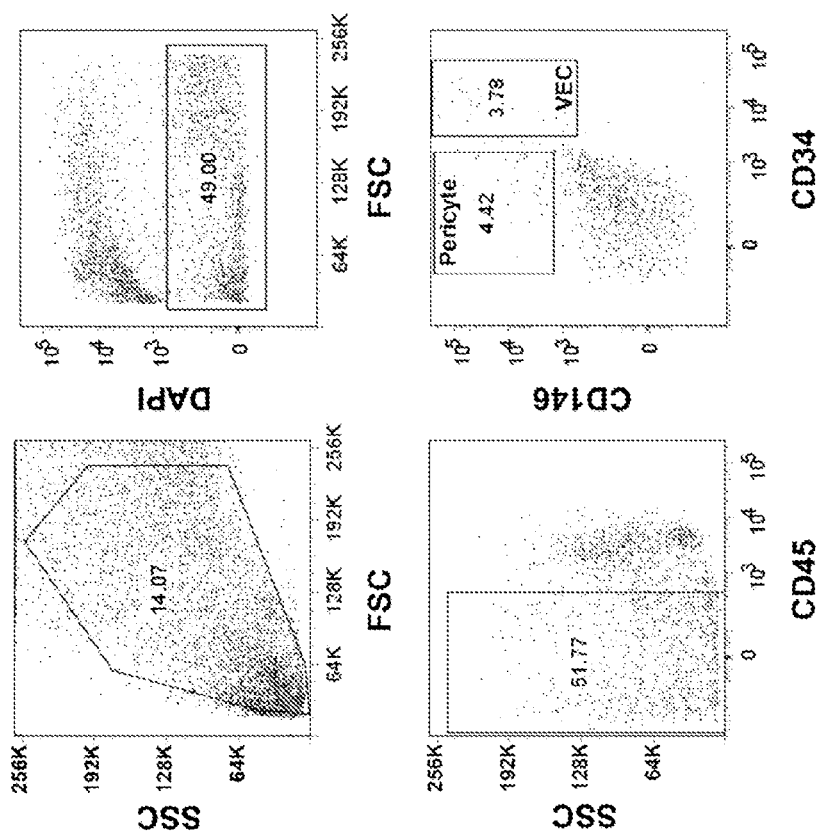

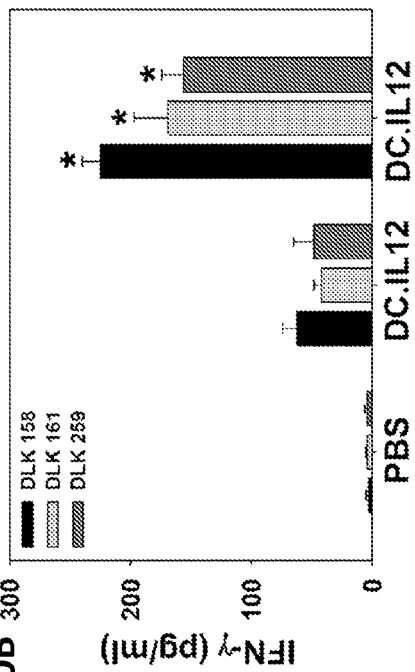
FIG. 20A
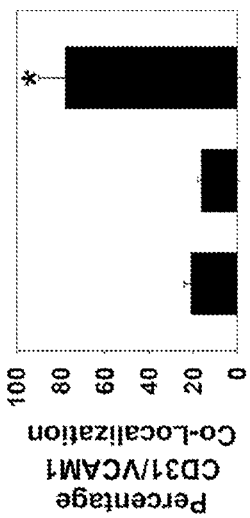
FIG. 20B
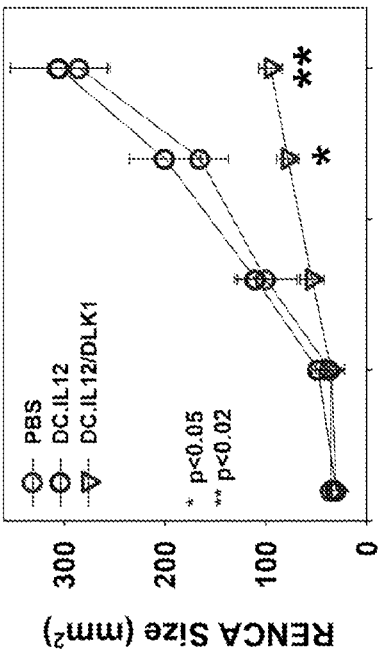
FIG. 20C
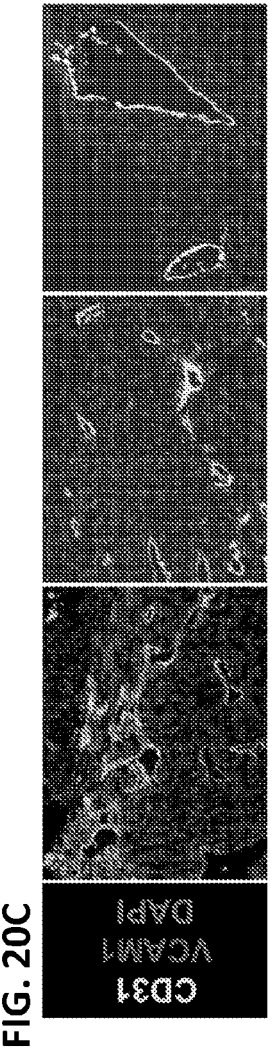
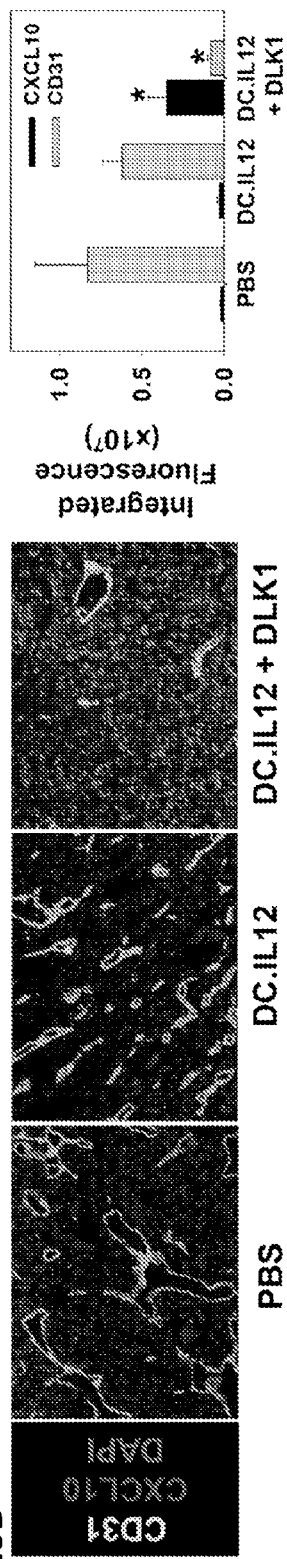
FIG. 20D

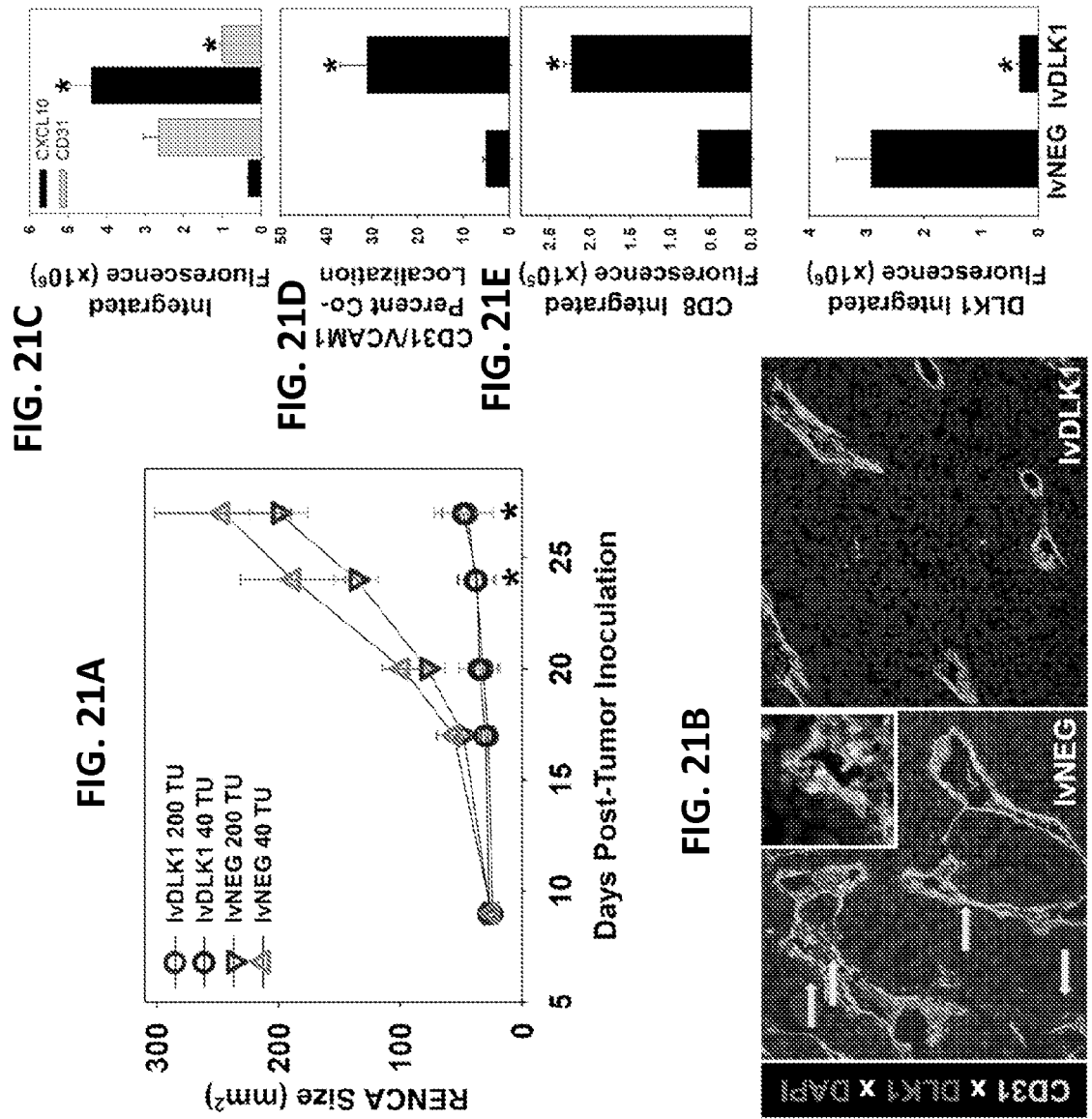

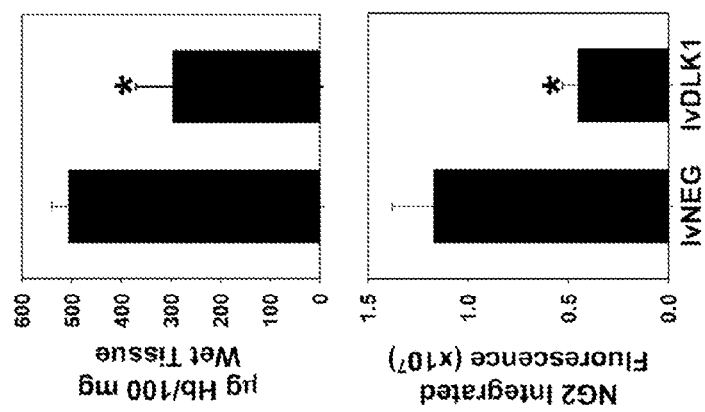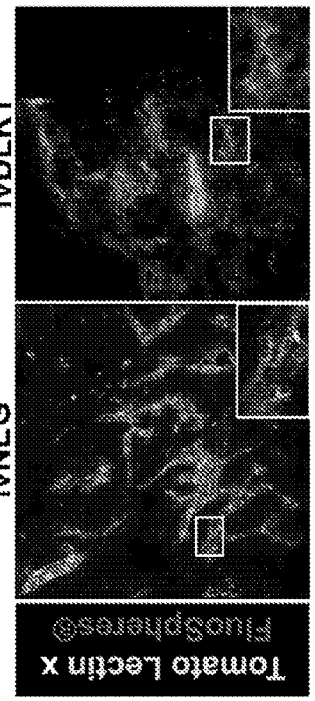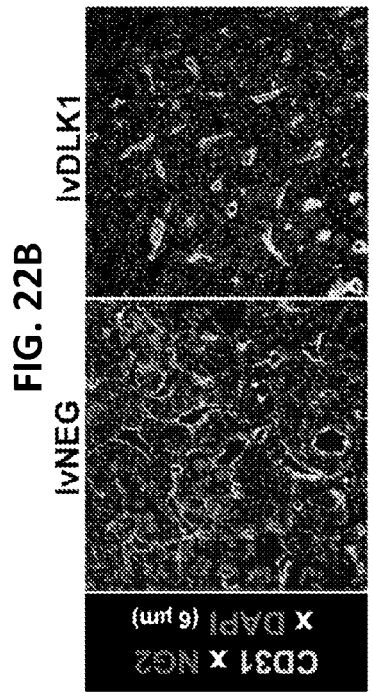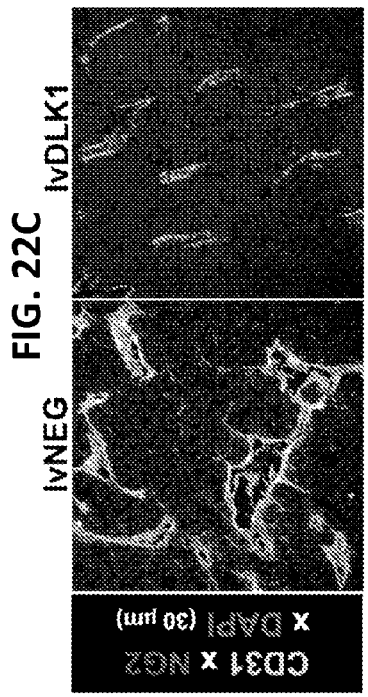

FIG. 23A
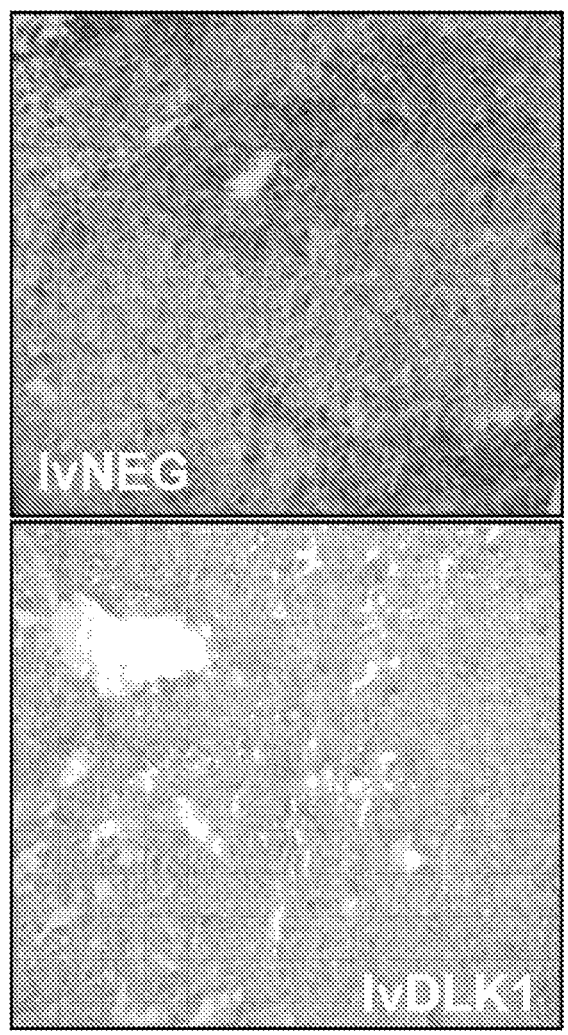
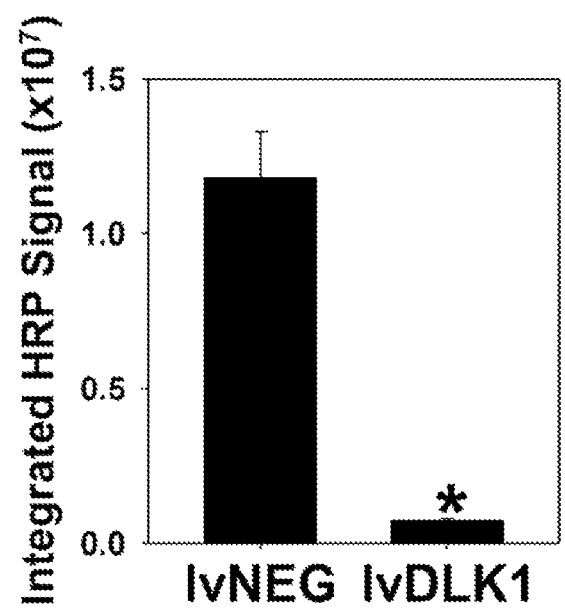

IMMUNOGENIC TUMOR ASSOCIATED STROMAL CELL ANTIGEN PEPTIDES AND METHODS OF THEIR USE

This is the U.S. National Stage of International Application No. PCT/US2012/065327, filed Nov. 15, 2012, which was published in English under PCT Article 21(2), which in turn claims the benefit of U.S. Provisional Application No. 61/560,597, filed on Nov. 16, 2011, which is incorporated by reference herein in its entirety.

ACKNOWLEDGMENT OF GOVERNMENT SUPPORT

This invention was made with government support under Grant Nos. R01 NIH CA114071, R01 NIH CA140375 and P50 NIH CA121973 awarded by the National Institutes of Health. The government has certain rights in the invention.

FIELD

This application relates to the field of cancer therapeutics, specifically to molecules such as immunogenic peptides, proteins, and inhibitory nucleic acids for the treatment of cancer.

BACKGROUND

T cell-mediated anti-tumor immunity plays a role in regulating tumor growth, placing selective pressure on the antigenically-heterogeneous cancer cell population throughout disease progression (Ostrand-Rosenberg, Curr. Opin. Genet. Dev., 18: 11-18. 2008; Reiman et al., Semin. Cancer Biol., 17: 275-287, 2007; Bui and Schreiber, Curr. Opin. Immunol., 19: 203-208, 2007). Most tumor-associated antigens (TAAs) recognized by T cells are "self" antigens that may be quantitatively over-expressed by tumor cells of one or more histologic types (Slingluff et al., Adv. Immunol., 90: 243-2952006). Clinical trials implementing vaccines and immunotherapies targeting such antigens have exhibited success in promoting increased numbers of specific $CD4^+$ and/or $CD8^+$ T cell populations in the peripheral blood of patients. There is a need to identify additional tumor associated antigens or combinations of antigens that can be used for cancer immunotherapy.

SUMMARY

Immunogenic tumor associated stromal cell antigen (TASA) peptides are disclosed herein. In some embodiments a plurality of immunogenic TASA peptides is included in a composition. In some embodiments, the immunogenic TASA peptides include at most twelve amino acids from a TASA, such as Protein Delta Homolog 1 (DLK1), Hemoglobin Subunit Beta (HBB), Neuropilin 1 (NRP1), Tumor Endothelial Marker 1 (TEM1), Ephrin Type A Receptor 2 (EphA2), Regulator of G-Protein Signaling 5 (RGS5), or Platelet Derived Growth Factor Receptor β (PDGFRβ). In some embodiments, compositions are provided including combinations of these polypeptides. In one non-limiting example, a composition is disclosed including DLK1, HBB, NRP1, and TEM1 peptides. In another non-limiting example, a composition is disclosed including DLK1, HBB, NRP1, TEM1, EphA1 and RGS5 peptides.

In additional embodiments, polynucleotides encoding the immunogenic TASA peptides, vectors including these polynucleotides, host cells transformed with these vectors, and methods of using these peptides, polynucleotides, vectors, and host cells are provided.

In further embodiments, the immunogenic TASA peptides, polynucleotides, vectors and host cells can be used, for example, for inducing an immune response to one or more TASA or to treat or inhibit cancer.

In additional embodiments, methods are disclosed for treating a tumor, such as by decreasing vascularization of a tumor. The methods include administering to a subject having a tumor an effective amount of a Protein Delta Homolog 1 (DLK1) protein, a nucleic acid encoding the DLK1 protein, or a dendritic cell transformed with the nucleic acid. In some non-limiting examples, the methods also include administering to the subject a therapeutically effective amount of bevacizumab, sunitinib, axitinib, an HSP90 inhibitor, or gencitabine/fludarabine. In additional non-limiting examples, the tumor is a melanoma, hepatocellular carcinoma or colorectal cancer.

BRIEF DESCRIPTION OF THE FIGURES

In FIG. 1A, B16 melanoma cells were injected subcutaneously (s.c.) in the right flank of female HHD mice and allowed to establish/progress for 14 days. Animals were then euthanized, with tumors resected, fixed, sectioned and analyzed for expression of the indicated antigens using specific Abs and fluorescence microscopy. Specific antibody against NG2 (green), the indicated antigen of interest (red), and CD31 (blue) were used to distinguish preferential antigen expression in tumor-associated stromal pericytes, vascular endothelial cells (VEC), alternate stromal cells and/or tumor cells. In FIG. 1B, B16 melanoma cells, as well as, flow-sorted (PDGFRβ$^+$, CD31$^{neg}$) pericytes and (PDGFRβ$^{neg}$, CD31$^+$) VEC isolated from day 19 established B16 tumors and tumor-uninvolved kidneys were analyzed for expression of target gene product mRNAs using RT-PCR. All data are reflective of three independent experiments performed for each tumor type.

In FIG. 2A, HLA-A2$^{neg}$ B16 melanoma cells were injected subcutaneously in the right flank of female HLA-A2 Tg (HHD) mice and allowed to establish for seven days. On day seven, mice were randomized into three groups (n=5 mice each) receiving no treatment, intratumoral (i.t.) injection of syngenic dendritic cells (DC) that were previously infected with recombinant adenovirus encoding mIL-12p70, or DC infected with control (empty) adenovirus (i.e. DC.ψ5). Animals were retreated using the same therapy on day 14 post-tumor inoculation. In replicate cohorts of animals receiving DC.IL12 therapy, depleting antibodies against CD4 or CD8 were provided beginning on day 6 post-tumor inoculation. Tumor sizes were assessed every 3-4 days and are reported as mean+/−SD in mm$^2$. *p<0.05 versus control or DC.ψ5-treated mice on days ≥14. In FIG. 2B., on day 19 post-tumor inoculation, the mice were euthanized and CD8$^+$ splenocytes isolated by magnetic bead cell sorting (MACS) and cultured with PDGFRβ$^+$CD31$^{neg}$H-2K$^{b(neg)}$ pericytes or PDGFRβ$^{neg}$CD31$^+$H-2K$^{b(neg)}$ VEC sorted by flow cytometry. After co-culture in the absence or presence of anti-HLA-A2 mAb BB7.2 or anti-MHC class II mAb L243 (10 μg/well) for 48 h at 37° C., cell-free supernatants were analyzed for mIFN-γ content by specific ELISA. Data are mean+/−SD for triplicate determinations, and are representative of 2 independent experiments performed. *p<0.05 versus kidney cells (pericytes or VEC) and tumor pericytes/VEC in the presence of anti-HLA-A2 mAb BB7.2. In FIG. 2C, on day 19 post-tumor inoculation, the mice were euthanized and splenocytes and stimulated for five days with stromal peptides. On day five, MACS-isolated $CD8^+$ splenocytes were cocultured with $HLA-A2^+$ T2 cells loaded with the indicated TASA-derived peptides or HLA-$A2^{neg}$ B16 tumor cells. After a 48 h culture period, cell-free supernatants were analyzed for mIFN-γ concentration by specific ELISA. Data are mean+/−SD for triplicate ELISA determinations. *p<0.05 versus FluM1 control peptide responses. All presented data are representative of 3 independent experiments performed.

FIGS. 8A-8C shows a series of graphs illustrating that $CD8^+$ TIL isolated from B16-bearing HHD mice treated with DC.IL12 recognize tumor-associated pericytes in an HLA-A2-restricted manner, and fail to recognize HLA-$A2^{neg}$ B16 tumor cells. TIL were isolated from the day 17 melanomas of mice (treated as indicated) and analyzed for reactivity against flow-sorted tumor pericytes as described in FIG. 3 for intracellular IFN-γ or cell surface expression of translocated CD107 using flow cytometry. To assess MHC-restriction in T cell recognition of tumor pericytes, 10 μg of anti-HLA-A2 mAb BB7.2 or anti-pan class II mAb L243 were added to cultures during the 4-5 hours co-incubation period prior to flow cytometry-based analysis. Inset numbers reflect the percentage of $CD8^+$ T cells exhibiting positive response to tumor pericytes or B16 melanoma cells. Data derive from one representative experiment of two independent experiments performed.

In FIG. 9A, HHD mice (five animals/cohort) were vaccinated twice (d-14, d-7) subcutaneously with PBS or with isologous DC.IL12 pulsed with PBS or synthetic peptides (Table 6) derived from the indicated TASA. In cases where more than 1 peptide was identified for a given target antigen, an equimolar pool of the indicated peptides (each 10 μM) was pulsed onto DC.IL12 and used for vaccination in the relevant cohort. One week after the second immunization, spleens were harvested and splenic $CD8^+$ T cells isolated using MACS-beads (Miltenyi). T cells were stimulated in vitro for 48 h using the $HLA-A2^+$ T2 cell line pulsed with relevant TASA vs. irrelevant HIV-$nef_{190-198}$ (AFHHVAREL; ref. 24) peptides. Cell-free supernatants were then recovered and IFN-γ levels by ELISA. Data are reported as mean+/−SD for triplicate ELISA determinations, and are representative of 3 independent experiments performed. *p<0.05 vs. HIV-nef control peptide responses. In FIG. 9B, HHD mice were vaccinated twice (days-14 and -7; right flank) subcutaneously with PBS or with isologous DC.IL12 pulsed with PBS or synthetic TASA peptides as indicated in FIG. 1A. In cases where more than 1 peptide is identified for a given target antigen, an equimolar pool of the indicated peptides (each 10 μM) was pulsed onto DC.IL12 and used for vaccination in the relevant cohort. One week after the booster vaccine (i.e. day zero), animals were challenged subcutaneously on their left flank with $2 \times 10^6$ MC38 colon carcinoma cells. Tumor growth was then monitored every 3-4 days through day 24. All data represent mean tumor area (in $mm^2$)+/−SD determined from 5 mice/cohort, and are representative of three independent experiments performed. *$p<0.05$ versus DC only on the indicated days.

In FIG. 10A., six-micron tissue sections were co-stained with anti-CD8 (green) and anti-NG2 (red) antibodies and imaged by fluorescence microscopy. Blue signal=nuclear counterstain using 4',6-diamidino-2-phenylindole (DAPI). FIG. 10B provides a summary of the mean+/−SD number of $CD8^+$ cells per high-power field (HPF) in MC38 tumors isolated from control or vaccinated mice as depicted in FIG. 10A. In FIG. 10C, tissue sections were co-stained with anti-CD31 (green) and anti-NG2 (red) antibodies and imaged by fluorescence microscopy. Blue signal=nuclear counterstain using DAPI. In FIG. 10D, the mean+/−SD number of $CD31^+$ vessels per HPF of MC38 tumors in control or vaccinated mice are summarized. Representative data is depicted from 1 of 3 independent experiments performed. *$p<0.05$ versus DC only or untreated control mice.

In FIG. 11A, HHD mice bearing established day seven subcutaneous MC38 tumors (right flank) were left untreated, or they were vaccinated in the left flank with control DC.IL12 or DC.IL12 pulsed with an equimolar pool (10 μM each) of the following TASA-derived peptides: $DLK1_{326-334}$, $EphA2_{883-891}$, $HBB_{31-39}$, $NRP1_{869-877}$, $FDG$-$FR\beta_{890-898}$, $RGS5_{5-13}$ and $TEM1_{691-700}$. Identical booster vaccines were provided on day 14 post-tumor inoculation. As indicated, two vaccine cohorts were treated with depleting anti-CD4 or anti-CD8 monoclonal antibodies to evaluate the impact of these T cell subsets on therapy outcome. Tumor growth was monitored every 3-4 days through d28. In FIG. 11B, Female HHD or C57BL/6 (B6) mice were inoculated subcutaneously in the right flank with $1 \times 10^5$ B16 (HLA-$A2^{neg}$) tumor cells. After 7 days, animals were randomized into groups of 5 mice exhibiting tumor lesions with a mean surface area of 60-75 $mm^2$. The mice then received vaccines consisting of isologous control or peptide-pulsed DC.IL12 cells subcutaneously in the left flank on days 10 and 17 (post-tumor inoculation). In cases where more than one peptide was identified for a given target antigen, an equimolar pool of the indicated peptides (each 10 μM) was pulsed onto DC.IL12 and used for vaccination. Tumor size (mean+/−SD) was monitored every 3-4 days through day 34. In FIG. 11A and FIG. 11B, mean tumor area+/−SD is reported for 5 animals/cohort. Data are the representative of those obtained in two independent experiments in each case. *$p<0.05$ versus DC only on the indicated days. In FIG. 11C, HHD mice bearing subcutaneous B16 melanomas were treated as described in FIG. 11B and followed through day 60 post-tumor inoculation. Data are reported in a Kaplan-Meier plot depicting overall percentage of surviving animals over time. *$p<0.02$ versus DC only; ** $p<0.002$ versus DC only (with refined p-values for differences between treatment cohorts reported in Table 6). Data are cumulative for three independent experiments performed.

Individual data included: CD8+ TIL (day 7 post tumor-inoculation (in mean numbers per HPF), CD31+ vessels in these same lesions (reported a mean number/10 HPF), tumor size (in mm2) on day 24 post-tumor inoculation, and specific production of IFN-γ from splenic CD8+ T cells harvested from control and vaccinated mice on day 14 post-tumor inoculation. Each dot represents a control (DC only) or vaccine cohort evaluated (n=10). For panels including in vitro T cell response data, each symbol reflects cumulative response against a given target antigen (i.e. for DLK1, this represents the summation of responses against each of three peptides, while for RGS5, this reflects response against a single peptide). Note that in all instances, except for the IFN-γ×Tumor Size comparison (n=13), the cohorts vaccinated using DLK1-, NRP1- or PDGFRβ-derived peptides are not included in the indicated analysis, as these mice failed to develop lesions capable of being resected for analyses. Linear regression lines are inserted in each panel, with the associated $r^2$ values reported in each instance. Lines indicating 95% confidence intervals are also provided in each panel.

Figure 17A:
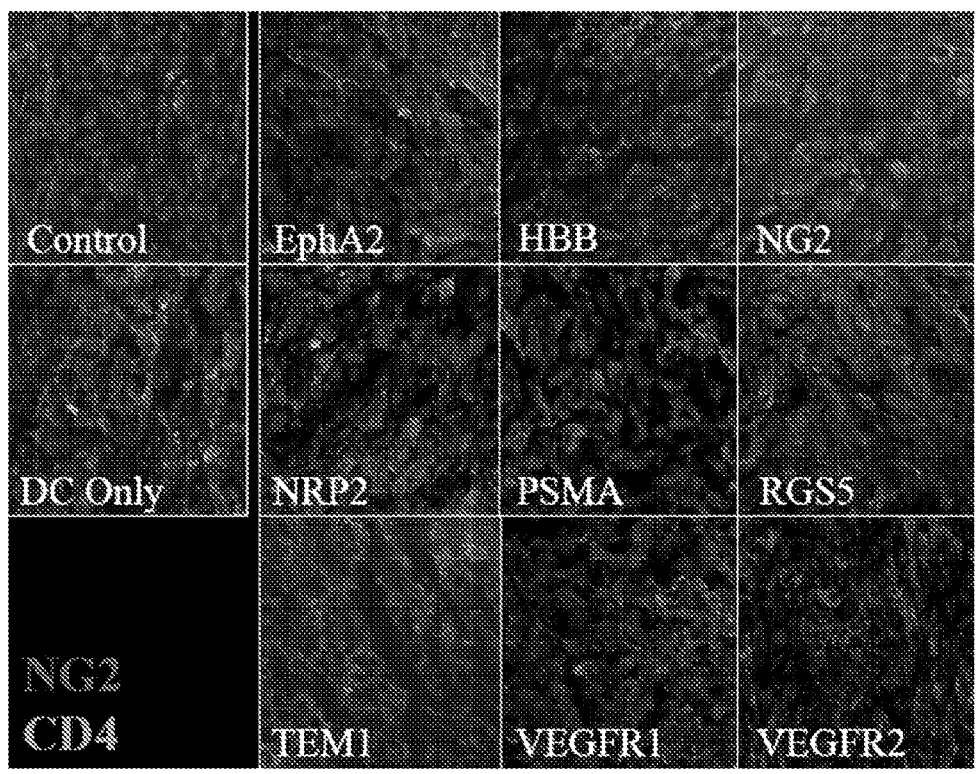
Figure 17B:
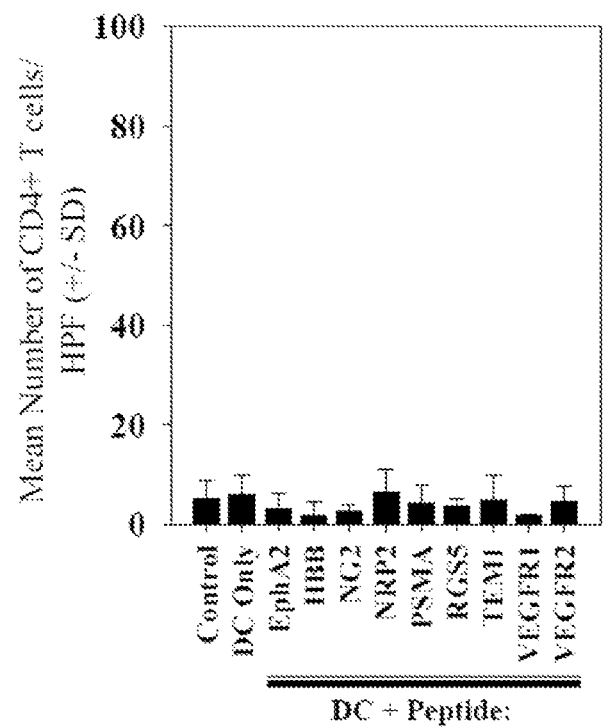

FIGS. 17A-17B show a series of digital images and a graph illustrating the lack of vaccine-induced impact on CD4+ T cell infiltration into MC38 tumor lesions. In FIG. 17A, tumor sections prepared as described in FIG. 10 were stained using antibodies against CD4 (green) and NG2 (red), then counterstained using DAPI (blue). The mean number of CD4+ TIL per HPF (+/−SD) was determined over a total of ten fields (FIG. 17B).

Figure 18:
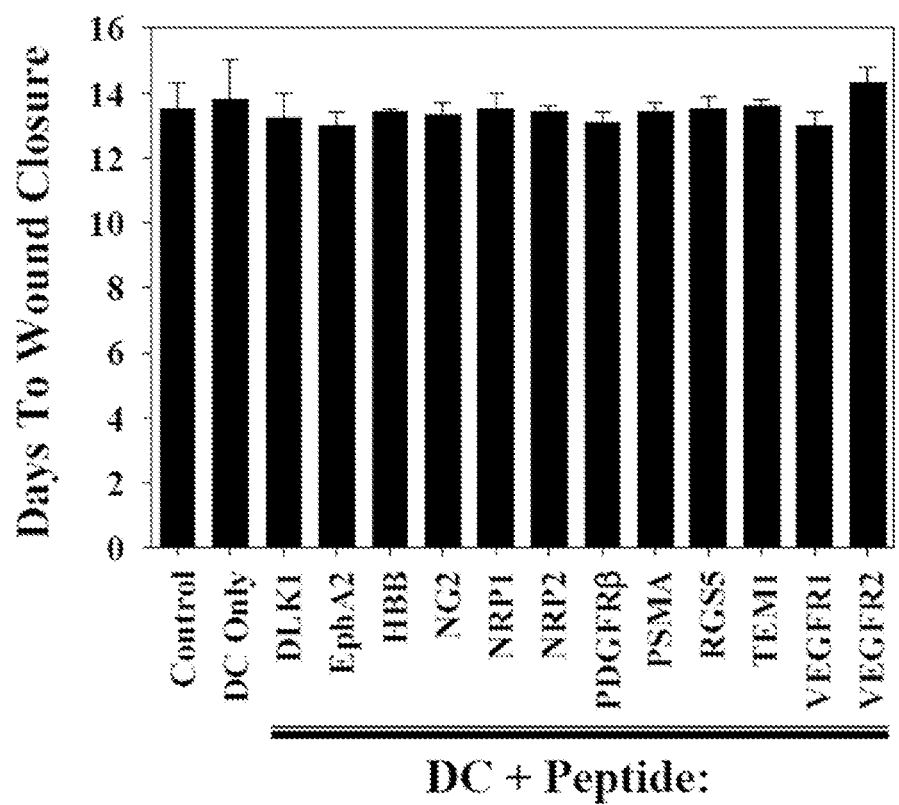

FIG. 18 shows a graph illustrating that prior vaccination against TASA does not inhibit wound-healing in HHD mice. Female HHD mice (5 animals/cohort) were vaccinated in the right flank on d-14 and d-7 with saline, 106 DC.IL12 alone or 106 DC.IL12 pulsed with peptides derived from the indicated TASA. In cases where more than one peptide is identified for a given TASA, an equimolar pool of the indicated peptides (each 10 μM) was pulsed onto DC.IL12 and used for vaccination in the relevant cohort. On d0, mice were anesthetized, with skin on the upper back shaved and sterilized topically, before placement of two 3-mm diameter wounds using a sterilized punch biopsy instrument. Wounds were not treated consequently and no infections were observed in any animals. The time to closure for the 10 wounds/cohort (2 sites/animal×5 mice/group) were assessed daily and is reported as the mean number of days+/−SD for complete wound closure.

FIGS. 19A-19C show that DLK1 is differentially expressed on RENCA tumor-associated pericytes. RENCA tumor cells were injected subcutaneously (s.c.) into female BALB/c mice and allowed to progress for 21 days after which animals were euthanized and tumors and normal kidneys were removed. In FIG. 19A, tissues were processed into single-cell suspension and sorted by flow cytometry based on forward scatter and side scatter, DAPI exclusion (to exclude dead cells), a $CD45^{neg}$ phenotype, and then selectively into $CD146^+CD34^{neg}$ pericytes and $CD146^+CD34^+$ VEC populations. In FIG. 19B, mRNA was isolated from sorted pericytes and VEC from normal kidney and RENCA tumor and analyzed for DLK1 expression by real-time PCR. Relative mRNA expression was normalized to housekeeping HPRT1 expression. In FIG. 19C, day 21 RENCA tumor tissue sections were analyzed for expression of CD31, NG2, and DLK1 by fluorescence microscopy. Data are representative of 3 experiments performed.

FIGS. 20A-20D show that DC/DLK1 peptide vaccines are immunogenic and therapeutic in the RENCA model. (FIGS. 20A-20C) BALB/c mice were inoculated with RENCA tumor cells s.c. on the right flank on day 0. In FIG. 20A, After randomizing for similar mean tumor size per treatment cohort (n=5), mice were injected s.c. on their left flank on days 7 and 14 (post-tumor inoculation) PBS, $10^6$ DC.IL12 or $10^6$ DC.IL12 pre-pulsed with equimolar mix (10 μM each) of the 3 synthetic DLK1 peptides. Tumor growth (mean±SD) was then followed over time. In FIG. 20B, on day 20 post-tumor inoculation, splenic CD8+ T cells were isolated from each cohort and co-cultured with syngenic DC pre-pulsed with individual DLK1 peptides for 24 h, at which time, IFN-γ ELISA were performed on the harvested cell-free supernatants. In FIGS. 20C and 20D, day 20 tumors were fixed, sectioned and analyzed by immunofluorescence microscopy; CD31 (bright grey in FIGS. 20C, 20D), VCAM1 (medium grey in FIG. 20C), CXCL10 (medium grey in FIG. 20D). The percentage of VCAM1 co-localization with CD31 is depicted as a yellow signal in FIG. 20C. Histograms to the right of images reflect mean quantitation (+/−SD) of color pixels from 3 independent fields per slide. Data are representative of 3 independent experiments performed. *p<0.05 versus control treatments (ANOVA).

FIGS. 21A-21E show that Recombinant lentiviral (lv) DLK1-based vaccines are therapeutic and promote a Type-1-polarized TME. (FIGS. 21A-D) BALB/c mice were inoculated s.c. with RENCA tumor cells in the right flank on day 0. (FIG. 21A) After cohort (n=5) randomization for similar mean tumor size on day 10 post-tumor inoculation, mice were treated i.d. in the left flank with 40 TU or 200 TU of lvDLK1 or lvNEG. Tumor size was then monitored longitudinally. In FIGS. 21B, 21C and 21D, on day 27 post-tumor inoculation, mice were euthanized and tumors resected, fixed, sectioned and analyzed by immunofluorescence microscopy for expression of (FIG. 21B) CD31 (brigh) and DLK1 (medium grey) with arrows indicating DLK1+ cells, (FIG. 21C) CXCL10 and (FIG. 21D) co-localization of VCAM1 with CD31. In FIG. 21E, CD8+ TIL quantitation is provided. The presented histograms reflect mean quantitation (+/−SD) of color pixels from 3 independent fields per slide. Data are representative of 3 independent experiments performed. *p<0.05 versus control treatments (ANOVA).

Figure 6:
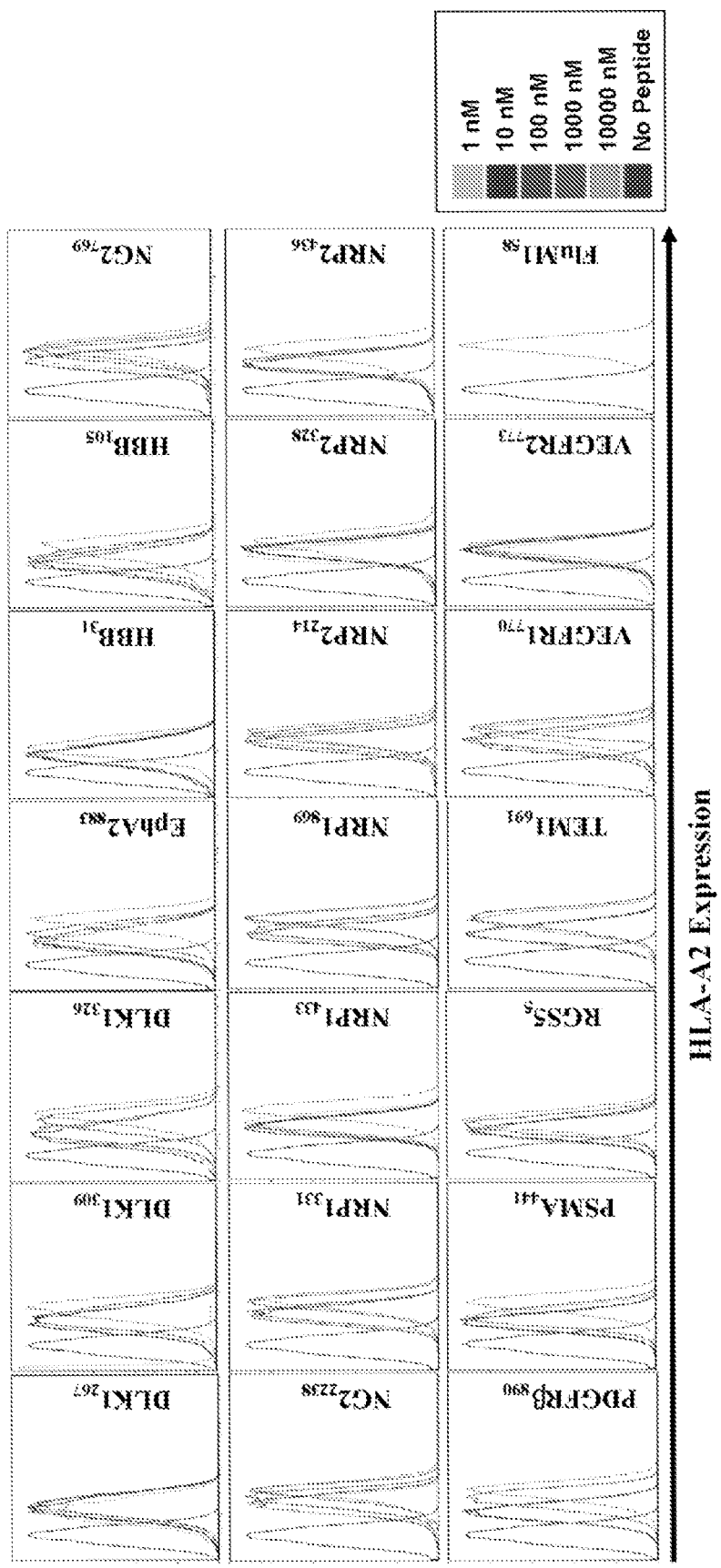
FIG. 6 shows a series of graphs illustrating that TASA-derived peptides bind to HLA-A2 to a variable degree based on the T2 class I stabilization assay. Peptide stabilization of HLA-A2 complexes on the T2 cell line by synthetic peptides was assessed as previously described (Stuber et al., *Eur. J. Immunol.*, 24: 765-768, 1994. FluM$1_{58-66}$ (GILGFVFTL) was used as a positive HLA-A2 binding control peptide (Tatsumi et al., *Cancer Res.*, 63: 4481-4489, 2003). Overlays of fluorescence histograms are provided for each peptide over a 1-10000 nM dose range, as indicated. Evidence for productive stabilization of HLA-A2 complexes is supported by a shift in staining intensity to the right vs. the no peptide control. Negative control (HLA-A3/A11-binding) HIV-$nef_{73-82}$ peptide (Tatsumi et al., *Cancer Res.*, 63: 4481-4489, 2003) failed to promote enhanced HLA-A2 stabilization on T2 cells. Data are from one representative experiment of three independent assays performed.

FIGS. 22A-22D show that recombinant lvDLK1-based vaccines promote normalization of the tumor vasculature. Mice bearing day 10 RENCA tumors were treated with lvDLK1 or lvNEG as outlined in FIG. 21. On day 27 post-tumor inoculation, mice were euthanized and resected and evaluated macroscopically and for hemoglobin content (FIG. 21A). In FIGS. 21B and 21C, tumor sections were analyzed by immunofluorescence microscopy for expression of CD31 (bright grey) and NG2 (dark grey). In FIG. 21B, 6 μm sections were imaged by wide-field microscopy, while in FIG. 21C, 30 μm sections were imaged by confocal microscopy to generate 3D reconstructions. For FIG. 21B, mean data±SD of three independent fields per slide is reported for each group from 1 representative experiment of 3 performed. In repeated experiments (FIG. 21D), treated mice received intravenous injections of tomato lectin-FITC to label endothelium (bight grey) and 20 nm FLUORSPHEREs® to assess vascular permeability (dark grey) on day 24 post-tumor inoculation. Whole tumor tissue was then imaged immediately by confocal microscopy at a depth of 17 μm. *p<0.05 for lvDLK1 versus lvNEG (t-test).

Figures 23B, 23C, 23D, 23E:
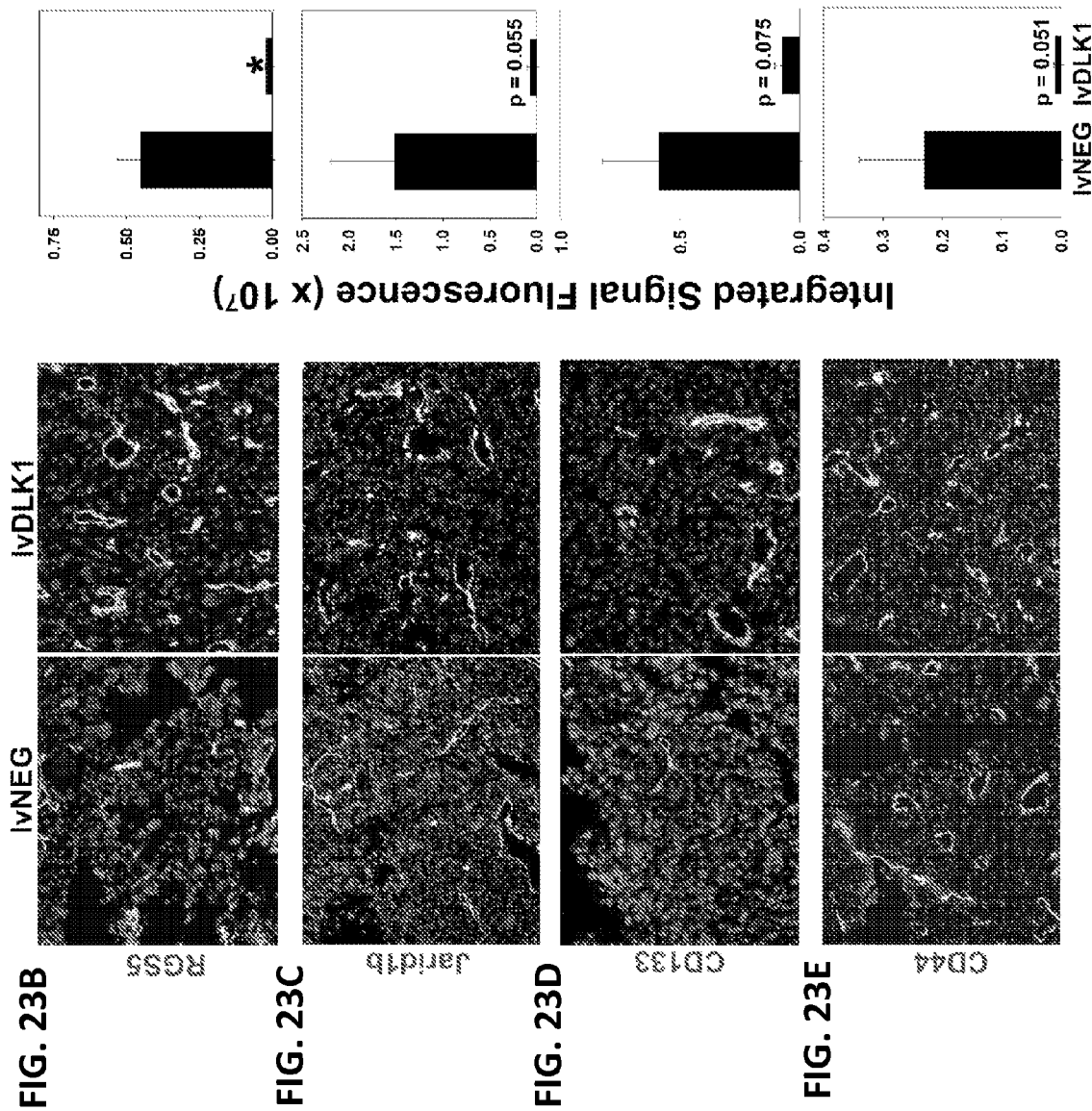

FIGS. 23A-23E show recombinant lvDLK1-based vaccines promote normoxia in the TME in association with the loss of cells bearing stem cell-like phenotypes. Mice bearing day 10 RENCA tumors were treated with lvDLK1 or lvNEG as outlined in FIG. 21. In FIG. 23A, on day 21, mice were injected i.p. with the hypoxia probe pimonidazole hydrochloride and euthanized, with tumors resected, sectioned, and analyzed by HRP-immunohistochemistry. In FIGS. 21B-

21E, day 21 tumor-bearing mice that did not receive pimonidazole hydrochloride were euthanized, with tumors resected, fixed, sectioned and analyzed by immunofluorescence microscopy for expression of CD31 and RGS5 (FIG. 21B), Jarid1b (FIG. 21C), CD133 (FIG. 21D) and CD44 (FIG. 21E). The presented histograms reflect mean quantitation (+/−SD) of color pixels from 3 independent fields per slide. Data are representative of 3 independent experiments performed. *p<0.05 for lvDLK1 versus lvNEG (t-test).

Figure 24:
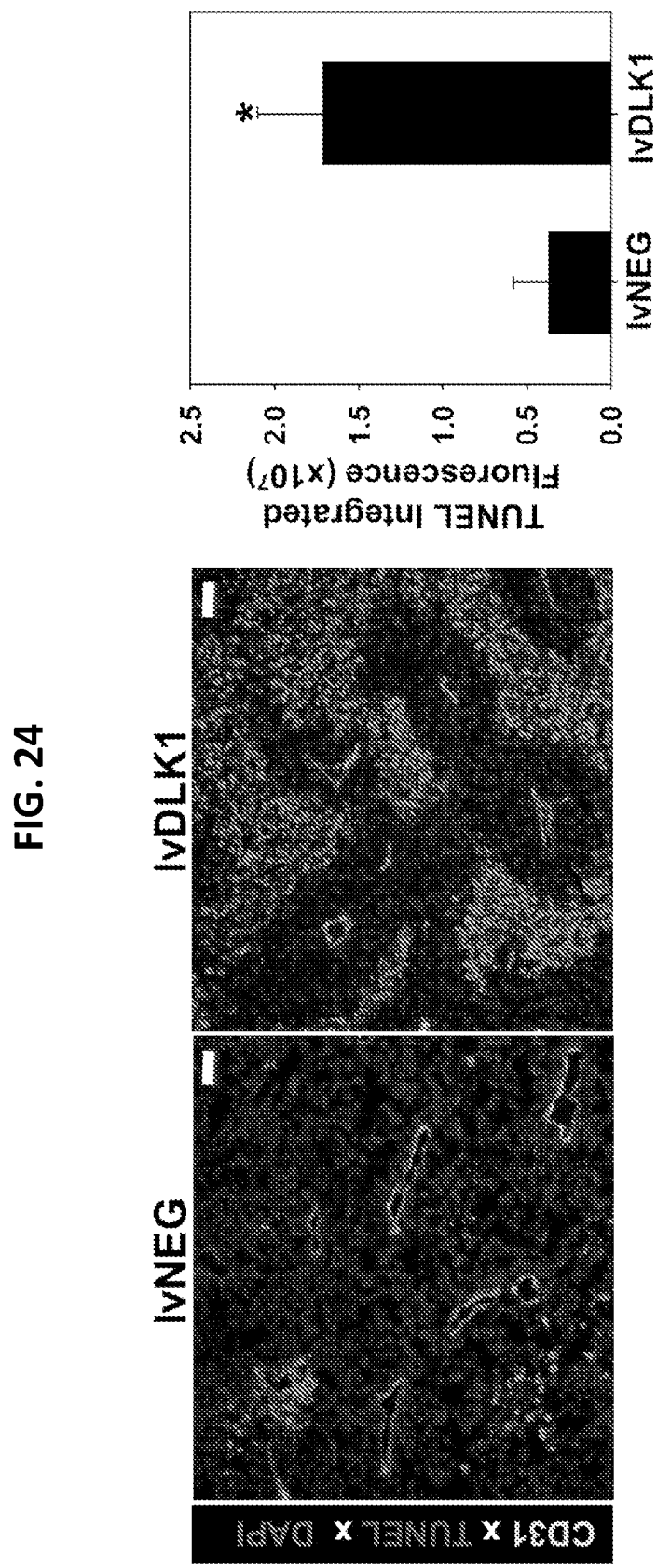

FIG. 24 shows vascular remodeling after recombinant lvDLK1-based vaccination results in the development of apoptotic "dead zones" in the TME distal to residual blood vessels. Mice bearing day 10 RENCA tumors were treated with lvDLK1 or lvNEG as outlined in FIG. 21. On day 24 post-tumor inoculation, mice were euthanized, with tumors resected, fixed, sectioned and analyzed for expression of CD31 (bright grey) and apoptotic nuclear staining with TUNEL reagent (dark grey). The presented histograms reflect mean quantitation (+/−SD) of color pixels from 3 independent fields per slide. Data are representative of 3 independent experiments performed. *p<0.05 for lvDLK1 versus lvNEG (t-test).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (106 kb), which was created on Oct. 30, 2015, which is incorporated by reference herein.

In the accompanying sequence listing:
SEQ ID NO: 1 is an exemplary amino acid sequence of an immunogenic DLK1 polypeptide.
SEQ ID NO: 2 is an exemplary amino acid sequence of an immunogenic DLK1 polypeptide.
SEQ ID NO: 3 is an exemplary amino acid sequence of an immunogenic DLK1 polypeptide.
SEQ ID NO: 4 is an exemplary amino acid sequence of an immunogenic HBB polypeptide.
SEQ ID NO: 5 is an exemplary amino acid sequence of an immunogenic HBB polypeptide.
SEQ ID NO: 6 is an exemplary amino acid sequence of an immunogenic NRP1 polypeptide.
SEQ ID NO: 7 is an exemplary amino acid sequence of an immunogenic NRP1 polypeptide.
SEQ ID NO: 8 is an exemplary amino acid sequence of an immunogenic NRP1 polypeptide.
SEQ ID NO: 9 is an exemplary amino acid sequence of an immunogenic TEM1 polypeptide.
SEQ ID NO: 10 is an exemplary amino acid sequence of an immunogenic EphA2 polypeptide.
SEQ ID NO: 11 is an exemplary amino acid sequence of an immunogenic RGS5 polypeptide.
SEQ ID NO: 12 is an exemplary amino acid sequence of an immunogenic PDGFRβ polypeptide.
SEQ ID NO: 13 is an exemplary amino acid sequence of an immunogenic NG2 polypeptide.
SEQ ID NO: 14 is an exemplary amino acid sequence of an immunogenic NG2 polypeptide.
SEQ ID NO: 15 is an exemplary amino acid sequence of an immunogenic NRP2 polypeptide.
SEQ ID NO: 16 is an exemplary amino acid sequence of an immunogenic NRP2 polypeptide.
SEQ ID NO: 17 is an exemplary amino acid sequence of an immunogenic NRP2 polypeptide.
SEQ ID NO: 18 is an exemplary amino acid sequence of an immunogenic PSMA polypeptide.
SEQ ID NO: 19 is an exemplary amino acid sequence of an immunogenic VEGFR1 polypeptide.
SEQ ID NO: 20 is an exemplary amino acid sequence of an immunogenic VEGFR2 polypeptide.
SEQ ID NO: 21 is an exemplary amino acid sequence of DLK1.
SEQ ID NO: 22 is an exemplary amino acid sequence of HBB.
SEQ ID NO: 23 is an exemplary amino acid sequence of NRP1.
SEQ ID NO: 24 is an exemplary amino acid sequence of TEM1.
SEQ ID NO: 25 is an exemplary amino acid sequence of EphA2.
SEQ ID NO: 26 is an exemplary amino acid sequence of RGS5.
SEQ ID NO: 27 is an exemplary amino acid sequence of PDGFRβ.
SEQ ID NO: 28 is an exemplary amino acid sequence of NG2.
SEQ ID NO: 29 is an exemplary amino acid sequence of NRP2.
SEQ ID NO: 30 is an exemplary amino acid sequence of PSMA.
SEQ ID NO: 31 is an exemplary amino acid sequence of VEGFR1.
SEQ ID NO: 32 is an exemplary amino acid sequence of VEGFR2.
SEQ ID NO: 33-64 are the nucleic acid sequences of primers.
SEQ ID NO: 65 is the amino acid sequence of $DLK1_{158-166}$.
SEQ ID NO: 66 is the amino acid sequence of $DLK1_{161-169}$.
SEQ ID NO: 67 is the amino acid sequence of $DLK1_{259-270}$ and $DLK1_{262-270}$.
SEQ ID NOs: 68-83 are peptide sequences.
SEQ ID NO: 84 is the amino acid sequence of a linker.

DETAILED DESCRIPTION

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided, along with particular examples:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunstimulatory oligonucleotides (such as those including a CpG motif) can also be used as adjuvants (for example see U.S. Pat. No. 6,194,388; U.S. Pat. No. 6,207,646; U.S. Pat. No. 6,214, 806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules.

Administration: To provide or give a subject an agent, for example, a composition that includes a immunogenic TASA peptide, by any effective route. Exemplary routes of administration include, but are not limited to, oral, injection (such as subcutaneous, intramuscular, intradermal, intraperitoneal, and intravenous) and transdermal (e.g., topical).

Agent: Any substance or any combination of substances that is useful for achieving an end or result; for example, a substance or combination of substances useful for decreasing or reducing a tumor in a subject. In some embodiments, the agent is a chemotherapeutic agent, toxin or anti-angiogenic agent. The skilled artisan will understand that particular agents may be useful to achieve more than one result.

Angiogenesis: A biological process leading to the generation of new blood vessels through sprouting or growth from pre-existing blood vessels. The process involves the migration and proliferation of endothelial cells from preexisting vessels. Angiogenesis occurs during pre- and post-natal development, and in the adult. Angiogenesis occurs during the normal cycle of the female reproductive system, wound healing, and during pathological processes such as cancer, where it is essential for the growth of solid tumors (for review, see Battegay, *J. Molec. Med.*, 73(7): 333-346, 1995; Shchors and Evan, *Cancer Res.*, 67:1630-1633. 2007).

Anti-angiogenic agent: A molecule that decreases or reduces angiogenesis, for example, a molecule that decreases pathological angiogenesis. Additional anti-angiogenic agents include, but are not limited to, vascular endothelial growth factor receptor 2 (VEGFR2) antibodies such as bevacizumab, as well as small molecule tyrosine kinase inhibitors, such as sunitinib. See also, Liu et al., *Seminars in Oncology*, 29(11): 96-103, 2002; Shepherd et al., *Lung Cancer* 34:S81-S89, 2001).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, at least 5, at least 9, at least 10, at least 11, at least 12, or about 9-12 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tumor formation, such as prostate cancer and/or uterine cancer and/or testicular cancer. A disease-specific antigen can be an antigen recognized by T cells or B cells.

Cancer, Tumor or Neoplasia: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Tumors of the same tissue type are primary tumors originating in a particular organ (such as colon or skin). Tumors of the same tissue type may be divided into tumors of different sub-types.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

cDNA (complementary DNA): A piece of DNA lacking internal, non-coding segments (introns) and regulatory sequences that determine transcription. cDNA is synthesized in the laboratory by reverse transcription from messenger RNA extracted from cells.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemotherapeutic agent: Any chemical agent with therapeutic usefulness in the treatment of diseases characterized by abnormal cell growth. For example, chemotherapeutic agents are useful for the treatment of cancer, including colorectal and skin cancer. In one embodiment, a chemotherapeutic agent is a radioactive compound. In particular examples, such chemotherapeutic agents are administered in combination with a treatment that decreases or reduces a tumor or angiogenesis (for example before, during or after administration of a therapeutically effective amount of one or more immunogenic TASA peptides or a composition including a plurality of immunogenic polypeptides). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy, Ch.* 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Williams & Wilkins, 2005; Skeel, *Handbook of Cancer Chemotherapy* (6th ed.). Lippincott Williams & Wilkins, 2003). Combination chemotherapy is the administration of more than one agent to treat cancer.

Colorectal cancer: A neoplastic tumor of colon, rectum or anus tissue that is or has the potential to be malignant. The main types of colorectal cancer include colorectal carcinomas such as adenocarcinoma and squamous cell carcinoma. Infiltrating (malignant) carcinoma of the colon can be divided into stages (I, II, III and IV). See, e.g., Blake et al. (eds.), *Gastrointestinal Oncology: A practical Guide*, Berlin: Springer-Verlag, 2011.

Consists Of: With regard to a polypeptide, a polypeptide that consists of a specified amino acid sequence does not include any additional amino acid residues, nor does it include additional non-peptide components, such as lipids, sugars or labels.

Conservative variants: "Conservative" amino acid substitutions are those substitutions that do not substantially affect or decrease an activity or antigenicity of an antigenic epitope of DLK1. Specific, non-limiting examples of a conservative substitution include the following examples:

| Original Residue | Conservative Substitutions |
| --- | --- |
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that reduce an activity or antigenicity.

Contacting: Placement in direct physical association, for example solid, liquid or gaseous forms. Contacting includes, for example, direct physical association of fully- and partially-solvated molecules.

Costimulatory molecule: Although engagement of the T-cell receptor with peptide-MHC delivers one signal to the T cell, this signal alone can be insufficient to activate the T cell. Costimulatory molecules are molecules that, when bound to their ligand, deliver a second signal enhancing activation of the T cell. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Decrease or Reduce: To reduce the quality, amount, or strength of something; for example a reduction in tumor burden. In one example, a therapy reduces a tumor (such as the size of a tumor, the number of tumors, the metastasis of a tumor, or combinations thereof), or one or more symptoms associated with a tumor, for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Degenerate variant: A polynucleotide encoding a immunogenic TASA peptide that includes a sequence that is degenerate as a result of the genetic code. There are 20 natural amino acids, most of which are specified by more than one codon. Therefore, all degenerate nucleotide sequences are included in this disclosure as long as the amino acid sequence of the immunogenic TASA peptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Effective amount: The amount of an agent (such as a immunogenic TASA peptide or a composition comprising a plurality of immunogenic polypeptides) that alone, or together with one or more additional agents, induces the desired response, such as, for example induction of an immune response to a TASA.

Epitope: An antigenic determinant. These are particular chemical groups or peptide sequences on a molecule that are antigenic (that elicit a specific immune response). An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic composition: A composition comprising an immunogenic TASA peptide or a plurality of immunogenic TASA peptides, or one or more polynucleotides encoding the immunogenic TASA peptide or plurality of immunogenic TASA peptides that induces a measurable CTL response against cells expressing the corresponding TASA, or induces a measurable B cell response (such as production of antibodies that specifically bind the corresponding TASA) against a TASA peptide. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant.

Immunogenic TASA peptide: A peptide which comprises an allele-specific motif or other sequence of a tumor associated stromal cell antigen, such that the peptide will bind an MHC molecule and induce a cytotoxic T lymphocyte ("CTL") response, or a B cell response (e.g. antibody production) against the antigen from which the immunogenic peptide is derived.

In one example, an immunogenic TASA peptide is a series of contiguous amino acid residues from a TASA generally between 7 and 20 amino acids in length, such as about 8 to 11 residues in length. Specific immunogenic TASA peptides are disclosed herein that are 9 or 10 amino acid residues in length, or at most 12 amino acids in length, such as 8-15 amino acids in length. Generally, immunogenic TASA peptides can be used to induce an immune response in a subject, such as a B cell response or a T cell response. In one example, an immunogenic TASA peptide, when bound to a Major Histocompatibility Complex Class I molecule, activates cytotoxic T lymphocytes (CTLs) against cells expressing the corresponding wild-type TASA protein. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Isolated: A biological component (such as a nucleic acid, peptide, protein or protein complex) that has been substantially separated, produced apart from, or purified away from other biological components in the cell of the organism in which the component naturally occurs, i.e., other chromosomal and extrachromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example a polypeptide, can be at least 50%, at least 60%, at least 70%, at least 80%, at least 90%, at least 95%, at least 96%, at least 97%, at least 98%, or at least 99% pure. The epitopes of TASA disclosed herein can be isolated (and/or synthesized) by any means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Linker: The terms "conjugating," "joining," "bonding," "labeling" or "linking" refer to making two molecules into one contiguous molecule; for example, linking two polypeptides into one contiguous polypeptide, or covalently attaching an effector molecule or detectable marker radionuclide or other molecule to a polypeptide. The linkage can be either by chemical or recombinant means. "Chemical means" refers to a reaction between the antibody moiety and the effector molecule such that there is a covalent bond formed between the two molecules to form one molecule.

In some embodiments, a linker is an amino acid sequence that covalently links two polypeptide domains. For example, such linkers can be included in the between the immunogenic TASA epitopes disclosed herein to provide rotational freedom to the linked polypeptide domains and thereby to promote proper domain folding and presentation to a MHC. By way of example, in a recombinant polypeptide comprising two immunogenic TASA peptide domains, linker sequences can be provided between them, such as a polypeptide comprising immunogenic TASA peptide-linker-immunogenic TASA peptide. Linker sequences, which are generally between 2 and 25 amino acids in length, are well known in the art and include, but are not limited to, the glycine(4)-serine spacer (GGGGS (SEQ ID NO: 84)×3) described by Chaudhary et al., *Nature* 339:394-397, 1989.

Lymphocytes: A type of white blood cell that is involved in the immune defenses of the body. There are two main types of lymphocytes: B cells and T cells.

Major Histocompatibility Complex (MHC): A generic designation meant to encompass the histocompatability antigen systems described in different species, including the human leukocyte antigens ("HLA").

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes an immunogenic TASA peptide. Generally, operably linked DNA sequences are contiguous and, where necessary to join two protein-coding regions, in the same reading frame.

Pathological angiogenesis: Angiogenesis that is medically undesired or harmful to a subject, such as angiogenesis associated with a tumor or the generation of blood vessels in or surrounding a tumor. Other examples of pathological angiogenesis include corneal or retinal angiogenesis (as in a corneal transplant or the retina of a subject with macular degeneration or diabetes).

Peptide Modifications: Immunogenic TASA peptides include synthetic embodiments of peptides described herein. In addition, analogs (non-peptide organic molecules), derivatives (chemically functionalized peptide molecules obtained starting with the disclosed peptide sequences) and variants (homologs) of these peptides can be utilized in the methods described herein. Each peptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic TASA peptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers provided herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide or Peptide: A polymer in which the monomers are amino acid residues that are joined together through amide bonds. The amino acids included in a polypeptide may be subject to post-translational modification (e.g., glycosylation or phosphorylation). A polypeptide or peptide can be between 3 and 30 amino acids in length. In one embodiment, a polypeptide or peptide is from 8 to 12 amino acids in length. In several embodiments, a polypeptide or peptide is at most 12 amino acids in length, for example, 9, 10, 11 or 12 amino acids in length. In some embodiments, a protein is at least 100 amino acids in length, for example, at least 150, at least 200, at least 250, at least 300, at least 350, at least 400, at least 450, or at least 500 amino acids in length.

Plurality: Two or more of a molecule, such as 2, 3, 4, 5, 6, 7, 8, 9, 10, 11, 12 or more of a molecule.

Promoter: An array of nucleic acid control sequences which direct transcription of a nucleic acid. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters include, but are not limited to the SV40 promoter, the CMV enhancer-promoter, and the CMV enhancer/β-actin promoter. Both constitutive and inducible promoters are included (see e.g., Bitter et al., *Methods in Enzymology* 153:

516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of an immunogenic TASA peptide or DLK1 will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of an immunogenic TASA peptide or DLK1 are typically characterized by possession of at least 75%, for example at least 80%, sequence identity counted over the full length alignment with the amino acid sequence of the immunogenic TASA peptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Skin cancer: A neoplastic tumor of skin tissue that is or has the potential to be malignant. Melanoma is a skin cancer of transformed melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism), which is a marker of aggressive behavior and a tendency for local recurrence. Other melanomas include clear cell sarcoma, mucosal melanoma and uveal melanoma. Melanoma is staged from I to IV. See, e.g., Thompson et al. (eds), *Textbook of Melanoma: Pathology, Diagnosis and Management*, London: Taylor & Francis, 2004.

Stromal cells: Cells forming the connective tissue of any organ. Examples of stromal cells include fibroblasts (such as myofibroblasts), leukocytes, pericytes (such as vascular pericytes) and endothelial cells (such as vascular endothelial cells).

Subject: Any mammal, such as humans, non-human primates, pigs, sheep, cows, rodents and the like. In two non-limiting examples, a subject is a human subject or a murine subject. Thus, the term "subject" includes both human and veterinary subjects.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

Tumor Associated Microenvironment (TME): A tumor and the area immediately surrounding a tumor, including, for example, blood vessels intersecting or contacting the tumor.

Tumor Associated Stromal Cell: A stromal cell included in a tumor or the tumor microenvironment. For example, vascular endothelial cells (VECs) and pericytes included in blood vessels intersecting or contacting tumor.

Tumor Associated Stromal Cell Antigen (TASA): An antigenic molecule expressed by a tumor associated stromal cell. Examples of TASA include Protein Delta Homolog 1 (DLK1; SEQ ID NO: 21), Hemoglobin Subunit Beta (HBB; SEQ ID NO: 22), Neuropilin 1 (NRP1; SEQ ID NO: 23), Tumor Endothelial Marker 1 (TEM1; SEQ ID NO: 24), Ephrin Type A Receptor 2 (EphA2; SEQ ID NO: 25), Regulator of G-Protein Signaling 5 (RGS5; SEQ ID NO: 26), Platelet Derived Growth Factor Receptor β (PDGFRβ; SEQ ID NO: 27), melanoma chondroitin sulfate proteoglycan (NG2; SEQ ID NO: 28), Neuropilin 2 (NRP2; SEQ ID NO: 29), Glutamate Carboxypeptidase 2, (PSMA; SEQ ID NO: 30), Vascular Endothelial Growth Factor 1 (VEGFR1; SEQ ID NO: 31), Vascular Endothelial Growth Factor Receptor 2 (VEGFR2; SEQ ID NO: 32). (See, e.g., Komita et al., *Cancer Res.*, 68: 8076-8084, 2008; Hatano et al., *J. Transl. Med.*, 2: 40, 2004; Maciag et al., *Cancer Res.*, 68: 8066-8075, 2008; Ishizaki et al., *Clin. Cancer Res.*, 12: 5841-5849, 2006; Wada et al., *Cancer Res.*, 65: 4939-4946, 2005; Kaplan et al., *Vaccine*, 24:

6994-7002, 2006; Liu et al., *Cytokine*, 32: 206-212, 2005; Silver et al., *Clin. Cancer Res.*, 3: 81-85, 1997; Harada et al., *Oncol. Rep.*, 12: 601-607, 2004; Bondjers et al., *Am. J. Pathol.*, 162: 721-729, 2003; Boss et al., *Clin. Cancer Res.*, 13: 3347-3355, 2007; Christian et al., *Am. J. Pathol.*, 172: 486-494, 2008. Several embodiments include an immunogenic peptide from a TASA. In some embodiments, a plurality of immunogenic peptides from one or more TASA is provided in a composition.

Tumor burden: The total volume, number, metastasis, or combinations thereof of tumor or tumors in a subject.

Therapeutically effective amount: The amount of an agent (such as immunogenic TASA peptide, a DLK1 protein, a nucleic acid encoding the TASA peptide, a nucleic acid encoding DLK1 protein, or a composition including a plurality of immunogenic TASA peptides) that alone, or together with one or more additional agents, induces the desired response, such as, for example, induction of an immune response and/or treatment of a tumor in a subject. Ideally, a therapeutically effective amount provides a therapeutic effect without causing a substantial cytotoxic effect in the subject.

In one example, a desired response is to decrease the size, volume, or number (such as metastases) of a tumor in a subject. For example, the agent or agents can decrease the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of an immunogenic TASA peptide, a DLK1 protein, a nucleic acid encoding the TASA peptide, a nucleic acid encoding DLK1 protein, or composition including a plurality of immunogenic TASA peptides that is administered to a human or veterinary subject will vary depending upon a number of factors associated with that subject, for example the overall health of the subject. A therapeutically effective amount of the immunogenic TASA peptide, a DLK1 protein, a nucleic acid encoding the TASA peptide, a nucleic acid encoding DLK1 protein, or composition including a plurality of immunogenic polypeptides can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount can be dependent on the source applied, the subject being treated, the severity and type of the condition being treated, and the manner of administration.

Treating or Treatment: A therapeutic intervention (e.g., administration of a therapeutically effective amount of an immunogenic TASA peptide or composition including a plurality of immunogenic polypeptides) that ameliorates a sign or symptom of a disease or pathological condition related to a disease (such as a tumor). Treatment can also induce remission or cure of a condition, such as a tumor. In particular examples, treatment includes preventing a tumor, for example by inhibiting the full development of a tumor, such as preventing development of a metastasis or the development of a primary tumor. Prevention does not require a total absence of a tumor.

Reducing a sign or symptom associated with a tumor can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli*. Vectors also include viral vectors, such as, but are not limited to, retroviral, pox, adenoviral, herpes virus, alpha virus, baculovirus, Sindbis virus, vaccinia virus and poliovirus vectors.

Under conditions sufficient for: A phrase that is used to describe any environment that permits a desired activity. In one example the desired activity is formation of an immune complex. In particular examples the desired activity is treatment of a tumor.

Vascularization: The amount and type of blood vessels in a tissue or a cancer. Vascularization can be measured by a variety of methods, including histological methods. Tumor blood vessels have perivascular detachment, vessel dilation, and irregular shape. It is believed tumor blood vessels are not smooth like normal tissues, and are not ordered sufficiently to give oxygen to all of the tissues. If vascularization is "normalized" it is returned to a form in a normal (wildtype, not affected by disease), so that it is more ordered and reduced.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic TASA Peptides

Isolated polypeptides disclosed herein that include at most twelve amino acids from a tumor associated stromal cell antigen, such as Protein Delta Homolog 1 (DLK1; SEQ ID NO: 21), Hemoglobin Subunit Beta (HBB; SEQ ID NO: 22), Neuropilin 1 (NRP1; SEQ ID NO: 23), Tumor Endothelial Marker 1 (TEM1; SEQ ID NO: 24), Ephrin Type A Receptor 2 (EphA2; SEQ ID NO: 25), Regulator of G-Protein Signaling 5 (RGS5; SEQ ID NO: 26), Platelet Derived Growth Factor Receptor β (PDGFRβ; SEQ ID NO: 27), melanoma chondroitin sulfate proteoglycan (NG2; SEQ ID NO: 28), Neuropilin 2 (NRP2; SEQ ID NO: 29), Glutamate Carboxypeptidase 2, (PSMA; SEQ ID NO: 30), Vascular Endothelial Growth Factor 1 (VEGFR1; SEQ ID NO: 31), Vascular Endothelial Growth Factor Receptor 2 (VEGFR2; SEQ ID NO: 32). These polypeptides include an antigenic determinant from a TASA and are immunogenic, and thus can be used to induce an immune response in a subject.

The isolated TASA peptides, can be chemically synthesized by standard methods. If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding a TASA peptide or an epitope thereof into an expression vector, introducing the expression vector into a host cell, and isolating the polypeptide (see below).

The immunogenic TASA peptides include at most twelve amino acids, such as nine, ten, eleven or twelve consecutive amino acids of a TASA. For example, in some embodiments, the immunogenic TASA peptides includes at most twelve amino acids, at most eleven amino acids, at most ten amino acids or at most nine amino acids, wherein the polypeptide includes an amino acid sequence as shown in Table 1. In other embodiments, an immunogenic TASA peptide comprises or consists of $DLK1_{158-166}$ (CPPGFSGNF, SEQ ID NO: 65), $DLK1_{161-169}$ (GFSGNFCEI, SEQ ID NO: 66), or at least 9, 10, 11 or 12 amino acids of $DLK1_{259-270}$ and/or $DLK1_{262-270}$ (TILGVLTSLVVL, SEQ ID NO: 67 includes both of these epitopes). These immunogenic DLK1 peptides can be used individually. However, a combination of two or more of these DLK1 peptides can be utilized. In additional embodiments, the immunogenic TASA peptides includes at most twelve amino acids, at most eleven amino acids, at most ten amino acids or at most nine amino acids of an amino acid sequence as shown in Table 1. These TASA peptides can be used individually or in combination.

In several embodiments, the amino acid at position 2 of the immunogenic TASA peptide is substituted for a valine residue. In additional embodiments, the amino acid at position 9 of the immunogenic TASA peptide is substituted for a leucine residue.

TABLE 1

Immunogenic TASA Peptides.

| TASA Protein | Accession No.* | TASA Peptide | AA Positions | SEQ ID NO. |
|---|---|---|---|---|
| DLK1 | NP_003827.3 | $RLTPGVHEX_1$ wherein $X_1$ is a leucine or a valine | 269-277 | 1 |
| | | ILGVLTSLV | 310-318 | 2 |
| | | FLNKCETWV | 326-334 | 3 |
| HBB | CAG46711.1 | $RLLVVYPWX_2$ wherein $X_2$ is a threonine or a valine | 31-39 | 4 |
| | | $RLLGNVLVX_3V$ wherein $X_3$ is a cysteine or a valine | 105-114 | 5 |
| NRP1 | CAI16997.1 | GLLRFVTAV | 331-339 | 6 |
| | | $GX_4LGMVSGL$ wherein $X_4$ is a leucine or a methionine | 433-441 | 7 |
| | | VLLGAVCGV | 869-877 | 8 |
| TEM1 | AAG00867.1 | $LLVPTCVFX_5V$ wherein $X_5$ is a leucine or a valine | 691-700 | 9 |
| EphA2 | NP_004422.2 | TLADFDPRV | 883-891 | 10 |
| RGS5 | AAB84001.1 | $LX_6ALPHSCL$ wherein $X_6$ is a leucine or an alanine | 5-13 | 11 |
| PDGFRβ | AAA60049.1 | $ILLWEIFTX_7$ wherein $X_7$ is L or V | 890-898 | 12 |
| NG2 | AAQ62842 | $X_8LSNLSFPV$ wherein $X_8$ is I or T | 770-778 | 13 |
| | | LILPLLFYL | 2238-2246 | 14 |
| NRP2 | NP_957718.1 | DIWDGIPHV | 214-222 | 15 |
| | | YLQVDLRFL | 328-336 | 16 |
| | | NMLGMLSGL | 436-444 | 17 |
| PSMA | NP_004467.1 | LLQERGVAYI | 441-450 | 18 |
| VEGFR1 | NP_002010.2 | TLFWLLLTL | 770-778 | 19 |
| VEGFR2 | NP_002244.1 | VIAMFFWLL | 773-781 | 20 |

*Accession No. NP_003827.3 incorporated by reference herein as of Sep. 11, 2011; Accession No. CAG46711.1 incorporated by reference herein as of Oct. 16, 2008; Accession No. CAI16997.1 incorporated by reference herein as of Jan. 13, 2009; Accession No. AAG00867.1 incorporated by reference herein as of Aug. 23, 2000; Accession No. NP_004422.2 incorporated by reference herein as of Aug. 13, 2011; Accession No. AAB84001.1 incorporated by reference herein as of Nov. 8, 1997; Accession No. AAA60049.1 incorporated by reference herein as of Jan. 7, 1995; Accession No. NP_957718.1 incorporated by reference herein as of Aug. 21, 2011; Accession No. NP_004467.1 incorporated by reference herein as of Sep. 24, 2011; Accession No. NP_002010.2 incorporated by reference herein as of Sep. 25, 2011; Accession No. NP_002244.1 incorporated by reference herein as of Sep. 25, 2011.

Without being bound by theory, it is believed that the presentation of peptides by MHC Class I molecules involves binding to the cleft in an MHC Class I molecule through the anchor residues of the peptide and ultimate presentation on the cell surface. Depending upon the particular anchor residues, among other things, certain peptides can bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to CTL cells. HLA A, HLA B and HLA C molecules bind peptides of about eight to ten amino acids in length (such as nine amino acids in length) that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the immunogenic TASA peptides that are disclosed bind and are presented by HLA-A2.

Thus, in some examples, an isolated polypeptide includes at most 9, 10, 11 or 12 amino acids from DLK1, wherein the polypeptide includes an amino acid sequence set forth as RLTPGVHEX$_1$ (SEQ ID NO: 1) wherein X$_1$ is a leucine (L) or a valine (V). In some embodiments amino acid X$_1$ is a leucine (L). In other embodiments, amino acid X$_1$ is a valine (V). In one example the polypeptide consists of the amino acid sequence set forth as SEQ ID NO: 1. Thus, in one example, the polypeptide consists of SEQ ID NO: 1, wherein amino acid X$_1$ is a valine (V). In another example the polypeptide consists of SEQ ID NO: 1, wherein amino acid X$_1$ is a leucine (L).

In other examples, an isolated polypeptide includes at most 9, 10, 11 or 12 amino acids from DLK1, wherein the polypeptide includes an amino acid sequence set forth as ILGVLTSLV (SEQ ID NO: 2). In one example the polypeptide consists of the amino acid sequence set forth as SEQ ID NO: 2.

In additional examples, an isolated polypeptide includes at most 9, 10, 11 or 12 amino acids from DLK1, wherein the polypeptide includes an amino acid sequence set forth as FLNKCETWV (SEQ ID NO: 3). In one example the polypeptide consists of the amino acid sequence set forth as SEQ ID NO: 3.

In yet other examples, an isolated polypeptide that includes an isolated polypeptide includes at most 9, 10, 11 or 12 amino acids from DLK1, wherein the polypeptide includes one of SEQ DI NO: 65, SEQ ID NO: 66, or SEQ ID NO: 67. In several examples, the polypeptide consists of the amino acid sequence set forth as one of SEQ ID NO: 65, SEQ ID NO: 66 or SEQ ID NO: 67.

In further examples, an isolated polypeptide includes at most 9, 10, 11 or 12 amino acids from HBB, wherein the polypeptide includes an amino acid sequence set forth as RLLVVYPWX$_2$ (SEQ ID NO: 4) wherein X$_2$ is a threonine (T) or a valine (V). In further embodiments amino acid X$_2$ is a threonine (T). In other embodiments, amino acid X$_2$ is a valine (V). In one example the polypeptide consists of the amino acid sequence set forth as SEQ ID NO: 4. Thus, in one example, the polypeptide consists of SEQ ID NO: 4, wherein amino acid X$_2$ is a valine (V), and in another example the polypeptide consists of SEQ ID NO: 4, wherein amino acid X$_2$ is a threonine (T).

In still other examples, an isolated polypeptide includes at most 9, 10, 11 or 12 amino acids from HBB, wherein the polypeptide includes an amino acid sequence set forth as RLLGNVLVX$_3$V (SEQ ID NO: 5) wherein X$_3$ is a cysteine (C) or a valine (V). In additional embodiments amino acid X$_3$ is a cysteine (C). In other embodiments, amino acid X$_3$ is a valine (V). In one example the polypeptide consists of the amino acid sequence set forth as SEQ ID NO: 5. Thus, in one example, the polypeptide consists of SEQ ID NO: 5, wherein amino acid X$_3$ is a valine (V), and in another example the polypeptide consists of SEQ ID NO: 5, wherein amino acid X$_3$ is a cysteine (C).

In some examples, an isolated polypeptide includes at most 9, 10, 11 or 12 amino acids from NRP1, wherein the polypeptide includes an amino acid sequence set forth as GLLRFVTAV (SEQ ID NO: 6). In one example the polypeptide consists of the amino acid sequence set forth as SEQ ID NO: 6.

In additional examples, an isolated polypeptide includes at 9, 10, 11 or 12 twelve amino acids from NRP1, wherein the polypeptide includes an amino acid sequence set forth as GX$_4$LGMVSGL (SEQ ID NO: 7) wherein X$_4$ is a leucine (L) or a methionine (M). In still other embodiments, amino acid X$_4$ is a leucine (L). In other embodiments, amino acid X$_4$ is a methionine (M). In one example the polypeptide consists of the amino acid sequence set forth as SEQ ID NO: 7. Thus, in one example, the polypeptide consists of SEQ ID NO: 7, wherein amino acid X$_4$ is a methionine (M), and in another example the polypeptide consists of SEQ ID NO: 7, wherein amino acid X$_4$ is a leucine (L).

In further examples, an isolated polypeptide includes at most 9, 10, 11 or 12 amino acids from NRP1, wherein the polypeptide includes an amino acid sequence set forth as VLLGAVCGV (SEQ ID NO: 8). In one example the polypeptide consists essentially of the amino acid sequence set forth as SEQ ID NO: 8. In additional examples, the polypeptide is eleven amino acids in length, ten amino acids in length or nine amino acids in length. In further examples, the isolated polypeptide consists of the amino acid sequence set forth as SEQ ID NO: 8.

In other examples, an isolated polypeptide includes at most 9, 10, 11 or 12 amino acids from TEM1, wherein the polypeptide includes an amino acid sequence set forth as LLVPTCVFX$_5$V (SEQ ID NO: 9) wherein X$_5$ is a leucine (L) or a valine (V). In some embodiments, amino acid X$_5$ is a leucine (L). In other embodiments, amino acid X$_5$ is a valine (V). In one example the polypeptide consists of the amino acid sequence set forth as SEQ ID NO: 9. Thus, in one example, the polypeptide consists of SEQ ID NO: 9, wherein amino acid X$_5$ is a valine (V), and in another example the polypeptide consists of SEQ ID NO: 9, wherein amino acid X$_5$ is a leucine (L).

In additional examples, an isolated polypeptide includes at most 9, 10, 11 or 12 amino acids from EphA2, wherein the polypeptide includes an amino acid sequence set forth as TLADFDPRV (SEQ ID NO: 10), In one example the polypeptide consists of the amino acid sequence set forth as SEQ ID NO: 10.

In some examples, an isolated polypeptide includes at most 9, 10, 11 or 12 amino acids from RGS5, wherein the polypeptide includes an amino acid sequence set forth as LX$_6$ALPHSCL (SEQ ID NO: 11) wherein X$_6$ is a leucine (L) or an alanine (A). In further embodiments, amino acid X$_6$ is a leucine (L). In other embodiments, amino acid X$_6$ is an alanine (A). In one example the polypeptide consists of the amino acid sequence set forth as SEQ ID NO: 11. Thus, in one example, the polypeptide consists of SEQ ID NO: 11, wherein amino acid X$_6$ is an alanine (A), and in another example the polypeptide consists of SEQ ID NO: 11, wherein amino acid X$_6$ is a leucine (L).

In other examples, an isolated polypeptide includes at most 9, 10, 11 or 12 amino acids from PDGFRβ, wherein the polypeptide includes an amino acid sequence set forth as ILLWEIFTX$_7$ (SEQ ID NO: 12) wherein X$_7$ is a leucine (L) or a valine (V). In some embodiments, amino acid X$_7$ is a leucine (L). In other embodiments, amino acid X$_7$ is a valine (V). In one example the polypeptide consists of the amino acid sequence set forth as SEQ ID NO: 12. Thus, in one example, the polypeptide consists of SEQ ID NO: 12, wherein amino acid X$_7$ is a valine (V), and in another example the polypeptide consists of SEQ ID NO: 12, wherein amino acid X$_7$ is a leucine (L).

TABLE A

The following lists certain TASA peptides:

| TASA Protein | TASA Peptide | SEQ ID NO |
|---|---|---|
| DLK1 | RLTPGVHEL | 68 |
|  | RLTPGVHEV | 69 |
|  | ILGVLTSLV | 2 |
|  | FLNKCETWV | 3 |
| HBB | RLLVVYPWT | 70 |
|  | RLLVVYPWV | 71 |
|  | RLLGNVLVCV | 72 |
|  | RLLGNVLVVV | 73 |
| NRP1 | GLLRFVTAV | 6 |
|  | GLLGMVSGL | 74 |
|  | GMLGMVSGL | 75 |
|  | VLLGAVCGV | 8 |
| TEM1 | LLVPTCVFLV | 76 |
|  | LLVPTCVFVV | 77 |
| EphA2 | TLADFDPRV | 10 |
| RGS5 | LLALPHSCL | 78 |
|  | LAALPHSCL | 79 |
| PDGFRβ | ILLWEIFTV | 80 |
|  | ILLWEIFTL | 81 |
| NG2 | ILSNLSFPV | 82 |
|  | TLSNLSFPV | 83 |
|  | LILPLLFYL | 14 |
| NRP2 | DIWDGIPHV | 15 |
|  | YLQVDLRFL | 16 |
|  | NMLGMLSGL | 17 |
| PSMA | LLQERGVAYI | 18 |
| VEGFR1 | TLFWLLLTL | 19 |
| VEGFR2 | VIAMFFWLL | 20 |

In several embodiments, an immunogenic TASA peptide is included in a fusion protein. For example, each of the immunogenic TASA peptides included in a composition including a plurality of immunogenic TASA peptides (described herein) can be in the form of a fusion protein. Thus, the fusion protein can include an immunogenic TASA peptide and a second heterologous moiety, such as a myc protein, an enzyme or a carrier (such as a hepatitis carrier protein or bovine serum albumin) covalently linked to the immunogenic TASA peptide. A second heterologous moiety can be covalently or non-covalently linked to the immunogenic TASA peptide.

In additional embodiments, the immunogenic TASA peptides can be included in a fusion protein and can also include heterologous sequences. Thus, in several specific non-limiting examples, one or more of the immunogenic TASA peptides are included in a fusion polypeptide, for example a fusion of an immunogenic TASA peptide with six sequential histidine residues, a β-galactosidase amino acid sequence, or an immunoglobulin amino acid sequence. The immunogenic TASA peptides can also be covalently linked to a carrier. Suitable carriers include, but are not limited to, a hepatitis B small envelope protein HBsAg. This protein has the capacity to self assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

The fusion polypeptide can optionally include repetitions of one or more of any of the immunogenic TASA peptides disclosed herein. In one specific, non-limiting example, the fusion polypeptide includes two, three, four, five, or up to ten repetitions of an immunogenic TASA peptide. In another example, the fusion polypeptide can optionally include two or more different immunogenic TASA peptides disclosed herein, for example an immunogenic DLK1 peptide and an immunogenic TEM1 peptide. In one specific, non-limiting example, the fusion polypeptide includes two, three, four, five, or up to ten different immunogenic TASA peptides. A linker sequence can optionally be included between the immunogenic TASA peptides. In all of these examples, the polypeptide does not include the full-length TASA amino acid sequence.

In some embodiments, two or more different immunogenic TASA peptides can be included on a polypeptide, such as an immunogenic molecule. For example, 2-20 or more different immunogenic TASA peptides can be included in the polypeptide, such as 2, 3, 4, 5, 6, 7, 8, 9, 10, 11, 12, 13, 14, 15, 16, 17, 18, 19, 20 or more different immunogenic TASA peptides. The different immunogenic TASA peptides can be separated by peptide linkers. In some examples, several copies of the same immunogenic TASA peptide can be included in a polypeptide, such as an immunogenic molecule. For example a repeat of a immunogenic TASA peptide in series. In some examples, two, three, four, five or more copies of the same immunogenic TASA peptide are included in an polypeptide. In examples wherein two or more immunogenic TASA peptide are included on a polypeptide, the immunogenic TASA peptides can be separated by peptide linkers.

In additional embodiments, a plurality of the immunogenic TASA peptides described above is included in a composition. In one embodiment, the composition includes a plurality of immunogenic TASA peptides, wherein each immunogenic TASA peptide in the plurality is at most twelve amino acids in length, wherein the plurality of peptides includes at least two different immunogenic TASA peptides. Thus the composition can include 2, 3, 4, 5, 6, 7, 8, 9, 10 or more of the immunogenic TASA peptides disclosed in Table 1. In some embodiments, the composition includes 2, 3, 4, 5, 6 or 7 immunogenic peptides each from a different TASA. In other embodiments, the composition includes 2, 3, 4, 5, 6, 7, 8, 9 or 10 immunogenic peptides from 2, 3, 4, 5 or 6 different TASAs.

Compositions including a plurality of immunogenic TASA peptides described herein can include varying concentrations of different concentrations of each immunogenic TASA peptide in the plurality of immunogenic TASA peptides. For example, in some embodiments, the composition includes two, three, for, five, six, or seven different types of immunogenic TASA peptide in an equimolar ratio. In other examples, the composition includes two, three, for, five, six, or seven different types of immunogenic TASA peptide in a non-equimolar ratio.

In some embodiments, the composition includes immunogenic peptides from DLK1, HBB, NRP1 and TEM1. In other embodiments, the composition includes immunogenic peptides from DLK1, HBB, NRP1, TEM1, EphA2 and RGS5. In still other embodiments, the composition includes immunogenic peptides from DLK1, HBB, NRP1, TEM1, EphA2, RGS5 and PDGFRβ.

In some embodiments, a composition is provided including a plurality of immunogenic TASA peptides, wherein each immunogenic TASA peptide in the plurality is at most twelve amino acids in length, wherein the plurality of immunogenic TASA peptides includes at least one polypeptide including an amino acid sequence as shown for one of the DLK1 peptides listed in Table 1, at least one polypeptide including an amino acid sequence as shown for one of the HBB peptides listed in Table 1, at least one polypeptide including an amino acid sequence as shown for one of the NRP1 peptides listed in Table 1, and at least one polypeptide including an amino acid sequence as shown for one of the TEM1 peptides listed in Table 1. In some such embodiments, the plurality of polypeptides further includes at least one polypeptide including an amino acid sequence as shown for the EphA2 peptide listed in Table 1, and at least one polypeptide including an amino acid sequence as shown for one of the RGS5 peptides listed in Table 1. In still more embodiments, the plurality of polypeptides further includes at least one polypeptide including an amino acid sequence as shown for the EphA2 peptide listed in Table 1, at least one polypeptide including an amino acid sequence as shown for one of the RGS5 peptides listed in Table 1, and at least one polypeptide including an amino acid sequence as shown for one of the PDGFRβ peptides listed in Table 1. In some such embodiments, each polypeptide in the plurality of polypeptides is nine, ten, eleven or twelve amino acids in length.

In some embodiments, a composition is provided including a plurality of immunogenic TASA peptides including a polypeptide consisting of an amino acid sequence as shown for one of the DLK1 peptides listed in Table 1, a polypeptide consisting of an amino acid sequence as shown for one of the HBB peptides listed in Table 1, a polypeptide consisting of an amino acid sequence as shown for one of the NRP1 peptides listed in Table 1, and a polypeptide consisting of an amino acid sequence as shown for one of the TEM1 peptides listed in Table 1. In some embodiments, the composition further includes a polypeptide consisting of an amino acid sequence as shown for the EphA2 peptide listed in Table 1, and a polypeptide consisting of an amino acid sequence as shown for one of the RGS5 peptides listed in Table 1. In still more embodiments, the composition further includes a polypeptide consisting of an amino acid sequence as shown for the EphA2 peptide listed in Table 1, a polypeptide consisting of an amino acid sequence as shown for one of the RGS5 peptides listed in Table 1, and a polypeptide consisting of an amino acid sequence as shown for one of the PDGFRβ polypeptides listed in Table 1. In some such embodiments, each polypeptide in the plurality of polypeptides is nine, ten, eleven or twelve amino acids in length.

In some embodiments, a composition is provided including a plurality of immunogenic TASA peptides including a peptide comprising an amino acid sequence set forth as SEQ ID NO: 1, a peptide comprising an amino acid sequence set forth as SEQ ID NO: 2 and a peptide comprising an amino acid sequence set forth as SEQ ID NO:3. In other embodiments, a composition is provided including a plurality of immunogenic TASA peptides including a peptide comprising an amino acid sequence set forth as SEQ ID NO: 4 and a peptide comprising an amino acid sequence set forth as SEQ ID NO: 5. In still other embodiments, a composition is provided including a plurality of immunogenic TASA peptides including a peptide comprising an amino acid sequence set forth as SEQ ID NO: 6, a peptide comprising an amino acid sequence set forth as SEQ ID NO: 7 and a peptide comprising an amino acid sequence set forth as SEQ ID NO: 8. In some such embodiments, each polypeptide in the plurality of polypeptides is nine, ten, eleven or twelve amino acids in length.

In some embodiments, a composition is provided including a plurality of immunogenic TASA peptides including a DLK1 polypeptide comprising an amino acid sequence set forth as FLNKCETWV (SEQ ID NO: 3), a HBB polypeptide comprising an amino acid sequence set forth as RLLVVYPWX$_2$ (SEQ ID NO: 4) wherein X$_2$ is a threonine (T), a NRP1 polypeptide comprising an amino acid sequence set forth as VLLGAVCGV (SEQ ID NO: 8), a TEM1 polypeptide comprising an amino acid sequence set forth as LLVPTCVFX$_5$V (SEQ ID NO: 9) wherein X$_5$ is a leucine (L), an EphA2 polypeptide comprising an amino acid sequence set forth as TLADFDPRV (SEQ ID NO: 10), a RGS5 polypeptide comprising an amino acid sequence set forth as LX$_6$ALPHSCL (SEQ ID NO: 11) wherein X$_6$ is an alanine (A), a PDGFRβ polypeptide comprising an amino acid sequence set forth as ILLWEIFTX$_7$ (SEQ ID NO: 12) wherein X$_7$ is a leucine (L). In some such embodiments, each polypeptide in the plurality of polypeptides is at least nine, at least ten, at least eleven or at least twelve amino acids in length.

In some embodiments, a composition is provided including a plurality of immunogenic TASA peptides, wherein the plurality of immunogenic TASA peptides includes a DLK1 polypeptide consisting of an amino acid sequence set forth as FLNKCETWV (SEQ ID NO: 3), a HBB polypeptide consisting of an amino acid sequence set forth as RLLVVYPWX$_2$ (SEQ ID NO: 4) wherein X$_2$ is a threonine (T), a NRP1 polypeptide consisting of an amino acid sequence set forth as VLLGAVCGV (SEQ ID NO: 8) and a TEM1 polypeptide consisting of an amino acid sequence set forth as LLVPTCVFX$_5$V (SEQ ID NO: 9) wherein X$_5$ is a leucine (L). In some embodiments, the composition further includes an EphA2 polypeptide consisting of an amino acid sequence set forth as TLADFDPRV (SEQ ID NO: 10) and a RGS5 polypeptide consisting of an amino acid sequence set forth as LX$_6$ALPHSCL (SEQ ID NO: 11) wherein X$_6$ is an alanine (A). In some embodiments, the composition further includes an EphA2 polypeptide consisting of an amino acid sequence set forth as TLADFDPRV (SEQ ID NO: 10), a RGS5 polypeptide consisting of an amino acid sequence set forth as LX$_6$ALPHSCL (SEQ ID NO: 11) wherein X$_6$ is an alanine (A) and a PDGFRβ polypeptide consisting of an amino acid sequence set forth as ILLWEIFTX$_7$ (SEQ ID NO: 12)

wherein $X_7$ is a leucine (L). In some such embodiments, each polypeptide in the plurality of polypeptides is at least nine, at least ten, at least eleven or at least twelve amino acids in length.

The immunogenic TASA peptides can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Protein Delta Homolog 1 (DLK1)

In some embodiments, the methods disclosed herein utilize DLK1 protein, or a nucleic acid encoding DLK1 protein. An exemplary DLK1 protein is set forth as SEQ ID NO: 21, see also GENBANK® Accession No. NP_003827.3, incorporated herein by reference, and GENBANK® Accession No. NM_003836.5 (Sep. 23, 2012), incorporated herein by reference. In some embodiments, the DLK1 protein is at least about 80%, at least about 85%, at least about 90%, at least about 91%, at least about 92%, at least about 93%, at least about 94%, at least about 95%, at least about 96%, at least about 97%, at least about 98%, at least about 99% identical to SEQ ID NO: 21. Human DLK1 has very high homology with DLK1 from other animal species and therefore, the sequences of DLK1 from other organisms can be utilized, particularly where these sequences are identical, substantially homologous, and elicit an effective immune response against the target antigen (e.g., native DLK1 expressed by a cell). Additional exemplary DLK1 proteins include at most 10, at most 9, at most 8, at most 7, at most 6, at most 5, at most 4, at most 3, at most 2 or at most 1 conservative amino acid substitutions in SEQ ID NO: 21. The methods disclosed herein can utilize protein fragments of DLK1 protein, such as 100, 150, 200, 250, 300, 350 or 380 amino acids of a DLK1 protein.

In several embodiments, the isolated DLK1 protein or polypeptide is included in a fusion protein. Thus, the fusion protein can include the DLK1 protein or DLK1 polypeptide (see above) and a second heterologous moiety, such as a myc protein, an enzyme or a carrier (such as a hepatitis carrier protein or bovine serum albumin) covalently linked to the DLK1 protein or polypeptide. Thus, in several specific non-limiting examples, the fusion protein includes a DLK1 protein and six sequential histidine residues, a β-galactosidase amino acid sequence, and/or an immunoglobulin amino acid sequence. However, in other embodiments, the DLK1 is not fused to a heterologous moiety.

DLK1 proteins or polypeptides that are linked to a carrier are also of use in the disclosed methods. Generally, a carrier is an immunogenic macromolecule to which an antigenic molecule can be bound. When bound to a carrier, the bound DLK1 protein or DLK1 polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Suitable carriers include, but are not limited to, a hepatitis B small envelope protein HBsAg. This protein has the capacity to self-assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

In other embodiments, only the DLK1 protein or polypeptide is utilized. Thus, a second heterologous moiety is non-covalently linked to the DLK1 protein or polypeptide.

Nucleotides, Expression Vectors and Host Cells

Nucleic acids encoding one or more of the immunogenic TASA peptides, or encoding DLK1 protein, are provided. These polynucleotides include DNA, cDNA and RNA sequences which encode the polypeptide(s) of interest. Nucleic acid molecules encoding these peptides can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule, detectable marker or antibody sequence. An exemplary nucleic acid sequence encoding a DLK1 protein is provided in GENBANK® Accession No. NM_003836.5 (Sep. 23, 2012, incorporated herein by reference).

Nucleic acid sequences encoding one or more of the immunogenic TASA peptides can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20): 1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding one or more of the immunogenic TASA peptides can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Once the nucleic acids encoding one or more of the immunogenic TASA peptides are isolated and cloned, the protein can be expressed in a recombinantly engineered cell such as bacteria, plant, yeast, insect and mammalian cells using a suitable expression vector. One or more DNA sequences encoding one or more immunogenic TASA peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding one or more of the immunogenic TASA peptides, can be operatively linked to expression control sequences (e.g., a promoter). An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding one or more of the immunogenic TASA peptides can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding one or more of the immunogenic TASA peptides, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the one or more of the immunogenic TASA peptides (see for example, *Eukaryotic Viral Vectors*, Cold Spring Harbor Laboratory, Gluzman ed., 1982). One of skill in the art can readily use expression systems such as plasmids and vectors of use in producing proteins in cells including higher eukaryotic cells such as the COS, CHO, HeLa and myeloma cell lines.

In some embodiments, one or more polynucleotides encoding one or more immunogenic TASA peptides are included in one or more viral vectors. Examples of suitable viral vectors include retrovirus vectors, pox vectors, adenoviral vectors, herpes virus vectors, alpha virus vectors, baculovirus vectors, Sindbis virus vectors, vaccinia virus vectors and poliovirus vectors. Basic techniques for preparing recombinant DNA viruses containing a heterologous DNA sequence are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419).

Viral vectors can be prepared encoding one or more of the immunogenic TASA peptides. A number of viral vectors have been constructed, including polyoma, SV40 (Madzak et al., *J. Gen. Virol.,* 73:15331536, 1992), adenovirus (Berkner, *Cur. Top. Microbiol. Immunol.,* 158:39-6, 1992; Berliner et al., *Bio Techniques,* 6:616-629, 1988; Gorziglia et al., *J. Virol.,* 66:4407-4412, 1992; Quantin et al., *Proc. Nad. Acad. Sci. USA,* 89:2581-2584, 1992; Rosenfeld et al., *Cell,* 68:143-155 1992; Wilkinson et al., *Nucl. Acids Res.,* 20:2233-2239, 1992; Stratford-Perricaudet et al., *Hum. Gene Ther.,* 1:241-256, 1990), vaccinia virus (Mackett et al., *Biotechnology,* 24:495-499, 1991), adeno-associated virus (Muzyczka, *Curr. Top. Microbiol. Immunol.,* 158:91-123, 1992; On et al., *Gene,* 89:279-282, 1990), herpes viruses including HSV and EBV (Margolskee, *Curr. Top. Microbiol. Immunol.,* 158:67-90, 1992; Johnson et al., *J. Virol.,* 66:29522965, 1992; Fink et al., *Hum. Gene Ther.,* 3:11-19, 1992; Breakfield et al., *Mol. Neurobiol.,* 1:337-371, 1987; Fresse et al., *Biochem. Pharmacol.,* 40:2189-2199, 1990), Sindbis viruses (Herweijer et al., *Human Gene Therapy,* 6:1161-1167, 1995; U.S. Pat. Nos. 5,091,309 and 5,2217,879), alphaviruses (Schlesinger, *Trends Biotechnol.,* 11:18-22, 1993; Frolov et al., *Proc. Natl. Acad. Sci. USA,* 93:11371-11377, 1996) and retroviruses of avian (Brandyopadhyay et al., *Mol. Cell Biol.,* 4:749-754, 1984; Petropouplos et al., *J. Virol.*, 66:3391-3397, 1992), murine (Miller, *Curr. Top. Microbiol. Immunol.*, 158:1-24, 1992; Miller et al., *Mol. Cell Biol.*, 5:431-437, 1985; Sorge et al., *Mol. Cell Biol.*, 4:1730-1737, 1984; Mann et al., *J. Virol.*, 54:401-407, 1985), and human origin (Page et al., *J. Virol.*, 64:5370-5276, 1990; Buchschalcher et al., *J. Virol.*, 66:2731-2739, 1992). Baculovirus (*Autographa californica* multi-nuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Viral vectors that encode one or more immunogenic TASA peptides typically include at least expression control element (e.g., a promoter) operationally linked to the nucleic acid sequence encoding the one or more immunogenic TASA peptides. The at least on expression control element is inserted in the poxviral vector to control and regulate the expression of the nucleic acid sequence. Examples of expression control elements of use in these vectors include, but are not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the one or more immunogenic TASA peptides in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

In one embodiment, a composition is provided that includes a recombinant virus comprising a vaccinia virus genome or portions thereof and a nucleic acid sequence encoding one or more immunogenic TASA peptides, and a recombinant virus comprising a nucleic acid sequence encoding an immunostimulatory molecule (for example, B 7-1 or B7-2). In such embodiments, any combination of encoding one or more immunogenic TASA peptides can be used, such as 2, 3, 4, 5, 6, 7 or more polynucleotides.

Isolation and purification of recombinantly expressed polypeptide can be carried out by conventional means including preparative chromatography and immunological separations. Once expressed, the one or more of the immunogenic TASA peptides can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Therapeutic Methods and Pharmaceutical Compositions

The immunogenic TASA peptides disclosed herein (including a plurality of immunogenic peptides), or nucleic acids encoding the immunogenic TASA peptides (including a plurality of nucleic acids), polynucleotides encoding such peptides and vectors comprising the polynucleotides, can be used in methods of generating an immune response, treating a subject with cancer and decreasing the growth of a tumor associated stromal cell, as described below. In several examples, the subject has a tumor or tumor microenvironment (TME) that expresses one or more TASAs.

In several embodiments, the methods include administering to a subject with a tumor a therapeutically effective amount of one or more of the immunogenic TASA peptides (for example, a plurality of immunogenic TASA peptides as described herein or one or more polynucleotides encoding these peptides), in order to generate an immune response.

The methods can include selecting a subject in need of treatment, such as a subject with a tumor, for example a tumor that expresses a TASA, or a TME that expresses a TASA. In several examples, the methods include selecting a subject with colorectal cancer or melanoma.

It is also disclosed herein that DLK1 protein, or a nucleic acid encoding DLK1 protein, can be used to treat a tumor and/or pathogenic angiogenesis. In several embodiments, the methods include administering to a subject with a tumor a therapeutically effective amount of one or more of the immunogenic DLK1 peptides (for example, a plurality of DLK1 peptides as described herein), one or more polynucleotides encoding these peptides, DLK1 protein, or a nucleic acid encoding DLK1, in order to generate an immune response. In some examples, the methods disclosed herein decrease pathological angiogenesis in the subject, to slow or inhibit the growth or metastasis of a tumor. In these applications, a therapeutically effective amount of a composition including the polypeptide, plurality of polypeptides, or polynucleotide is administered to a subject, thereby slowing or inhibiting the growth or the metastasis of a tumor, or other pathological angiogenesis, or to inhibit a sign or a symptom. Examples of suitable subjects include those diagnosed with or suspecting of having cancer (for example, a subject having a tumor), for example subjects having a carcinoma, such as a breast carcinoma, lung carcinoma, colorectal carcinoma, renal carcinoma, or melanoma. In additional examples, subject has a hematologic tumor, such as a hemangioma, lymphangioma, Kaposi sarcoma, or hemangioblastoma. In some examples, the tumor cells express DLK1. However, in some embodiments, the tumor cells do not express DLK1, but the pericytes in the blood vessels within the tumor express DLK1. In yet other examples, both the tumor cells and the pericytes in the blood vessels in the tumor express DLK1.

In some embodiments, compositions are administered to a subject having a disease such as cancer (for example, renal cell cancer), in an amount sufficient to reduce vascularization. Administration inhibits blood vessel growth, and/or normalizes the vasculature. Amounts effective for this use will depend upon the vascularization of the cancer, the general state of the patient's health, and the robustness of the patient's immune system. In one example, a therapeutically effective amount of the composition is that which provides either subjective relief of a symptom(s) or an objectively identifiable improvement, such as a decrease in vascularization, as noted by the clinician or other qualified observer. In some embodiments, these methods include administering to the subject one or more DLK polypeptides or DLK1 protein as disclosed herein.

In exemplary applications, compositions are administered to a subject having a disease, such as cancer (for example, colorectal cancer or melanoma), in an amount sufficient to raise an immune response to TASA-expressing cells. Administration induces a sufficient immune response to slow the proliferation of such cells or to inhibit their growth, or to reduce a sign or a symptom of the tumor. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

One or more immunogenic TASA peptides or one or more polynucleotides encoding these peptides, DLK1 protein, or a polynucleotide encoding DLK1 protein can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, intraperitoneal or intravenous injection, but even oral, nasal, transdermal or anal administration is contemplated. In one embodiment, administration is by subcutaneous or intramuscular injection. To extend the time during which the peptide, protein or polynucleotide is available to stimulate a response, the peptide, protein or polynucleotide can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 41 BBL and ICAM-1 are administered.

In one specific, non-limiting example, one or more immunogenic TASA peptides (for example, a plurality of such peptides as described herein), or DLK1 protein, is administered in a manner to direct the immune response to a cellular response (that is, a cytotoxic T lymphocyte (CTL) response), rather than a humoral (antibody) response.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to one or more immunogenic TASA peptides, a MHC Class II-restricted T-helper epitope is added to the one or more immunogenic TASA peptides to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including one or more immunogenic TASA peptides or DLK1 protein is provided. In some examples, the composition includes a plurality of immunogenic TASA peptides as described herein. These compositions are used to generate an immune response, such as for immunotherapy. In one embodiment, one or more immunogenic TASA peptides are mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalane, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

In another embodiment, a pharmaceutical composition including one or more polynucleotides encoding one or more immunogenic TASA peptides, or encoding DLK1 protein, is provided. For example the composition can include one or more polynucleotides encoding a plurality of immunogenic TASA peptides as described herein. A therapeutically effective amount of polynucleotide can be administered to a subject in order to generate an immune response. In one specific, non-limiting example, a therapeutically effective amount of the polynucleotide is administered to a subject to treat colorectal cancer, hepatocellular carcinoma or melanoma.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J Sci. Am. 6(Suppl 1):561-6; Cao et al., 1998, Stem Cells 16(Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a viral vector. In various embodiments, the nucleic acid encoding the biological adjuvant can be cloned into same vector as an immunogenic TASA peptide coding sequence, or the nucleic acid can be cloned into one or more separate vectors for co-administration. In addition, nonspecific immunomodulating factors such as Bacillus Cahnette-Guerin (BCG) and levamisole can be co-administered.

One approach to administration of nucleic acids is direct immunization with plasmid DNA, such as with a mammalian expression plasmid. As described above, nucleotide sequence encoding immunogenic TASA peptides, or encoding DLK1 protein, can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, one or more immunogenic TASA peptides, or DLK1 protein, can also be expressed by attenuated viral hosts or vectors or bacterial vectors. Recombinant vaccinia virus, poxvirus, adeno-associated virus (AAV), herpes virus, retrovirus, or other viral vectors can be used to express one or more TASA peptides, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

A first recombinant virus, such as a poxvirus (for example, vaccinia virus) encoding one or more TASA immunogenic polypeptides can be used in conjunction with a second recombinant virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences (see U.S. Pat. No. 6,893,869, and U.S. Pat. No. 6,045,908, which are incorporated by reference herein).

When a viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more immunogenic TASA peptides (or DLK1 protein) to be administered is based on the titer of virus particles. An exemplary range of the immunogen to be administered is $10^5$ to $10^{10}$ virus particles per mammal, such as a human.

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and one or more immunogenic TASA peptides (or DLK1 protein) enhances the immune response. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with one or more TASA immunogenic polypeptides, a nucleic acid encoding one or more immunogenic TASA peptides, DLK1 protein or a nucleic acid encoding DLK1 protein. The co-expression of one or more immunogenic TASA peptides, DLK1 protein or a nucleic acid encoding DLK1 protein, together with at least one immunostimulatory molecule can be effective in an animal model to show anti-tumor effects.

In one embodiment, a nucleic acid encoding one or more immunogenic TASA peptides (or DLK1 protein) is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 µg to 10 mg of one or more immunogenic TASA peptides (or DLK1 protein) per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions are known or apparent to those skilled in the art and are described in more detail in such publications as *Remingtons Pharmaceutical Sciences, 19<sup>th</sup>* Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In another method, antigen presenting cells (APCs), such as dendritic cells, are pulsed or co-incubated with peptides comprising one or more immunogenic TASA peptides, or with DLK1 protein, or a nucleic acid encoding the peptide(s) or protein, in vitro. In one specific, non-limiting example, the antigen presenting cells can be autologous cells. A therapeutically effective amount of the antigen presenting cells can then be administered to a subject.

One or more immunogenic TASA peptides or DLK1 protein, or a nucleic acid encoding the peptide(s) or protein, can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of one or more immunogenic TASA peptides. One or more immunogenic TASA peptides (or DLK1 protein), or a nucleic acid encoding the peptide(s) or protein, can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present one or more immunogenic TASA peptides, such as DLK1 peptides. These dendritic cells are then administered alone (or in combination with another agent) to a subject with a tumor, for example a tumor that expresses the corresponding TASA, such as a colorectal tumor or melanoma.

Alternatively, the APCs are used to sensitize CD8 cells, such as tumor infiltrating lymphocytes (TILs) from tumors or peripheral blood lymphocytes (PBLs). The TILs or PBLs can be from the same subject (autologous) that is to be treated. Alternatively, the TILs or PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

The cells can be administered to a subject to inhibit the growth of TASA expressing cells in a tumor or TME. In these applications, a therapeutically effective amount of activated antigen presenting cells, or activated lymphocytes, are administered to a subject suffering from a disease, in an amount sufficient to raise an immune response to TASA expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as interleukin (IL)-2, IL-3, IL-6, IL-10, IL-12, IL-15, GM-CSF, or interferons.

The methods of treating a subject with a tumor described herein can be accompanied by administration of anti-cancer or anti-angiogenesis agents or therapeutic treatments (such as surgical resection of a tumor or radiation therapy). For example, the subject can receive additional therapies (a) prior to, during, or following administration of a therapeutic amount of one or more immunogenic TASA peptides, or (b) prior to, during, or following administration of a therapeutic amount of DLK1 protein or a nucleic acid encoding DLK1 protein. In one example, the subject receives one or more treatments to remove or reduce the tumor prior to administration of a therapeutic amount of one or more agents for treatment of the tumor. For example, the additional agent may include, but is not limited to, a chemotherapeutic agent, an anti-angiogenic agent, or a combination thereof. In another example, at least part of the tumor is surgically or otherwise excised or reduced in size or volume prior to administering the therapeutically effective amount of the antibody or conjugate. In some embodiments, the chemotherapeutic agent reduces suppressor cells in the tumor microenvironment or fosters the recruitment of vaccine-induced T cells into the tumor site. In some examples, the agent is bevacizumab, sunitinib, axitinib, HSP90 inhibitors, or gencitabine/fludarabine.

Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, gene regulators, angiogenesis inhibitors. These agents (which are administered at a therapeutically effective amount) and treatments can be used alone or in combination. For example, any suitable anti-cancer or anti-angiogenic agent can be administered in combination with the immunogenic TASA peptides or DLK1 protein disclosed herein, or polynucleotides encoding such peptides or protein and viral vectors include these polynucleotides. Methods and therapeutic dosages of such agents are known to those skilled in the art, and can be determined by a skilled clinician.

Microtubule binding agent refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof. For example, in some embodiments the anti-angiogenesis agent is an antibody that specifically binds to VEGF (e.g., Avastin, Roche) or a VEGF receptor (e.g., a VEGFR2 antibody). In one example the anti-angiogenic agent includes a VEGFR2 antibody, or DMXAA (also known as Vadimezan or ASA404; available commercially, e.g., from Sigma Corp., St. Louis, Mo.) or both. The anti-angiogenic agent can be bevacizumab, sunitinib, an anti-angiogenic tyrosine kinase inhibitors (TKI), such as sunitinib, xitinib and dasatinib. These can be used individually or in any combination.

Exemplary kinase inhibitors include Gleevac, Iressa, and Tarceva, sunitinib, sorafenib, anitinib, and dasatinib that prevent phosphorylation and activation of growth factors. Antibodies that can be used include Herceptin and Avastin that block growth factors and the angiogenic pathway. These can be used individually or in combination.

In some examples, the additional agent is a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof. Further examples include one or more additional vaccines targeting tumor antigens or tumor stem cells (such as a tumor initiating cell). The skilled artisan is familiar with such vaccines.

Reagents for the Detection of CD8+ cells that Specifically Bind TASAs

Reagents are provided herein for the detection of CD8 expressing cells that specifically bind the TASAs described herein. These reagents are tetrameric MHC Class I/immunogenic TASA peptide complexes. These tetrameric complexes include an immunogenic TASA peptide that includes at most twelve consecutive amino acids, wherein the isolated polypeptide comprises the amino acid sequence as shown in Table 1. Specific examples of immunogenic TASA peptides that are nine or ten amino acids in length are disclosed above.

Tetrameric MHC Class I/peptide complexes can be synthesized using methods well known in the art (Altmann et al., *Science* 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the trans-membrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with streptavidin.

In one embodiment, the streptavidin is labeled. Suitable labels include, but are not limited to, enzymes, magnetic beads, colloidal magnetic beads, haptens, fluorochromes, metal compounds, radioactive compounds or drugs. The enzymes that can be conjugated to streptavidin include, but are not limited to, alkaline phosphatase, peroxidase, urease and β-galactosidase. The fluorochromes that can be conjugated to the streptavidin include, but are not limited to, fluorescein isothiocyanate, tetramethylrhodamine isothiocyanate, phycoerythrin, allophycocyanins and Texas Red. For additional fluorochromes that can be conjugated to streptavidin, see Haugland, R. P., *Molecular Probes: Handbook of Fluorescent Probes and Research Chemicals* (1992-1994). The metal compounds that can be conjugated to the streptavidin include, but are not limited to, ferritin, colloidal gold, and particularly, colloidal superparamagnetic beads. The haptens that can be conjugated to the streptavidin include, but are not limited to, biotin, digoxigenin, oxazalone, and nitrophenol. The radioactive compounds that can be conjugated to streptavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, streptavidin labeled with a fluorochrome is utilized in the methods disclosed herein.

In one embodiment, suspension of cells including T cells that specifically recognize one or more TASAs is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

EXAMPLES

The following examples are provided to illustrate certain particular features and/or embodiments and should not be construed as limiting.

Example 1

Intratumoral Gene Therapy Induces Cross-Priming of T Cells Reactive Against Tumor-Associated Stromal Antigens This example illustrates that cross-priming of CD8+ T cells reactive against TASA is a general paradigm for effective immunotherapy. The results show that protective CD8+ T cells induced as a consequence of effective intratumoral DC.IL12 therapy recognize both tumor-associated stromal cells (i.e. flow-sorted pericytes and VEC) and naturally-processed and HLA-A2-presented peptides derived from TASA. These data illustrate the therapeutic targeting of TASA (via intratumoral cytokine gene therapy or specific vaccination) as a means to treat vascularized solid tumors.

Materials and Methods

Mice.

HHD mice fail to express H-$2^b$ class I molecules, with their cells instead expressing an HLA-A*0201-hβ2 microglobulin single-chain (HHD) gene product (Firat et al., *Int Immunol.*, 14:925-934, 2002). Ag-specific CD8+ T cell responses in HHD mice recapitulate those observed in HLA-A2+ human donors (Firat et al., *Int Immunol.*, 14:925-934, 2002). Female 6-8 week old mice were used in all experiments and were handled in accordance with an Institutional Animal Care and Use Committee (IACUC)-approved protocol. HLA-A2 expression on peripheral blood cells isolated from HHD mice via tail venipuncture was confirmed by coordinate positive staining as assessed by flow cytometry using two monoclonal antibodies (mAbs) MA2.1 (reactive against HLA-A2 and HLA-B17) and BB7.2 (reactive against HLA-A2 and HLA-Aw69) (both monoclonal antibodies from the American Type Culture collection; ATCC, Manassas, Va.).

Cell Lines and Culture.

B16 is an HLA-A$2^{neg}$, mMART-1+, mgp100+ melanoma cell line (syngenic to the H-$2^b$ background of HHD mice) known in the art (Hatano et al., *J Transl Med.*, 2:40, 2004). The T2 cell line is an HLA-A2+, TAP-deficient human T-cell/B-cell hybridoma (Tatsumi et al., *Cancer Res.*; 63:4481-4489, 2003). Cell lines were free of mycoplasma contamination and were maintained in CM (RPMI 1640 supplemented with 10% heat-inactivated fetal bovine serum, 100 U/ml penicillin, 100 µg/ml streptomycin, and 10 mM L-glutamine (all reagents from Life Technologies, Inc., Grand Island, N.Y.)) in a humidified incubator at 5% $CO_2$ and 37° C.

RT-PCR.

Reverse transcriptase-PCR (RT-PCR) was performed using the primer pairs shown in Table 2. Cycling times and temperatures were as follows: initial denaturation at 94° C. for 2 min (1 cycle), denaturation at 94° C. for 30 sec, annealing at 60° C. for 30 sec and elongation at 72° C. for 1 min (30 cycles), final extension at 72° C. for 5 min (1 cycle). PCR products were identified by image analysis software for gel documentation (LabWorks 4.6 Software; UVP, Upland, Calif.) following electrophoresis on 1.2% agarose gels and staining with ethidium bromide (Sigma-Aldrich).

TABLE 2

RT-PCR primers.

| Target | RT-PCR primers | Product (bp) |
|---|---|---|
| CD31 | Forward 5'-3': AGCCCACCAGAGACATGGAA (SEQ ID NO: 33)<br>Reverse 5'-3': CTGGCTCTGTTGGAGGCTGT (SEQ ID NO: 34) | 337 |
| DLK1 | Forward 5'-3': CTGCACACCTGGGTTCTCTG (SEQ ID NO: 35)<br>Reverse 5'-3': GCATGGGTTAGGGGTACAGC (SEQ ID NO: 36) | 202 |
| EphA2 | Forward 5'-3': GGGGATGCCAACAGCTATAA (SEQ ID NO: 37)<br>Reverse 5'-3': CTCCTGCCAGTACCAGAAGC (SEQ ID NO: 38) | 232 |
| gp100 | Forward 5'-3': CATCAATGGGAGCCAGGTGT (SEQ ID NO: 39)<br>Reverse 5'-3': TGAAGGTTGAACTGGCGTGA (SEQ ID NO: 40) | 296 |
| HBB | Forward 5'-3': TCAGAAACAGACATCATGGTGC (SEQ ID NO: 41)<br>Reverse 5'-3': TAGACAATAGCAGAAAAGGGGC (SEQ ID NO: 42) | 480 |
| NG2 | Forward 5'-3': ACAGACGCCTTTGTTCTGCT (SEQ ID NO: 43)<br>Reverse 5'-3': TCGGAAGAAATGTCCAGGAG (SEQ ID NO: 44) | 399 |
| NRP1 | Forward 5'-3': TCCAAGTGGACCTGGGAGAT (SEQ ID NO: 45)<br>Reverse 5'-3': TTCACAGCCCAGTAGCTCCA (SEQ ID NO: 46) | 299 |
| NRP2 | Forward 5'-3': CCGGAAGAGACCTGTGGTTG (SEQ ID NO: 47)<br>Reverse 5'-3': CCGATCGTCCCTTCCCTATC (SEQ ID NO: 48) | 394 |
| PDGFRβ | Forward 5'-3': TGCTCCTGGAGAGGCTTCTG (SEQ ID NO: 49)<br>Reverse 5'-3': GGAGGAAGTGTTGACTTCATTC (SEQ ID NO: 50) | 301 |
| PSMA | Forward 5'-3': CCTGCGGTGAAGTCCTATCC (SEQ ID NO: 51)<br>Reverse 5'-3': GTTTCCAGCAAAGCCAGGTC (SEQ ID NO: 52) | 300 |
| RGS5 | Forward 5'-3': AAGTTGGGAATTCTCCTCCAG (SEQ ID NO: 53)<br>Reverse 5'-3': TTCCTCACTGAATTCAGACTTC (SEQ ID NO: 54) | 203 |
| TEM1 | Forward 5'-3': TTCACCAACTGGGCCCAGC (SEQ ID NO: 55)<br>Reverse 5'-3': GTTGACACACATCTGCTGGC (SEQ ID NO: 56) | 645 |
| VEGFR1 | Forward 5'-3': CCAACTACCTCAAGAGCAAAC (SEQ ID NO: 57)<br>Reverse 5'-3': CCAGGTCCCGATGAATGCAC (SEQ ID NO: 58) | 318 |
| VEGFR2 | Forward 5'-3': ACAGACAGTGGGATGGTCC (SEQ ID NO: 59)<br>Reverse 5'-3': AAACAGGAGGTGAGCGCAG (SEQ ID NO: 60) | 271 |
| β-actin | Forward 5'-3': GGCATCGTGATGGACTCCG (SEQ ID NO: 61)<br>Reverse 5'-3': GCTGGAAGGTGGACAGCGA (SEQ ID NO: 62) | 615 |

Fluorescence Imaging of Tumor Sections.

Tumor tissue samples were prepared and sectioned as previously described (Komita et al., *Cancer Res.*, 68: 8076-8084, 2008). For analysis of T cell subsets, sections were incubated with rabbit anti-mouse NG2 (Millipore, Bedford, Mass.)

along with alexa488-conjugated anti-CD4 or -CD8β antibodies or matching isotype controls (all from BD Biosciences, San Jose, Calif.) for 1 h. After washing with 0.5% BSA in PBS, sections were stained with donkey anti-rabbit Ig cy5 (Jackson ImmunoResearch, West Grove, Pa.) secondary antibody for one hour at room temperature. For analysis of CD31 vs. NG2, sections were first incubated with rat anti-mouse CD31 (BD Biosciences) and rabbit anti-mouse NG2 (Millipore) antibodies for one hour at room temperature and then washed. Sections were then treated with donkey anti-rat Ig cy3 and donkey anti-rabbit Ig cy5 (both from Jackson ImmunoResearch) antibodies for 1 hr and washed. For the analysis of target antigens in B16 tumor lesions, all sections received dilutions of rat anti-mouse CD31 (BD Biosciences) and guinea pig anti-mouse NG2 (Burg et al. *Cancer Res.*, 59:2869-2874, 1999) antibodies. In addition, each slide received an antibody reactive against a given TASA: rabbit anti-mouse antibody for DLK1 (R&D Systems, Minneapolis, Minn.), EphA2 (Santa Cruz Biotech., San Diego, Calif.), PSMA (Thermo Fisher Scientific, Rockford, Ill.), RGS5 (Sigma-Aldrich), VEGFR1 (Thermo Fisher Scientific) or goat anti-mouse antibody for HBB (Santa Cruz), NRP1 (R&D Systems), NRP2 (R&D Systems), PDGFRβ (R&D Systems), VEGFR2 (Abcam, Cambridge, Mass.). Sections were then again washed five times with 0.5% BSA (in PBS), before a one hour incubation with dilutions of a mixture of secondary antibodies: i.) donkey anti-rat cy5 antibody, ii.) donkey anti-guinea pig DyLight 488 antibody, and iii.) either donkey anti-rabbit cy3 antibody or donkey anti-goat cy3 antibody depending on the species of antibody directed against the TASA target (all secondary antibodies were purchased from Jackson ImmunoResearch). After secondary Ab staining, sections were then washed with 3 washes of PBS, coverslipped with gelvatol mounting media (made in-house) and stored at 4° C. until imaging using an Olympus Fluoview 500 Confocal microscope (Olympus America, Center Valley, Pa.).

Synthetic Peptides.

The peptides shown in Table 4 were synthesized by 9-fluorenylmethoxycarbonyl (Fmoc) chemistry. Peptides were >96% pure based on high performance liquid chromatography profile and mass spectrometric analysis.

Generation of HHD Bone Marrow (BM)-Derived DCs and DC.IL12.

DC were generated from BM precursors isolated from the tibias/femurs of mice using in vitro cultures containing 1000 U/ml recombinant murine granulocyte/macrophage colony-stimulating factor (rmGM-CSF) and 1000 U/ml rmIL-4 (both from Peprotech, Rocky Hill, N.J.), as previously described (Komita et al., *Cancer Res*, 68: 8076-8084, 2008). The Ad.mIL-12p70 and Ad.ψ5 (empty) recombinant adenoviral vectors were produced as reported previously (Komita et al., *Cancer Res*, 68: 8076-8084, 2008; Tatsumi et al., *Cancer Res.*, 63: 6378-6386, 2003). Five million (day 5 cultured) DCs were infected at an MOI=50 with Ad.m1L-12p70 or the control, empty vector Ad.ψ5. While control DC produced <62.5 pg IL-12p70/ml/48 h/$10^6$ cells, DC.IL12 cells produced 1-10 ng IL-12p70/ml/48 h/$10^6$ cells (Komita et al., *Cancer Res.*; 68:8076-8084, 2008; Tatsumi et al., *Cancer Res.*, 63:6378-6386, 2003).

Intratumoral (I.t.) DC.IL12 Therapy.

B16 melanoma cells ($1\times10^5$) were injected subcutaneously in the right flank of HHD mice and allowed to establish for 7 days. Mice were then randomized into cohorts of 5 animals, with each cohort exhibiting an approximate mean tumor size of 30-50 $mm^2$. On days 7 and 14, tumor-bearing mice were untreated or treated with intratumoral injections of $1\times10^6$ adenovirus-infected dendritic cells (DC.ψ5 or DC.IL12) in a total volume of 50 μL PBS. Tumor size was then assessed every 3 to 4 days and recorded in $mm^2$, determined as the product of orthogonal measurements taken using vernier calipers. In some experiments, as indicated, in vivo antibody depletions (on days 6, 13 and 20 post-tumor injection) of $CD4^+$ T cells or $CD8^+$ T cells were performed as previously described (13). Data were reported as mean tumor area ±SD. On day 17-19 post-tumor inoculation, $CD8^+$ splenocytes and TIL were MACS-isolated from 3 mice/cohort, with cells pooled and assessed for reactivity against peptide epitopes or cell targets (pericytes, VEC, tumor cells).

Evaluation of Murine $CD8^+$ T Cell Responses In Vitro.

To analyze Ag-specific responses, spleens and TIL were harvested (from 2 mice/group) 3-5 days after the second intratumoral injection of control DC or DC.IL12 (i.e. day 17-19 after tumor inoculation). Splenic lymphocytes were restimulated in vitro for 5 days with irradiated (2.5 Gy) naïve peptide-pulsed HHD splenocytes at a stimulator:responder cell ratio of 1:1. Responder $CD8^+$ T cells were then isolated using magnetic bead cell sorting (MACS; Miltenyi Biotec) and analyzed for reactivity against unpulsed or peptide-pulsed T2 cells, as indicated. To analyze T cell response to stromal cell targets and tumor cells, untreated HHD mice bearing established day 17-19 B16 tumors were sacrificed and tumors and kidneys removed. Tissues were then minced manually and enzymatically digested as described by Crisan et al. (Crisan et al., *Cell Stem Cell.*, 3:301-313, 2008) using collagenases IA, II, and IV (Sigma-Aldrich) and DNAse I (Sigma-Aldrich) for 30 min at 37° C., with gentle shaking. Cells were then being passed through a 70 micron cell strainer (BD-Biosciences), washed with PBS, and single cell suspensions stained with anti-mouse CD31 FITC (BD-Biosciences), anti-mouse CD140b (PDGFRβ) PE (eBioscience), and anti-mouse H2-$K^b$ APC (BD-Biosciences). After washing with PBS, cells were sorted into enriched populations containing pericytes (PDGFRβ$^+$CD31$^{neg}$H-2$K^{b(neg)}$) or VEC (PDGFRβ$^{neg}$CD31$^+$H-2$K^{b(neg)}$) using a multicolor fluorescence-activated cell sorter (FACSAria, BD-Biosciences). In all cases, cells were >95% pure for the stated phenotype. $CD8^+$ T cells ($10^5$) were then co-cultured with $10^4$ pericytes or VEC in U-bottom 96-well plates (Sigma-Aldrich). To verify HLA-A2 restricted recognition of target cells by $CD8^+$ T cells, 10 μg of anti-HLA-A2 mAb BB7.2 or control anti-HLA-class II mAb L243 (both from ATCC) were added to replicate co-culture wells. Forty-eight hours after initiating splenic $CD8^+$ T cell co-cultures, cell-free supernatants were collected and analyzed for mIFN-γ content using a commercial ELISA (BD-Biosciences) with a lower limit of detection of 31.3 pg/ml. Data were reported as the mean±SD of triplicate determinations. Alternatively, freshly-sorted $CD8^+$ TIL were co-cultured with pericytes, VEC, T2 cells (+/−peptides) or B16 tumor cells at a T cell-to-target cell ratio of 3:2 for 4-5 h at 37° C. and analyzed for intracellular levels of IFN-γ or cell-surface expression of CD107a/b using specific monoclonal antibodies (APC-labeled anti-mouse CD8α from eBioscience; PE-labeled rat anti-mouse IFN-γ and FITC-labeled rat anti-mouse CD107a/b from BD Biosciences) and flow cytometry using the manufacturer's suggested protocol and ref. (Mittendorf et al., *Breast Cancer Res Treat.*, 92:85-93, 2005), respectively.

In Vitro Assessment of Human $CD8^+$ T Cell Responses Against TASA- or TAA-Derived Peptides.

Peripheral blood mononuclear cells (PBMC) were obtained by venipuncture or leukapheresis from HLA-A2$^+$ normal donors or HLA-A2$^+$ melanoma patients with written consent under IRB-approved protocols (Table 3). $CD8^+$ T cells were then isolated by MACS (Miltenyi Biotec, Auburn, Calif.) and either not stimulated or stimulated with autologous, TASA peptide-pulsed DC as previously described (Tatsumi et al., Cancer Res., 63:4481-4489, 2003). Normal donor T cells were stimulated with TASA peptide-pulsed DC twice on a weekly schedule, with responder T cells harvested for analysis of their specificity 5 days after the booster stimulation (i.e. day 12 of T cell-DC co-culture). Melanoma patient CD8$^+$ T cells were analyzed after a single round of stimulation with TASA peptide-pulsed, autologous DC (i.e. day 5 of T cell-DC co-culture) as indicated. For DC-based stimulations, DC were pulsed with an equimolar (1 µM each) pool of the TASA peptides (Table 4) for 4 h at 37° C. at 5% $CO_2$ tension. These antigen-loaded DC were then used to stimulate autologous CD8$^+$ T cells at a T cell-to-DC ratio of 10:1 to generate a bulk population of responder T cells. T cells were maintained in IMDM media supplemented with 10% human AB serum, 100 U/ml penicillin, 100 mg/ml streptomycin, 10 mM L-glutamine and MEM non-essential amino acids (all reagents from Invitrogen, except human AB serum that was purchased from Sigma-Aldrich, St. Louis, Mo.). Responder CD8$^+$ T cells were analyzed for reactivity against control (HLA-A2$^+$) T2 cells or T2 cells pulsed with individual TASA or TAA peptides (1 µM for 4 h at 37° C.) at a CD8$^+$ T cell-to-T2 cell ratio of 5:1 for 24 h. Harvested cell-free supernatants were consequently assessed for hIFN-γ content using a specific ELISA (BD Biosciences, San Diego, Calif.) with a lower detection limit of 4.7 pg/ml.

Statistical Analysis.

Student's two-sided t-test and one-way ANOVA were used to test for overall differences between groups (StatMate III, ATMS Co., Tokyo, Japan), with a p value <0.05 taken as significant.

Results

Analysis of TASA Expression in the TME.

Figure 1A:
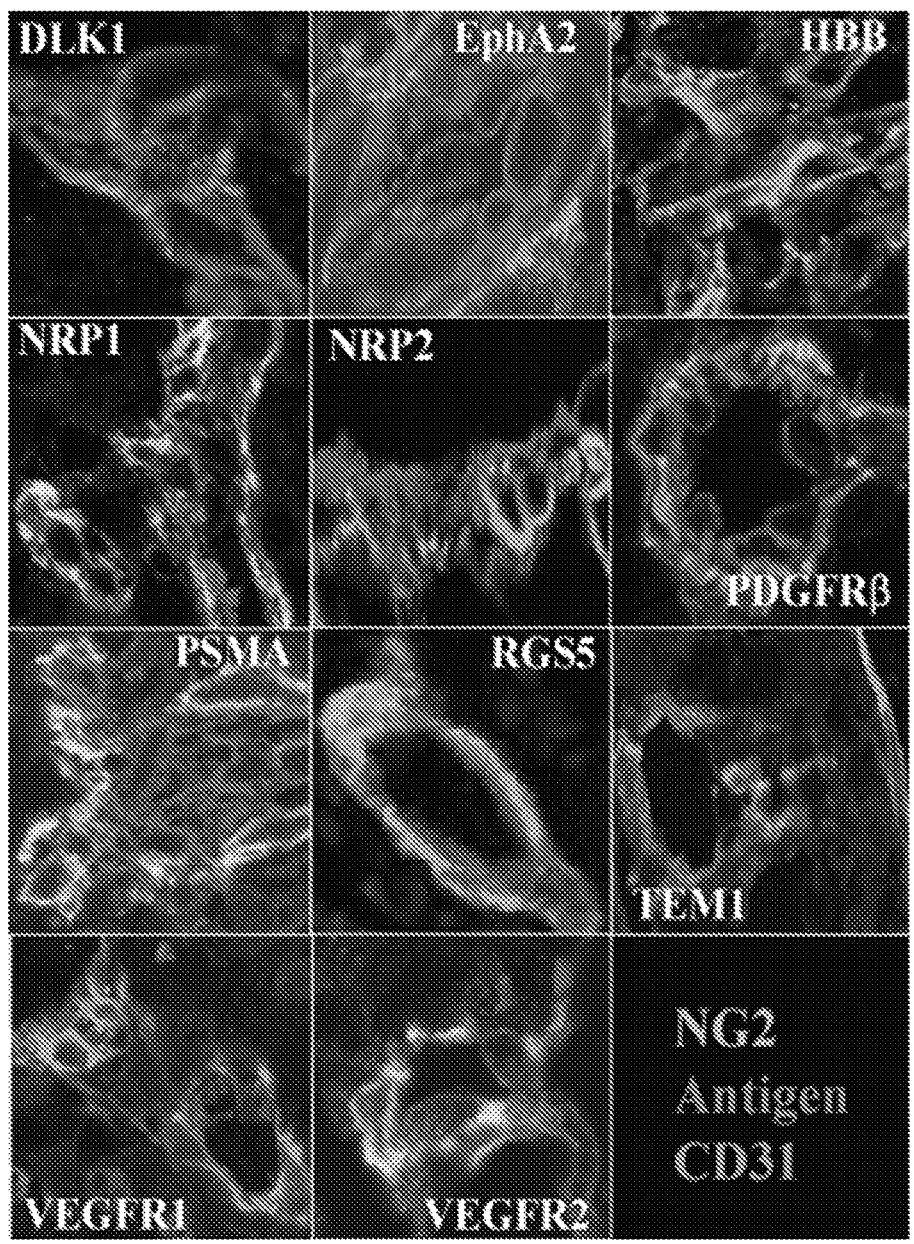
FIGS. 1A-1B show a series of digital images illustrating that expression of TASA in the established B16 tumor microenvironment (TME).
Figure 1B:
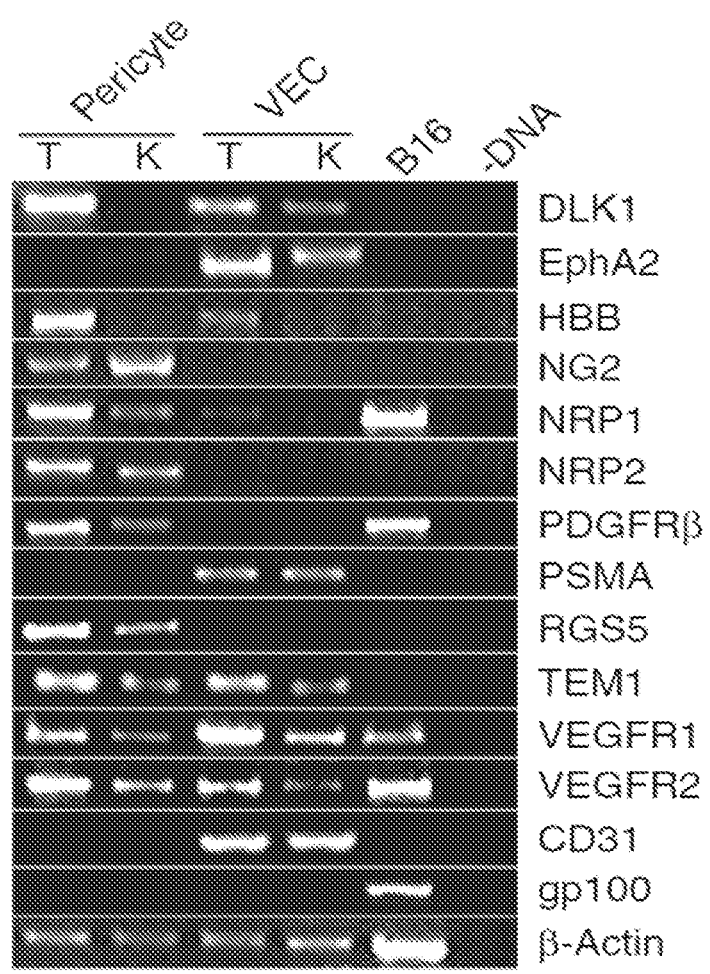

TASA are expressed by pericytes and/or activated VEC (Komita et al., Cancer Res., 68:8076-8084, 2008; Hatano et al., J Transl Med., 2:40, 2004; Maciag et al., Cancer Res., 68:8066-8075, 2008; Ishizaki et al., Clin Cancer Res., 12:5841-5849, 2006; Wada et al., Cancer Res., 65:4939-4946, 2005; Kaplan et al., Vaccine, 24: 6994-7002, 2006; Liu et al., Cytokine., 32:206-212, 2005; Silver et al., Clin Cancer Res., 3:81-85, 1997; Harada et al., Oncol Rep., 12:601-607, 2004; Bondjers et al., Am J Pathol., 162:721-729, 2003; Boss et al., Clin Cancer Res.; 13:3347-3355, 2007; Christian et al., Am J Pathol., 172:486-494, 2008). An initial panel of 12 antigens was selected for evaluation in the current studies (Table 4). To show that the chosen TASA were indeed expressed in situ by stromal cells in the TME, immunohistochemistry analyses were performed using specific antibodies on tissue sections isolated from day 14 (HLA-A2$^{neg}$) B16 melanomas growing progressively in untreated HLA-A2 Tg (HHD) mice. Using immunofluorescence microscopy, co-expression patterns of specific stromal target antigens were determined with NG2$^+$ pericytes and/or CD31$^+$ VEC within the TME. The resulting images are depicted in FIG. 1A, with a summary of cellular protein expression profiles provided in Table 3. Based on these imaging analyses, the DLK1, HBB, NG2, PDGFRβ, RGS5 and VEGFR2 antigens were assigned as predominantly tumor pericyte-associated, and the EphA2 and TEM1 antigens as predominantly tumor VEC-associated. The NRP1, NRP2, PSMA and VEGFR1 antigens appeared to be expressed by multiple cell types including pericytes, VEC and alternate stromal cells and/or tumor cells within the progressive B16 TME. To further corroborate TASA expression by NG2$^+$ pericytes, CD31$^+$ VEC or H-2K$^{b+}$ tumor cells within the TME, these cell populations were flow-sorted from enzymatically digested B16 tumors resected from untreated recipient HHD mice. To gauge potential overexpression of TASA in tumor versus normal tissues, pericytes and VEC were also flow-sorted from single cell digests of tumor-uninvolved kidneys harvested from these same animals. RT-PCR analyses were then performed on cDNA isolated from each of these sorted cell populations. Quality control analyses supported the expression of NG2 transcripts only in pericytes, CD31 transcripts only in VEC and gp100 transcripts only in B16 cells (FIG. 1B). These analyses also support: i.) tumor pericyte expression of all TASA transcripts with the exceptions of EphA2 and PSMA; ii.) tumor VEC expression of transcripts for DLK1, EphA2, HBB, PSMA, TEM1, VEGFR1 and VEGFR2; iii.) B16 expression of transcripts for NRP1, PDGFRβ, VEGFR1 and VEGFR2; iv.) higher levels of DLK1, EphA2, HBB, NRP1, NRP2, PDGFRβ, RGS5, TEM1, VEGFR1 and VEGFR2 transcript expression in tumor- versus normal kidney-derived stromal cells; and v.) comparable or greater levels of NG2, PSMA and CD31 transcript expression in normal kidney- versus tumor-derived stromal cells (FIG. 1B).

TABLE 3

Cells expressing TASA in the B16 TME.*

| TASA | Cells Expressing TASA Protein (IHC) | Cells Expressing TASA mRNA (RT-PCR) |
|---|---|---|
| DLK1 | P | P (Hi) > VEC (2.1) |
| EphA2 | VEC | VEC (3.3) |
| HBB | P | P (Hi) > VEC (Hi) |
| NG2 | P | P |
| NRP1 | P, VEC, T/S (Pericyte/VEC interface) | P (2.0), T > VEC |
| NRP2 | P, VEC (Intracellular) | P (1.6) |
| PDGFRβ | P > T/S | P (2.3), T |
| PSMA | VEC, P (Vesiculated, punctuate) | VEC |
| RGS5 | P > T/S (Cytoplasmic) | P (1.7) |
| TEM1 | T/S, VEC, P | P (1.5), VEC (1.6) |
| VEGFR1 | VEC, P, T/S (Intracellular/Nuclear) | VEC (1.8) > P (2.6), T |
| VEGFR2 | P > VEC, T/S | P (1.6) > VEC (4.5), T |

*Progressor B16 tumors (day 14) in untreated HHD mice were surgically-resected, then fixed, sectioned and stained using TASA-specific Abs, as described in FIG. 1A and the Materials and Methods. Based on co-localization of TASA with the NG2 and/or CD31 markers in fluorescence microscopy analyses, a pericyte (P)- and/or VEC- association was assigned with a given marker, respectively. In some cases, TASA were also expressed by NG2$^{neg}$, CD31$^{neg}$ cells (designated as T/S = tumor/stromal) in the TME, which could reflect either tumor cells or alternate stromal cell populations. RT-PCR analyses were performed on flow-sorted tumor-derived pericytes and VEC and tumor cells as described in FIG. 1B and the Materials and Methods. Numbers in parentheses reflect the fold increase in expression of transcripts in tumor versus normal kidney pericytes or VEC, as indicated, after first normalizing densitometry signals against β-actin in each case. (Hi) indicates the TASA transcript is expressed by tumor pericytes/VEC, but not normal kidney pericytes/VEC.

Selection of TASA Peptides for Immunologic Analyses.

Of the selected TASA, HLA-A2-presented epitopes recognized by CD8$^+$ T cells have been previously reported for human EphA2, NG2, PSMA, RGS5, VEGFR1 and VEGFR2 (Table 4). Notably, these defined human epitopes share 100% sequence identity with their murine homologues. To identify novel HLA-A2-presented epitopes in the alternate 6 selected TASA, a prediction algorithm (see, e.g., .bimas.cit.nih.gov/molbio/hla_bind/) was applied to each protein, and non-americ (9-mer) and/or decameric (10-mer) peptides were preferentially chosen for synthesis and corollary analyses based on 2 priority criteria: i.) a high algorithm predicted binding score to the HLA-A2.1 class I molecule, and ii.) identity in the human versus murine peptide sequences. This latter restriction was adopted for translational purposes; i.e. to insure that specific therapy-induced T cell responses would need to break operational tolerance in HLA-A2 Tg (HHD) recipient mice in order to provide anti-tumor protection (i.e. as would also need to occur for protection in HLA-A2$^+$ patients with solid cancers). After selection, each of the chosen synthetic peptides was shown to be competent (to a varying degree) to bind and stabilize HLA-A2 complexes expressed by T2 cells (FIG. 6), a prerequisite to their ability to be presented to specific, HLA-A2-restricted CD8+ T cells.

Figure 2A:
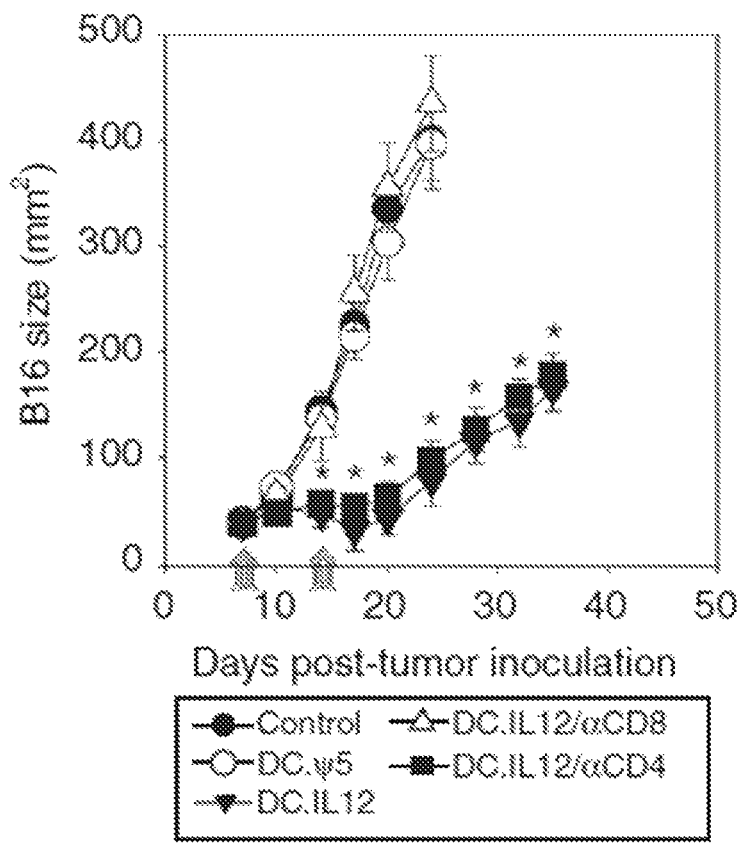
FIGS. 2A-2C show a series of graphs illustrating that induction of CD8$^+$ T cells reactive against TASA after intratumoral delivery of DC.IL12.
Figure 2B:
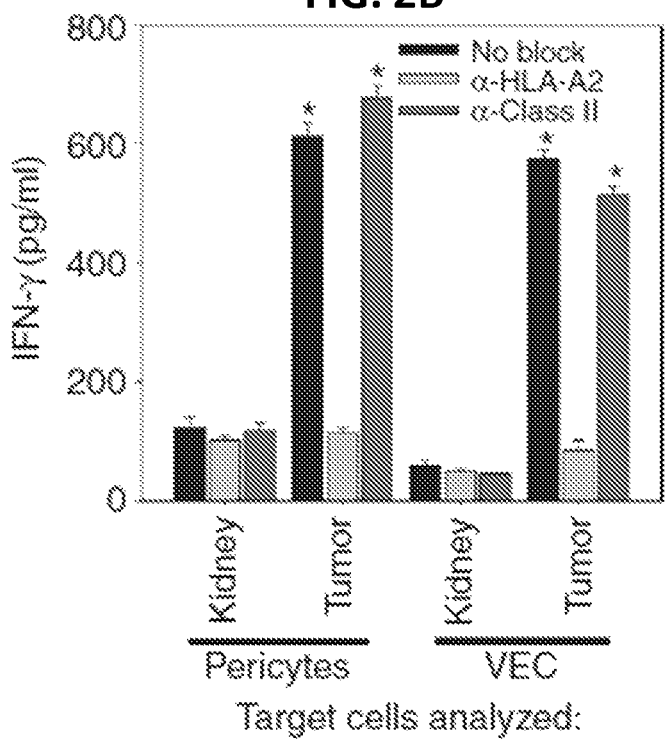
Figure 2C:
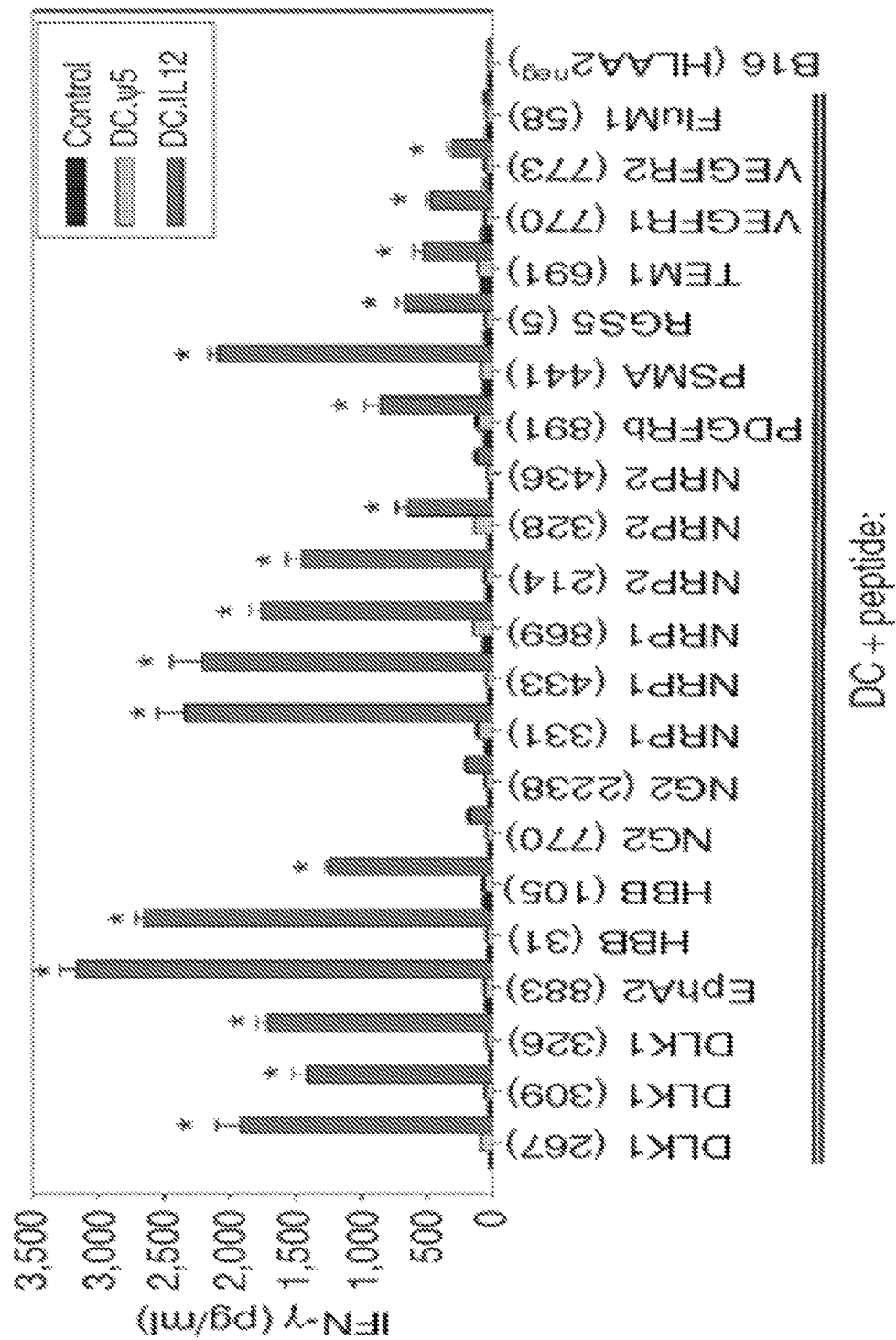
Figure 7:
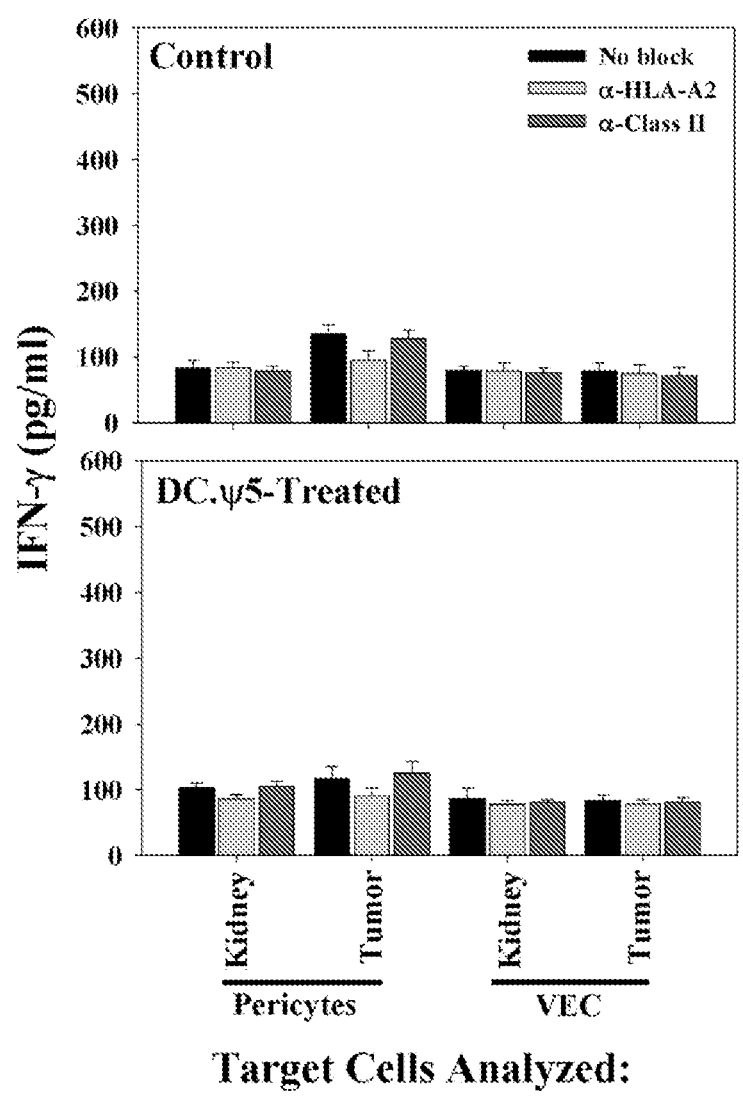
FIG. 7 shows a set of graphs illustrating that $CD8^+$ T cells isolated from B16-bearing HHD mice left untreated or treated with DC.ψ5 fail to recognize tumor-associated pericytes/VEC. $CD8^+$ T cells were MACS-isolated from the spleens of tumor-bearing animals that were left untreated (Control) or that were treated with intratumoral delivered DC.ψ5, as outlined in FIG. 2B. These T cells were then cultured with flow-sorted tumor- or kidney-derived pericytes or VEC+/−blocking anti-HLA-A2 (BB7.2) or class II (L243) antibodies. Cell-free supernatant was harvested after 24 hours incubation at 37° C. and analyzed using a specific IFN-γ ELISA. Representative data is presented from one of two independent experiments performed.

DC.ψ5)-treated cohort of animals directly recognized HLA-A2+ pericytes and VEC flow sorted from single-cell digests of B16 tumors (but not kidneys isolated from these same tumor-bearing animals) or HLA-A2$^{neg}$ B16 tumor cells (FIG. 2B, 2C and FIG. 7). Tc1 recognition of tumor-derived pericytes and

TABLE 4

Summary of in vitro results regarding TASA peptides.*

| TASA | AA Positions | Immunogenic Peptide Sequence | SEQ ID NO: | HLA-A2 Binding Score[b] | Specific CD8+ T Cell Response[a] | | |
|---|---|---|---|---|---|---|---|
| | | | | | HHD Mice Treated With i.t. DC.IL12 | HLA-A2+ Normal Donors (of 8) | HLA-A2+ Melanoma Patients (of 10) |
| DLK1 | 269-277 | RLTPGVHEL | 68 | 49 | + | 1 | 4 |
| | 310-318 | ILGVLTSLV | 2 | 118 | + | 2 | 6 |
| | 326-334 | FLNKCETWV | 3 | 1760 | + | 2 | 4 |
| EphA2[c] | 883-891 | TLADFDPRV | 10 | 1084 | + | 2 | 6 |
| HBB | 31-39 | RLLVVYPWT | 70 | 227 | + | 2 | 6 |
| | 105-114 | RLLGNVLVCV | 72 | 592 | + | 1 | 1 |
| NG2[d] | 770-778 | TLSNLSFPV | 83 | 403 | − | 0 | 4 |
| | 2238-2246 | LILPLLFYL | 14 | 1356 | − | 0 | 4 |
| NRP1 | 331-339 | GLLRFVTAV | 6 | 2249 | + | 2 | 7 |
| | 433-441 | GMLGMVSGL | 75 | 131 | + | 2 | 7 |
| | 869-877 | VLLGAVCGV | 8 | 1006 | + | 2 | 1 |
| NRP2 | 214-222 | DIWDGIPHV | 15 | 56 | + | 0 | 4 |
| | 328-336 | YLQVDLRFL | 16 | 249 | + | 0 | 4 |
| | 436-444 | NMLGMLSGL | 17 | 131 | − | 0 | 0 |
| PDGFRβ | 890-898 | ILLWEIFTL | 81 | 1792 | + | 2 | 1 |
| PSMA[e] | 441-450 | LLQERGVAYI | 18 | 920 | + | 0 | 2 |
| RGS5[f] | 5-13 | LAALPHSCL | 79 | 1 | + | 0 | 5 |
| TEM1 | 691-700 | LLVPTCVFLV | 76 | 1577 | + | 4 | 4 |
| VEGFR1[g] | 770-778 | TLFWLLLTL | 19 | 182 | + | 1 | 3 |
| VEGFR2[h] | 773-781 | VIAMFFWLL | 20 | 270 | + | 0 | 0 |

Figure 4:
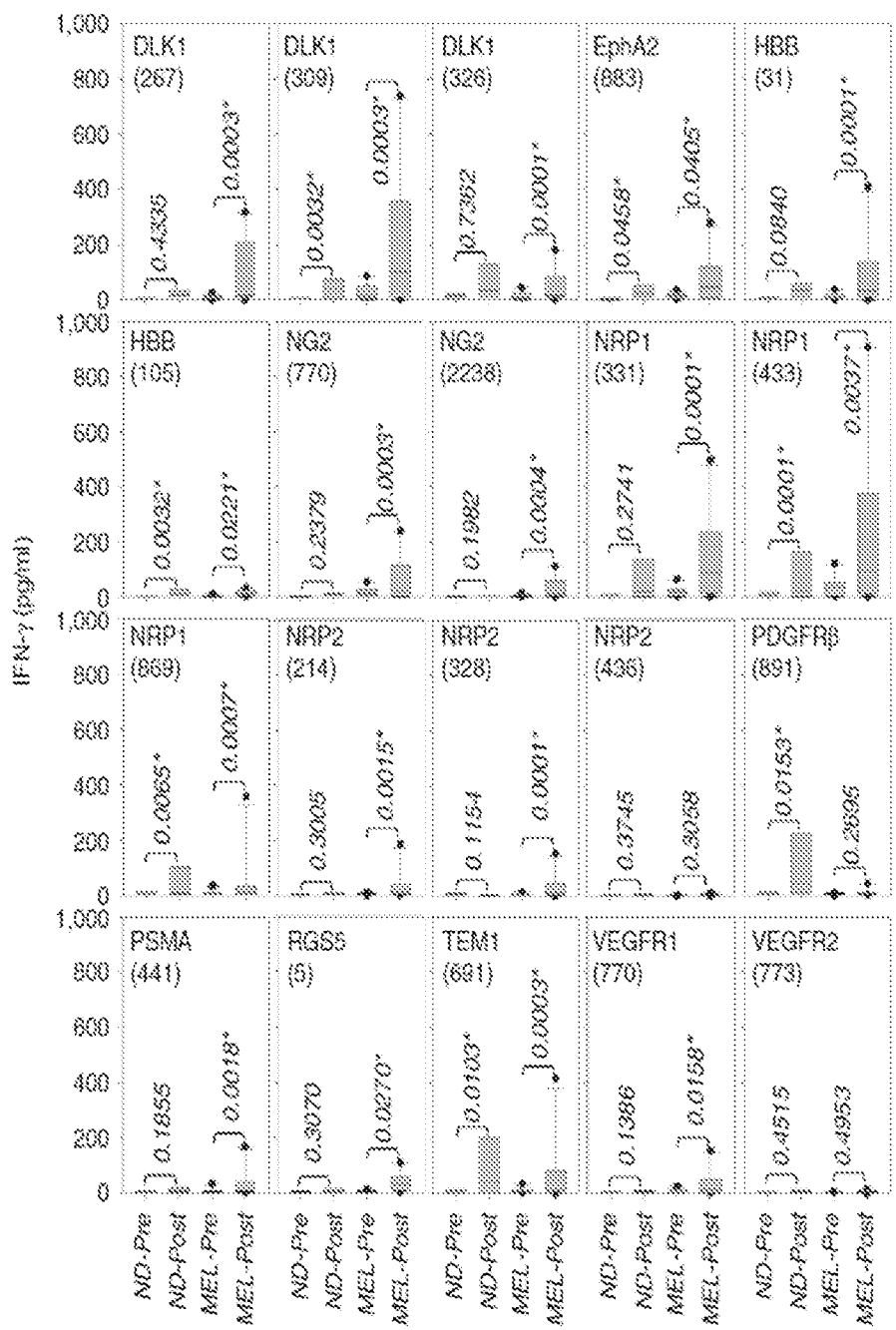
FIG. 4 shows a series of graphs illustrating the in vitro immunogenicity of TASA-derived peptides in $HLA-A2^+$ normal donors and patients with melanoma. The indicated peptides were pulsed onto autologous DC and used to prime and boost $CD8^+$ T cells isolated from the peripheral blood of eight normal $HLA-A2^+$ donors or ten $HLA-A2^+$ patients with melanoma. Seven days after the primary in vitro sensitization (IVS) (melanoma patients) or a secondary IVS boost (normal donors), T cells were analyzed for their reactivity against $HLA-A2^+$ T2 cells pulsed with the relevant peptide vs. the negative control HIV-$nef_{190-198}$ peptide. After 24 hours of co-culture, cell-free supernatants were analyzed for levels of secreted IFN-γ using a commercial ELISA. Data are reported in Bar and Whisker plots, with p-values provided for paired pre-versus post-IVS data from normal donors and patients. In addition, p<0.05 was detected for MEL-Post versus ND-Post for the following peptides: DLK1 (309), NG2 (770), NG2 (2238), PDGFRβ (891) and RGS5 (5).

*[a]CD8+ T cell response data is summarized for i.) HHD mice treated with DC.IL-12 gene therapy (as in FIG. 2C) or ii.) HLA-A2+ normal human donors and HLA-A2+ patients with melanoma as displayed pictorially in FIG. 4. Human (ELISA) responses were designated as + if CD8+ T cell reactivity against T2 cells presenting the indicated peptide (IFN-γ) was >30 pg/ml and more than 2 fold higher than reactivity versus T2 cells pulsed with the negative control HIV-nef$_{190-198}$ peptide (p < 0.05).
[b]Peptide sequences were submitted to an algorithm predicting binding to HLA-A2, with the deduced scores provided. A higher number reflects the prediction of a more stable HLA-A2-peptide complex.
[c](see Tatsumi et al., Cancer Res; 63: 4481-4489, 2003).
[d](see Maciag et al., Cancer Res., 68: 8066-8075, 2008).
[e](see Harada et al., Oncol.Rep., 12: 601-607, 2004).
[f](see Boss et al., Clin. Cancer Res., 13: 3347-3355, 2007).
[g](see Ishizaki et al., Clin. Cancer Res., 12: 5841-5849, 2006).
[h](see Wada et al., Cancer Res., 65: 4939-4946, 2005).

Delivery of DC.IL12 into HLA-A2$^{neg}$ B16 Tumors Promotes the Cross-Priming of CD8+ T Cells Reactive Against Tumor Pericytes, VEC and an Array of TASA-Derived Peptide Epitopes in HHD Mice.

DC.IL12 were prepared and injected directly into subcutaneous (HLA-A2$^{neg}$) B16 melanomas growing progressively in HLA-A2 Tg HHD mice on days 7 and 14 post-tumor inoculation. On day 19 post-tumor inoculation, the mice were euthanized and CD8+ splenic T cells were analyzed for their ability to secrete IFN-γ in response to stimulation with TASA-derived peptides presented by the HLA-A2+ T2 cell line.

Intratumoral delivery of DC.IL12 resulted in dramatically reduced tumor growth (FIG. 2A; p<0.05 versus vs. DC.ψ5-treated or untreated controls after day 11). Furthermore, splenic CD8+ T cells isolated from the DC.IL12 (but not VEC was completely blocked in the presence of the anti-HLA-A2 mAb BB7.2 (but not an anti-MHC II mAb L243), supporting the HLA-A2-restricted nature of T cell reactivity. Splenic CD8+ T cells from DC.IL12- (but not control DC-) treated animals also responded against an array of TASA-derived peptides when presented by HLA-A2+ T2 cells in vitro (FIG. 2C). A non-limiting explanation for ability of these murine (HHD) CD8+ T cells to recognize TASA-derived peptides in the context of the human T2 cell line is that these Tc1 effector cells exhibit moderate-to-high avidity for specific epitopes, since the murine CD8 co-receptor interacts inefficiently with the human HLA class I α3 domain (Kuball et al., Immunity, 22:117-129, 2005) expressed by T2 cells.

Figure 3A:
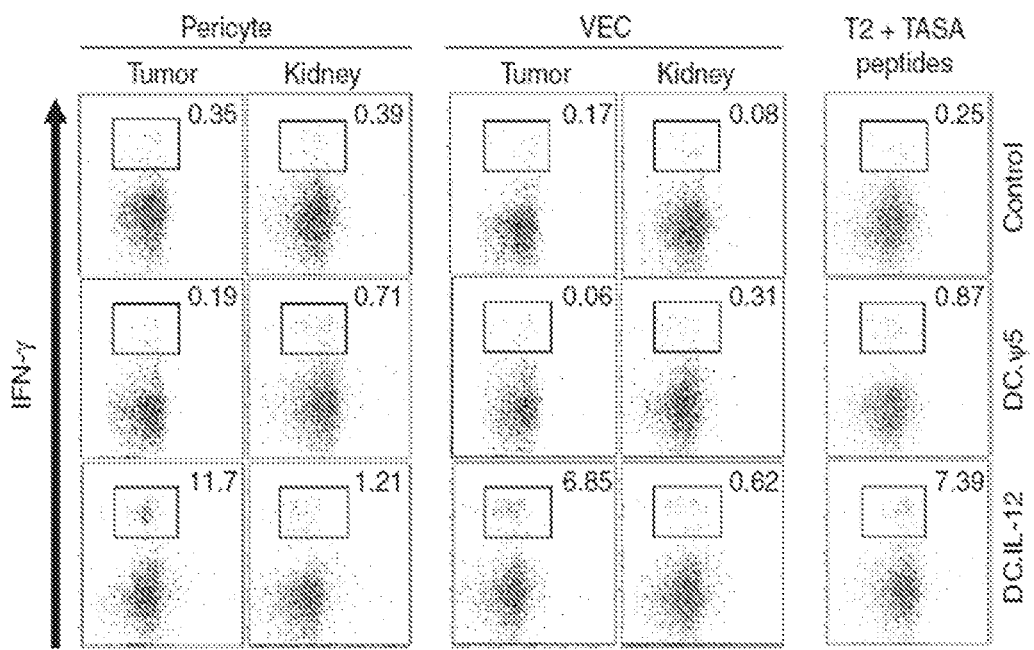
FIGS. 3A-3B show a series of scatter plot graphs illustrating that $CD8^+$ TIL from DC.IL12-treated mice are enriched in effector cells reactive against tumor pericytes and/or VEC, as well as TASA peptides. B16 tumor-bearing mice were treated as described in FIG. 2. On day 17 post-tumor inoculation, $CD8^+$ TIL were isolated from all cohorts of mice, and pericytes and VEC were isolated from the tumors and kidneys of untreated mice. Freshly-sorted $CD8^+$ TIL were then co-cultured with pericytes, VEC or T2 cells+/−TASA peptides (1 μM each of all peptides in Table 4 with the exception of NRP2- or PSMA-derived peptides) for 4-5 hours, before responder $CD8^+$ T cells were analyzed for intracellular expression of IFN-γ (FIG. 3A) or cell surface expression of CD107a/b (FIG. 3B) by flow cytometry. Inset numbers reflect the percentage of $CD8^+$ T cells expressing intracellular IFN-γ or cell surface CD107a/b. Data are from one representative experiment of two performed.
Figure 3B:
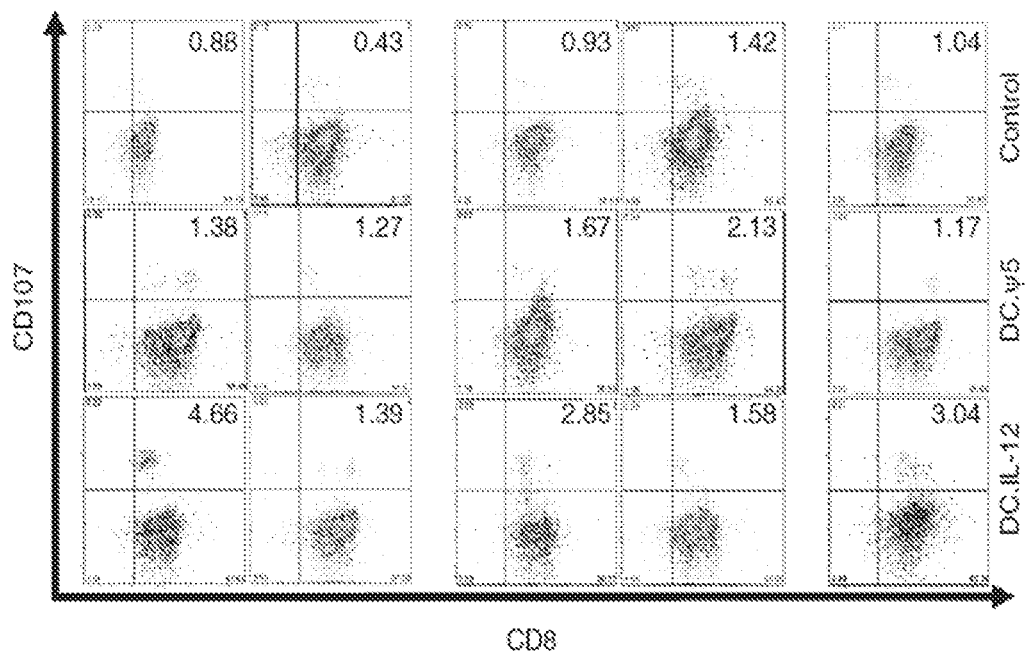
Figures 8A, 8B, 8C:
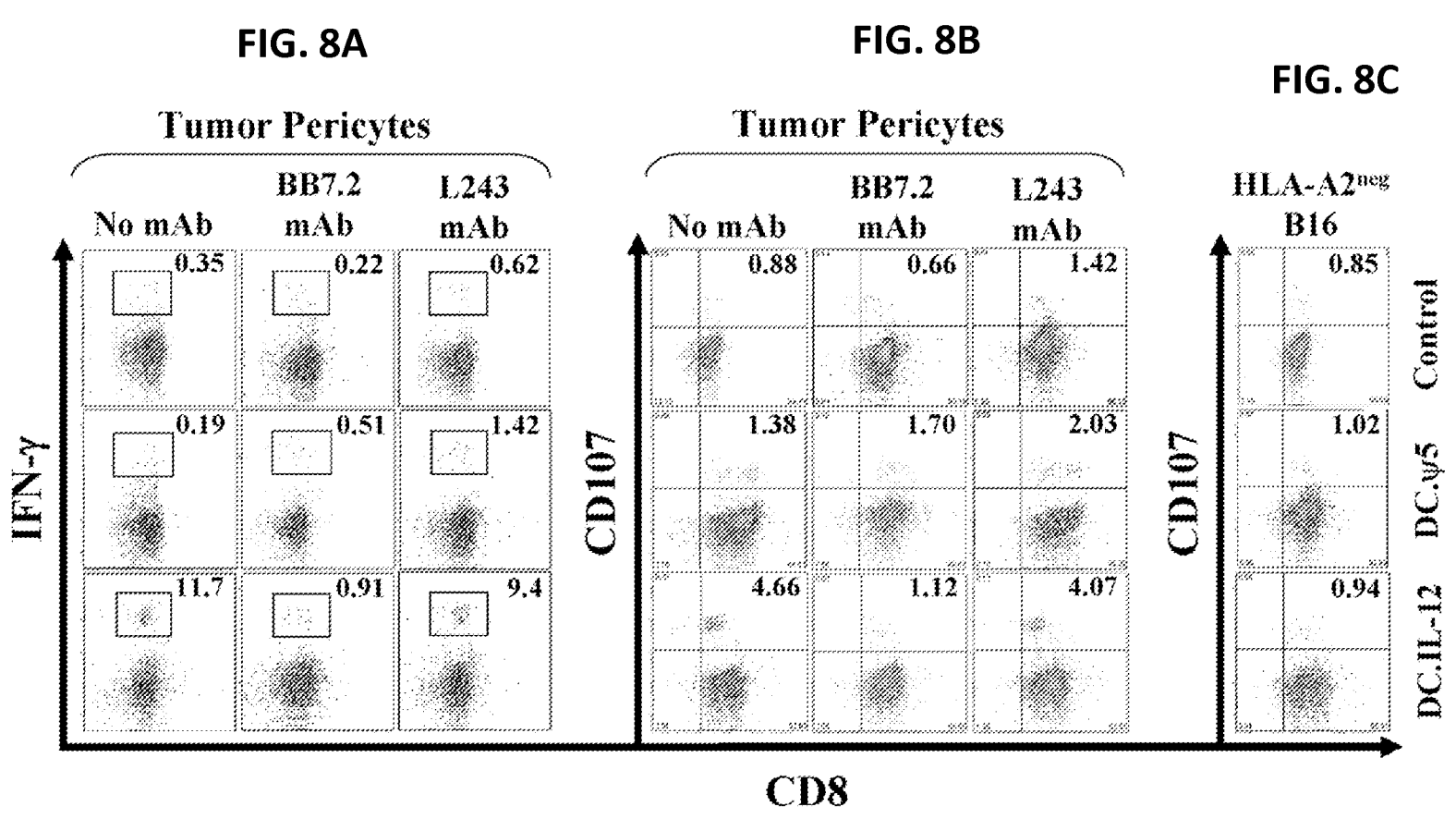

The impact of therapy on the ability of CD8+ tumor-infiltrating lymphocytes (TIL) freshly-isolated from day 17 tumors to recognize flow-sorted pericytes and VEC, as well as, TASA peptides presented by T2 cells was assayed. Using both intracellular IFN-γ staining (FIG. 3A) and CD107 translocation (FIG. 3B; i.e. a measure of effector T cell degranulation associated with perforin/granzyme-dependent lysis; (Mittendorf et al., *Breast Cancer Res Treat.*, 92:85-93, 2005) assays, it was observed that 3-12% of CD8⁺ TIL isolated from animals treated with DC.IL12 mediated effector Tc1 responses against tumor (but not kidney)-derived pericytes and VEC. Similar frequencies of CD8⁺ TIL from the DC.IL12-treated cohort of mice recognized TASA peptides presented by T2 cells (FIG. 3A, FIG. 3B). The ability of target cells to elicit effector responses from CD8⁺ TIL isolated from DC.IL12-treated mice was blocked by anti-HLA-A2 (but not anti-class II) mAb and these T cells display only background reactivity against HLA-A2$^{neg}$ B16 tumor cells (FIG. 8). In contrast, the frequency of TASA-specific CD8⁺ TIL isolated from untreated or DC.ψ5-treated melanoma was lower (versus DC.IL12 treatment) in all functional analyses performed (FIGS. 2C, 3A, 3B, 8).

CD8⁺ T Cells from HLA-A2⁺ Normal Donors or HLA-A2⁺ Melanoma Patients Recognize TASA-Derived Peptides In Vitro.

To assess whether the TASA-derived peptides identified in the HHD tumor model were also capable of being recognized by human CD8⁺ T cells, IVS was performed using T cells isolated from the peripheral blood of HLA-A2⁺ donors or HLA-A2⁺ patients with melanoma. DC were pulsed with peptides derived from a given TASA for 4 h at 37° C., then washed and used as stimulator cells for autologous CD8⁺ T cells. In cases where more than one peptide existed for a given protein, DC were pulsed with an equimolar (10 μM) mixture of each peptide. Two rounds of IVS using TASA for normal donors and a single-round of IVS using TASA for melanoma patients was applied. HLA-A2⁺ normal donors (FIG. 4; Tables 4, 5A and 5B) and melanoma patients (FIG. 4; Tables 4, 5A and 5B) were each capable of recognizing many of the TASA-derived peptides.

effect occurs via cross-presentation mediated by HLA-A2⁺ APCs emigrating from the TME (Zhang et al., *J Exp Med.*, 204:49-55, 2007).

TABLE 5A

Normal donor and melanoma patient demographics and responsiveness to TASA.*

| Donor | Age | Sex | Stage | Prior Therapy |
|---|---|---|---|---|
| ND1 | 51 | M | N/A | N/A |
| ND2 | 62 | F | N/A | N/A |
| ND3 | 37 | M | N/A | N/A |
| ND4 | 28 | M | N/A | N/A |
| ND5 | 50 | F | N/A | N/A |
| ND6 | 32 | F | N/A | N/A |
| ND7 | 26 | M | N/A | N/A |
| ND8 | 38 | F | N/A | N/A |
| Mel1 | 62 | F | IIA | S |
| Mel2 | 69 | M | IV | Anti-CTLA4 |
| Mel3 | 55 | F | IIC | C |
| Mel4 | 87 | F | IIC | MAA- VAC, IL-2 |
| Mel5 | 65 | M | IV | C, R |
| Mel6 | 71 | M | IV | GM2-KLH |
| Mel7 | 56 | F | IV | C |
| Mel8 | 64 | F | IV | C, IFN |
| Mel9 | 62 | F | IV | C, IFN |
| Mel10 | 56 | M | IV | C, IFN, IL-2 |

*Abbreviations used in Table 5A: AD, Active disease; C, Chemotherapy; CTLA-4, Cytotoxic T lymphocyte antigen-4; DC, dendritic cell, F, Female; IFN, Interferon-α, IL-2, Interleukin-2; GM2, Ganglioside M2; KLH, Keyhole limpet hemocyanin; M, Male; NED, No evidence of disease; R, Radiotherapy; S, Surgery; MAA, Melanoma-associated antigen; VAC, Vaccine.

TABLE 5B

Normal donor and melanoma patient demographics and responsiveness to TASA: Specific CD8⁺ T cell Production of IFN-γ in Response to TASA.

| Donor | DLK1 | EphA2 | HBB | NG2 | NRP1 | NRP2 | PFGFRβ | PSMA | RGS5 | TEM1 | VEGFR1 | VEGFR2 |
|---|---|---|---|---|---|---|---|---|---|---|---|---|
| ND1 | + | − | − | − | + | − | − | − | − | + | − | − |
| ND2 | + | − | + | − | + | − | + | − | − | + | − | − |
| ND3 | + | + | − | − | − | − | − | − | − | + | − | − |
| ND4 | − | − | − | − | − | + | − | − | − | − | − | − |
| ND5 | − | + | − | − | + | − | − | − | − | + | + | − |
| ND6 | − | − | − | − | + | − | − | − | − | − | − | − |
| ND7 | − | − | − | − | − | − | − | − | − | − | − | − |
| ND8 | + | − | + | − | − | − | − | − | − | − | − | − |
| Mel1 | + | + | + | − | + | + | − | − | + | + | − | − |
| Mel2 | + | + | + | − | + | + | − | − | + | − | − | − |
| Mel3 | − | + | + | − | + | − | − | − | − | − | − | − |
| Mel4 | + | + | + | + | + | + | − | + | + | + | + | − |
| Mel5 | − | − | − | − | + | + | − | − | − | − | − | − |
| Mel6 | + | + | + | + | + | − | − | + | + | − | + | − |
| Mel7 | − | − | + | − | + | − | − | − | − | + | + | − |
| Mel8 | + | − | − | + | + | − | + | − | + | + | − | − |
| Mel9 | + | + | − | + | − | − | − | − | − | − | − | − |
| Mel10 | − | − | − | − | − | − | − | − | − | − | − | − |

Figure 5:
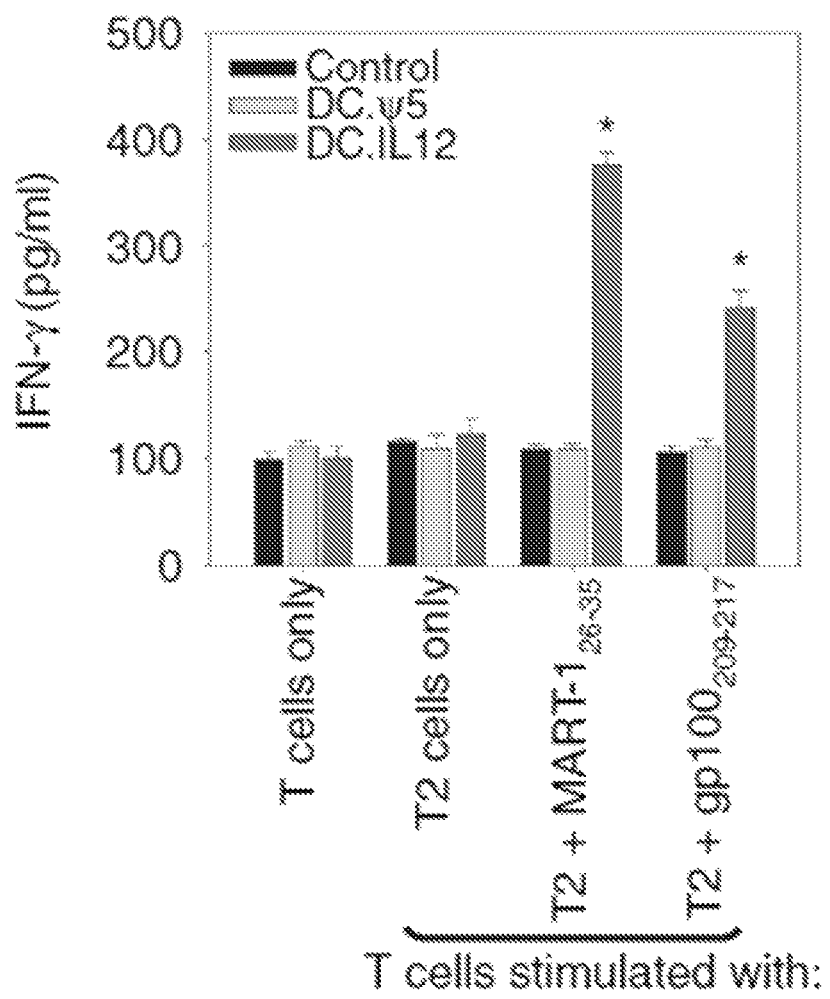
FIG. 5 shows a graph illustrating that splenic $CD8^+$ T cells from HHD mice effectively treated with DC.IL12 gene therapy develop HLA-A2-restricted responses against melanoma-associated antigens. HHD mice bearing day 7 HLA-$A2^{neg}$ (MART-$1^+$, gp$100^+$) B16 melanomas were left untreated or they were treated with intratumoral injection of control DC (DC.ψ5) or DC.IL12 as described in FIG. 2. On day 19 post tumor inoculation (i.e. 5 days after receiving the second injection of DC), $CD8^+$ spleen cells were isolated and analyzed for reactivity against the hMART-$1_{26-35}$ and h/mgp$100_{209-217}$ peptide epitopes presented by the $HLA-A2^+$ T2 cell line. After 48 h co-culture of T cells and Ag-loaded T2 cells, cell-free supernatants were harvested and analyzed for IFN-γ content by specific ELISA. *p<0.05 versus T2 only control.

As shown in FIG. 5, in the HHD recipient mouse model system, protective HLA-A2-restricted Tc1 cells failed to recognize HLA-A2$^{neg}$ B16 tumor cells, even though CD8⁺ T cells appeared to be cross-primed against HLA-A2-presented B16 melanoma-associated antigens such as MART-1 and gp100. A non-limiting explanation for this result is that the Human responses were designated as + if T cell reactivity against T2 cells presenting the indicated peptide (IFN-γ ELISA) was >30 pg/ml and more than 2 fold higher than reactivity versus T2 cells pulsed with the negative control HIV-nef$_{190-198}$ peptide (with p<0.05 versus T2+HIV-nef$_{190-198}$).

Without being bound by theory, this data suggests the translational utility of TASA peptides in the context of active vaccination protocols and/or clinical trials implementing immunotherapeutic/anti-angiogenic approaches (including IL-12p70 gene therapy, tyrosine kinase inhibitors (TKI) or VEGFR antagonists) for the treatment of solid cancers, such as melanoma.

Example 2

Vaccines Targeting Tumor Blood Vessel Antigens Promote CD8+ T Cell-Dependent Tumor Eradication or Dormancy in HLA-A2 Transgenic Mice This example illustrates that therapeutic vaccination of HHD mice with TBVA-peptides results in CD8+ T cell-dependent regression of colon carcinoma and melanoma and long-term protection against disease relapse.

Materials and Methods

Mice.

HHD mice are $D^b \times \beta_2$-microglobulin ($\beta_2$M) null, transgenic for the modified HLA-A*0201-h$\beta_2$-microglobulin single chain (HHD gene; Firat et al., 1999, *Eur. J. Immunol.* 29: 3112-3121) and exhibit CD8+ T cell responses that recapitulate those observed in HLA-A2+ human donors (28-30). C57BL/6 wild-type mice were purchased from The Jackson Laboratory (Bar Harbor, Me.). Female 6-8 week old mice were used in all experiments and were handled in accordance with an Institutional Animal Care and Use Committee (IACUC)-approved protocol.

Cell Lines.

MC38, a methylcholanthrene-induced (HLA-A2$^{neg}$) murine colon carcinoma cell line and B16 an HLA-A2$^{neg}$ melanoma cell line (syngenic to the H-2$^b$ background of HHD mice) have been described previously (Yamaguchi et al., 2007, *Cancer* 110: 1469-1477, Hatano et al., 2004, *J. Transl. Med.* 2: 40). The T2 cell line is a TAP-deficient T-cell/B-cell hybridoma that constitutively expresses HLA-A2 (Stuber et al., 1994, *Eur. J. Immunol.* 24: 765-768). All cell lines were free of *mycoplasma* contamination.

Peptides.

All peptides were synthesized using 9-fluorenylmethoxycarbonyl (Fmoc) chemistry. Peptides were >96% pure based on high performance liquid chromatography profile and mass spectrometric analysis.

Production of Murine Bone Marrow (BM)-Derived DCs and DC.IL12.

DC were generated from BM precursors isolated from the tibias/femurs of HHD mice, as previously described (28). The Ad mIL-12p70 and Ad.ψ5 (empty) recombinant adenoviral vectors were produced as reported previously (34). Five million (day 5 cultured) DCs were infected at MOI=50 with Ad mIL-12p70 or the control, empty vector Ad.ψ5. While control DC produced <62.5 pg IL-12p70/ml/48 h/$10^6$ cells, DC.IL12 cells produced 1-10 ng IL-12p70/ml/48 h/$10^6$ cells (Komita et al., *Cancer Res.*, 68:8076-8084, 2008).

Vaccine Experiments.

For prophylactic experiments, HHD mice were immunized subcutaneously on the right flank with 100 μl PBS or PBS containing $10^6$ syngenic DC.IL12 cells that had been untreated or pre-pulsed for 4 h at 37° C. with 10 μM synthetic peptide(s). Immunizations occurred on days -14 and -7, with mice subsequently receiving injections of MC38 ($2\times10^6$) tumor cells in the left flank on d0. In all cases, treatment groups contained 5 mice per cohort. For analysis of tumor cellular composition in repeat experiments, MC38 tumors were isolated by surgical resection 10 days after tumor inoculation and prepared for fluorescence imaging, as described below. For therapeutic experiments, MC38 ($2\times10^6$) or B16 melanoma cells ($1\times10^5$) were injected subcutaneously in the right flank and allowed to establish/progress for 7 days, at which time, the mice were randomized into cohorts of 5 mice each, with each group exhibiting an approximate mean tumor size of 50-75 mm$^2$. Mice were then untreated or treated with control, syngenic DC.IL12 or DC.IL12 ($10^6$ cells injected subcutaneously in the left flank on days 7 and 14) pulsed with synthetic TBVA peptides. In some assays, as indicated, in vivo antibody depletions (on days 6, 13 and 20 post-tumor inoculation to assess early involvement or on days 60 and 67 or 180 and 187 to assess late involvement) of protective CD4+ T cells or CD8+ T cells were performed and monitored as previously described (Zhao et al., *Mol Ther.*, 19:805-814, 2011). In all cases, tumor size (area) was monitored every 3-4 days and is reported as mean+/-SD in mm$^2$.

Evaluation of Specific CD8+ T Cell Responses in HHD Mice.

MACS (Miltenyi Biotec) CD8+ splenocytes were harvested (from 3 mice/group) 7 days after the second round of DC-based vaccination (i.e. day 21 after tumor inoculation) and analyzed for reactivity against unpulsed T2 cells, TBVA peptide-pulsed T2 cells, or day 19 (flow-sorted) B16-derived PDGFRβ+CD31$^{neg}$H-2K$^{b(neg)}$ pericytes or PDGFRβ$^{neg}$CD31+H-2K$^{b(neg)}$ VEC isolated as previously described (Zhao et al., *Mol Ther.*, 19:805-814, 2011). Where indicated, 10 μg of anti-HLA-A2 mAb BB7.2 or control anti-class II mAb L243 (both from ATCC, Manassas, Va.) were added to replicate co-culture wells. After 48 h, supernatants were analyzed for mIFN-γ content by specific ELISA (BD-Biosciences; lower detection limit=31.3 pg/ml). Data are reported as the mean±SD of triplicate determinations.

RT-PCR.

Reverse transcriptase-PCR (RT-PCR) was performed using primer pairs as described in Example 1.

Fluorescence Imaging of Tumor Sections.

Tumor tissue samples were prepared and 6 micron sections prepared as previously reported (Komita et al., *Cancer Res.*, 68:8076-8084, 2008). The following Abs were used: (for T cell analyses), rabbit anti-mouse NG2 (Millipore, Bedford, Mass.) and alexa488-conjugated anti-CD4 or -CD8β antibodies or matching isotype controls (all from BD-Biosciences); (for vascular analyses), rat anti-mouse CD31 (BD-Biosciences) and rabbit anti-mouse NG2 (Millipore) Abs; (for TBVA), rat anti-mouse CD31 (BD-Biosciences) and guinea pig anti-mouse NG2 Abs, along with anti-TBVA as described in Example 1. Imaging was performed using an Olympus Fluoview 500 Confocal microscope (Olympus America, Center Valley, Pa.).

Cutaneous Wound Healing Assays.

Wound healing analyses were performed in HHD mice as described by Maciag et al. (Maciag et al., *Cancer Res.*, 68:8066-8075, 2008).

Statistical Analysis.

Two-tailed Student's t-test or two-way ANOVA were used to test overall differences between groups (StatMate III, ATMS Co., Tokyo, Japan), with p-values <0.05 considered significant.

Results

Vaccines Incorporating Peptide Epitopes Derived from TBVA are Immunogenic and Protect HHD Mice Against HLA-A2$^{neg}$ MC38 Tumor Challenge.

Figure 9A:
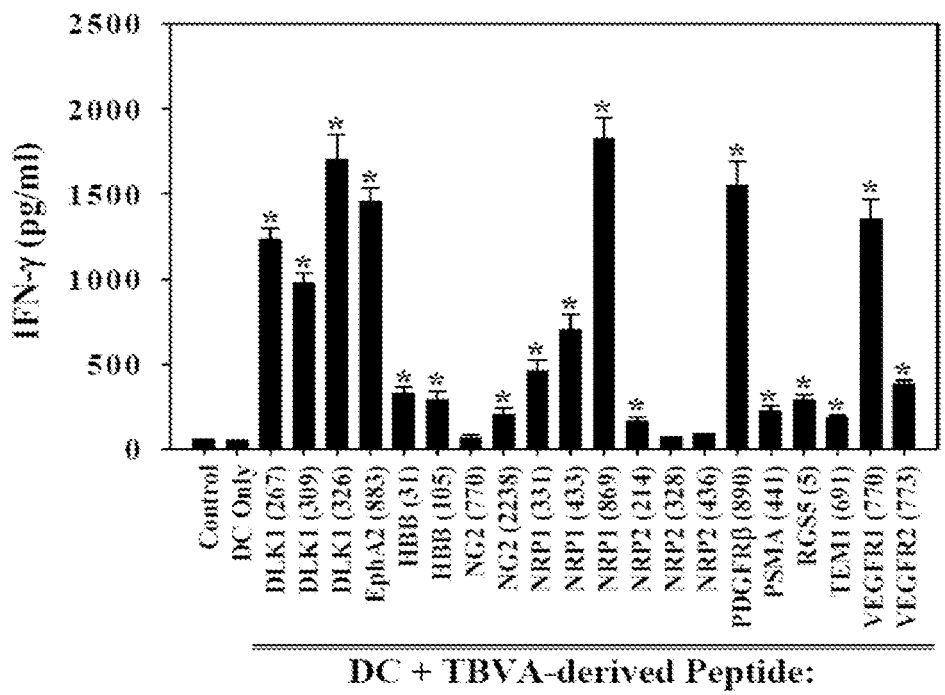
FIGS. 9A-9B show a series of graphs illustrating induction of specific/protective $CD8^+$ T cells reactive against TASA as a consequence of DC/peptide-based vaccination.

To assess the immunogenicity of TBVA-derived peptides, female HLA-A2 Tg (HHD; lacking murine H-2$^b$ class I molecules) mice were vaccinated twice on a weekly schedule with $10^6$ peptide-pulsed, (HHD) DC.IL12 cells. One week after the booster immunization, CD8+ splenocytes were isolated and analyzed for their ability to secrete IFN-γ in response to peptide-pulsed HLA-A2+ T2 cells in vitro. As shown in FIG. 9A, the majority (17/20; p<0.05 versus T cells stimulated with DC only) of TBVA-derived peptides analyzed primed Tc1 responses in vivo that could be detected in vitro.

Figure 9B:
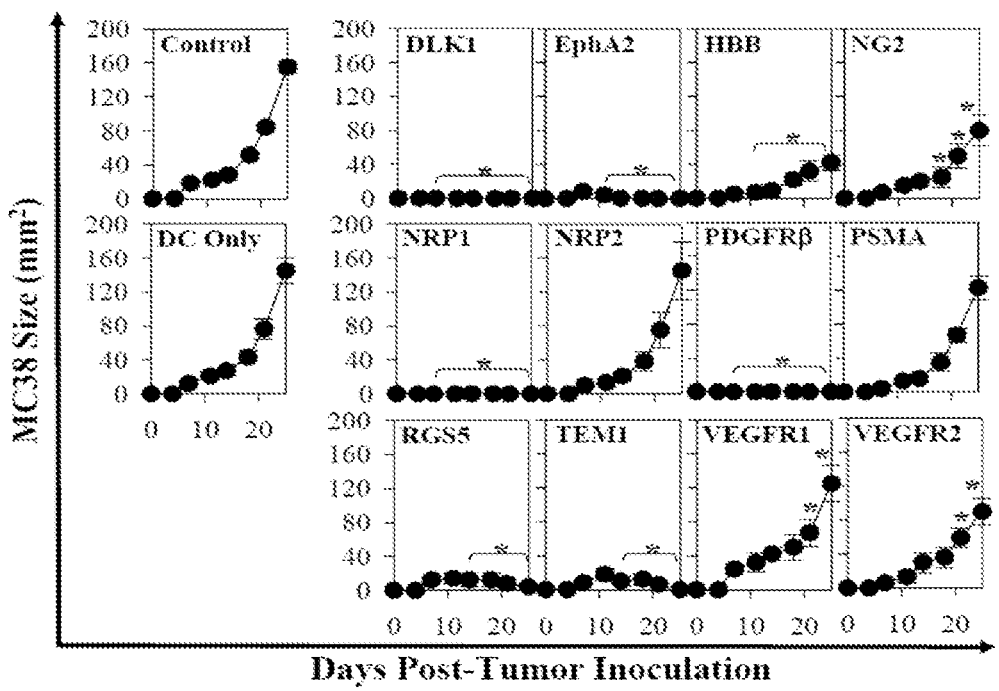
Figure 14:
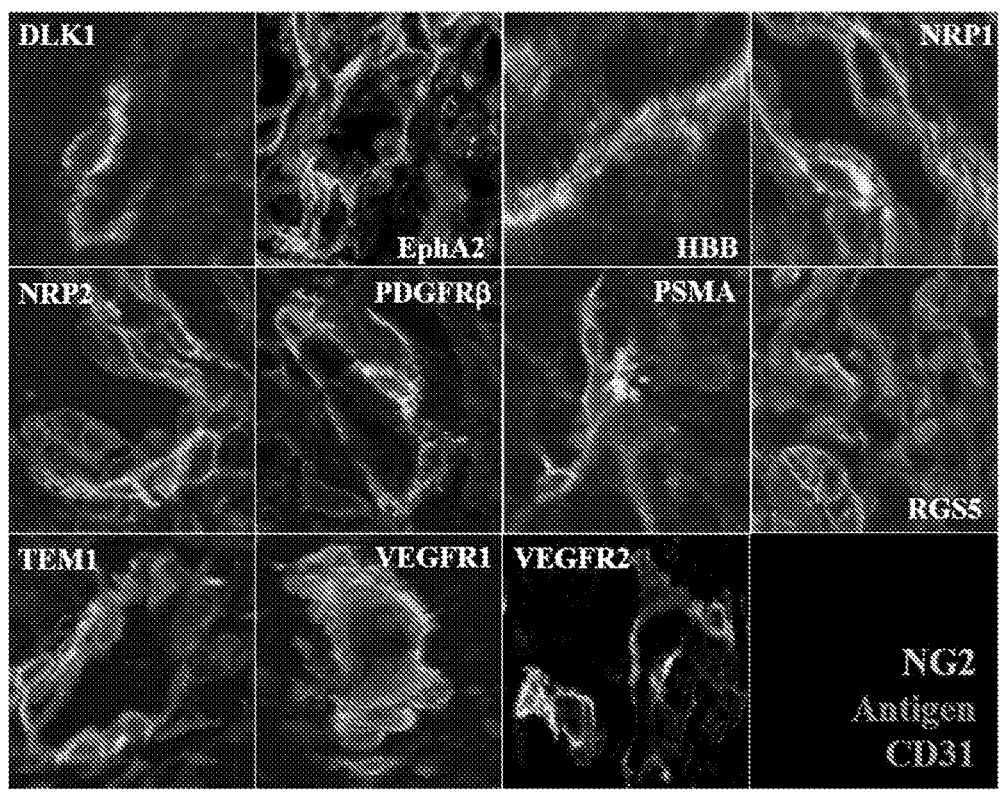
FIG. 14. shows a series of digital images illustrating expression of TASA in the established MC38 TME. MC38 colon carcinoma cells were injected subcutaneous in the right flank of female HHD mice and allowed to establish/progress for 14 days. Animals were then euthanized, with tumors resected, fixed, sectioned and analyzed for expression of the indicated antigens using specific antibodies and fluorescence microscopy. Specific antibody against NG2 (green), the indicated antigen of interest (red), and CD31 (blue) were used to distinguish preferential antigen expression in tumor-associated stromal pericytes, VEC, alternate stromal cells and/or tumor cells. Images are reflective of those obtained in three independent experiments performed.

The DLK1, EphA2, HBB, NG2, NRP1, NRP2, PDGFRβ, PSMA, RGS5, TEM1, VEGFR1 and VEGFR2 antigens were expressed in situ by blood vessel cells in the MC38 colon carcinoma TME (FIG. 14). Protection of HHD mice against a challenge with HLA-A2$^{neg}$ MC38 tumor cells injected subcutaneously on day zero was assayed with immunization with TBVA-derived peptides on days-14 and -7. As depicted in FIG. 9B, vaccines incorporating peptides from the TBVA DLK1, EphA2, HBB, NRP1, PDGFRβ, RGS5 or TEM1 were effective in preventing HLA-A2$^{neg}$ MC38 tumor establishment or they resulted in the regression of tumors (after a transient period of establishment) in HHD mice. In contrast, vaccines based the TBVA NG2, NRP2, PSMA, VEGFR1 or VEGFR2 yielded minimal protection (FIG. 9B). Based on the data provided in FIG. 9, vaccine immunogenicity and efficacy were not always correlated with one another in the MC38 prophylaxis model (FIG. 16), a finding in accordance with reports for peptide-based vaccines in human clinical trials (Jandus et al., *Pigment Cell Melanoma Res.*, 22:711-723, 2009; Vujanovic and Butterfield, *J. Cell. Biochem.*, 102:301-310, 2007; Yu and Restifo, *J. Clin. Invest.*, 110:289-294, 2001).

Protective Vaccines Incorporating TBVA Peptides Promote Enhanced Infiltration of the TME by CD8+ T Cells in Association with an Inhibition of Tumor Vascularity.

Figure 10A:
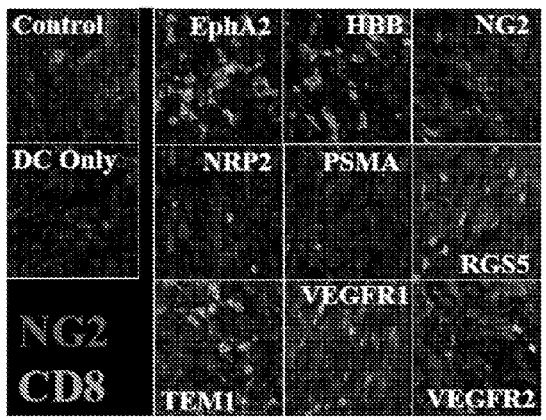
FIGS. 10A-10D show a series of digital images and graphs illustrating that MC38 tumors in mice pre-vaccinated with TASA-derived peptides exhibit differential infiltration by $CD8^+$ T cells and alterations in vascular density. Day 14 MC38 tumors were harvested from HHD mice that had been vaccinated as outlined in FIG. 9B with the indicated peptides (or control PBS or DC.IL12 alone=No peptide).
Figure 10B:
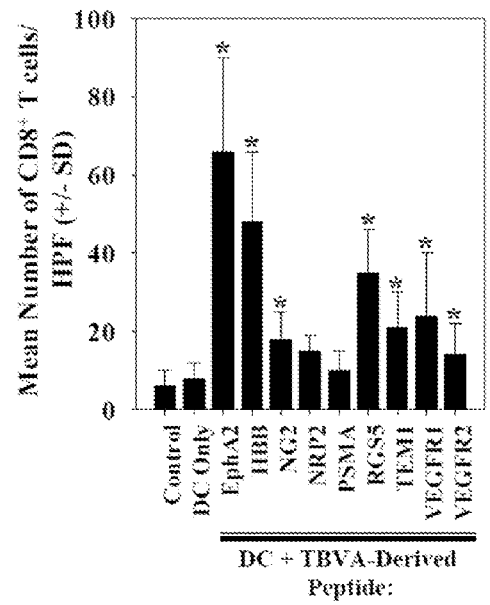
Figure 10C:
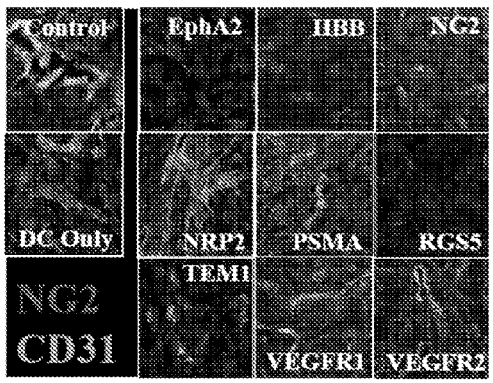
Figure 10D:
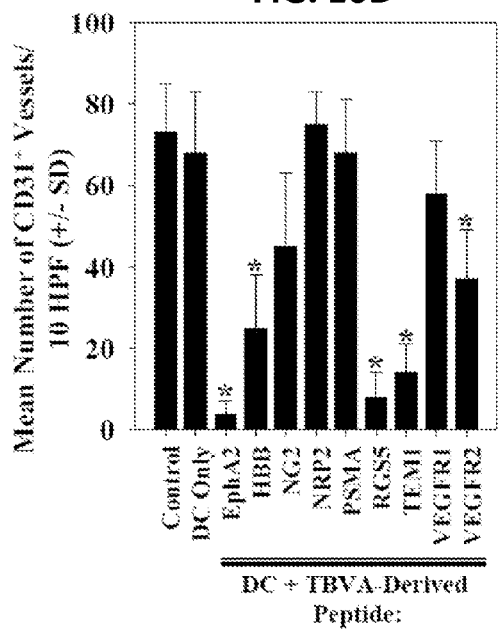
Figure 16:
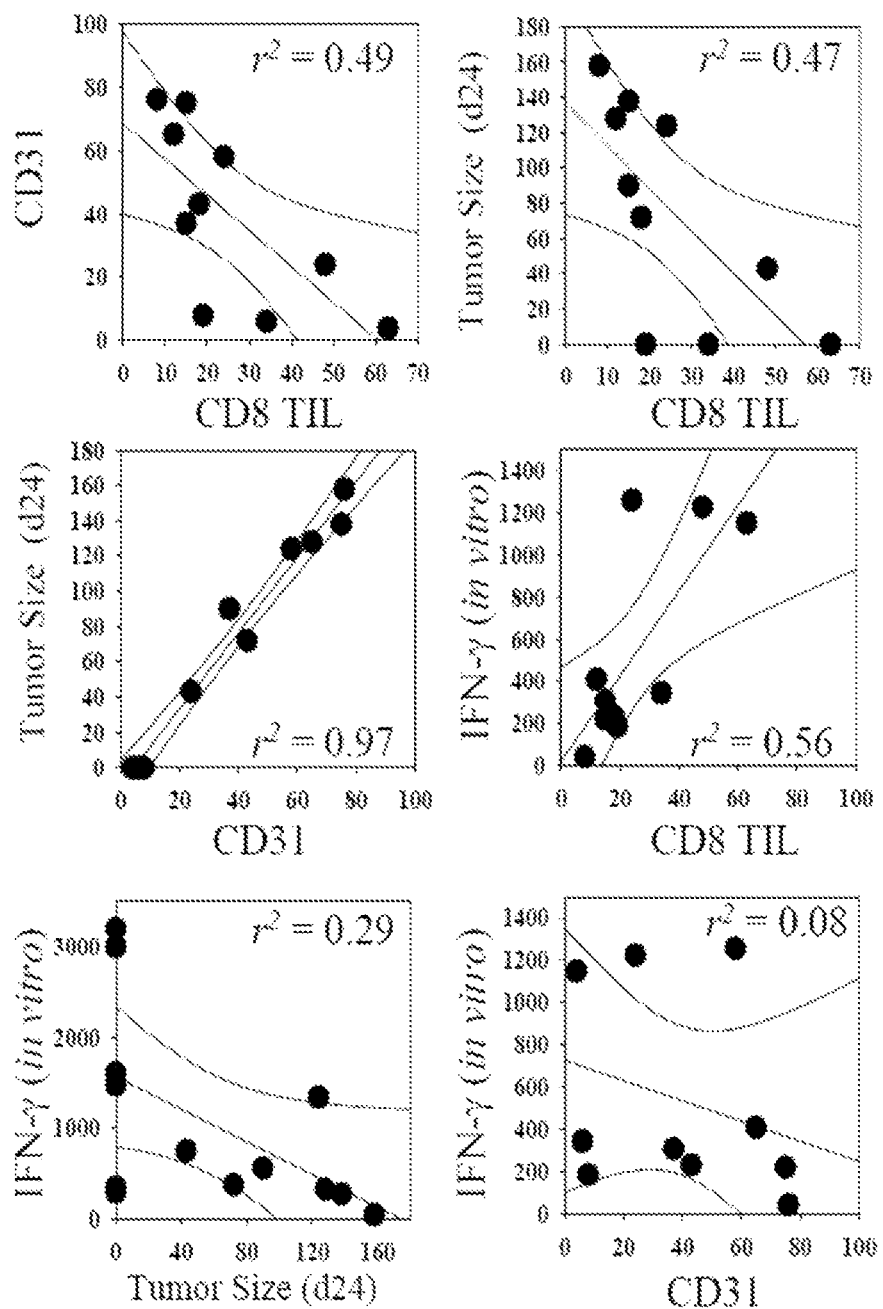
FIG. 16. shows a series of graphs illustrating correlation of biologic parameters assessed in the MC38 tumor model system. Data harvested from FIG. 1 and FIG. 2 were analyzed for the correlation of indicated markers in a pair-wise manner.

MC38 tumor lesions from all cohorts of animals with evidence of disease on day 14 (post-tumor inoculation) were isolated and immunofluorescence microscopy on tumor sections was performed. Although control (untreated or vaccinated with DC.IL12/no peptide) mice contained few CD8+ T cells in the TME, the majority of the peptide vaccinated cohorts exhibited a variable, but significantly elevated number of CD8+ TILs (FIG. 10A, FIG. 10B). In marked contrast, CD4+ T cell infiltration in the TME was sparse and the data were indistinguishable when comparing control vs. vaccinated mice (FIG. 17). An analysis of vascular structures in these tumors revealed that mice pre-vaccinated with peptides derived from the TBVA EphA2, RGS5 or TEM1 had the greatest degree of suppression in CD31+ vessel counts in the MC38 TME, with somewhat less pronounced effects also noted for groups vaccinated against HBB or VEGFR2 (FIG. 10C, 10D; p<0.05 vs. untreated mice or mice vaccinated with DC.IL12/no peptide). Correlative analyses indicated an association between the anti-tumor efficacy of vaccines and their ability to promote CD8+ T cell infiltration and reduced vascularity in the TME (FIG. 16).

Therapeutic Vaccines Incorporating TBVA-Derived Peptide Epitopes are Effective Against Established HLA-A2$^{neg}$ MC38 Colon Carcinomas and HLA-A2$^{neg}$ B16 Melanomas in HHD Mice.

Figure 11A:
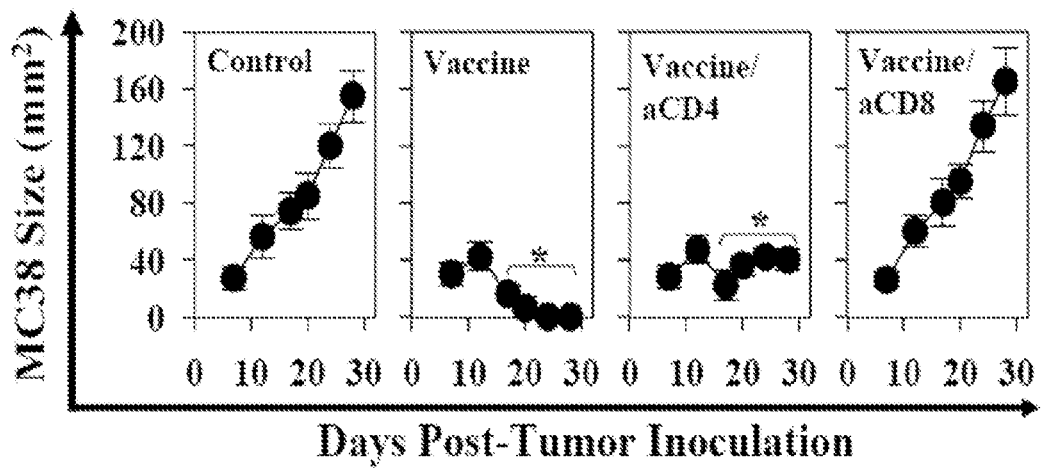
FIGS. 11A-11C show a series of graphs illustrating that DC.IL12 vaccines containing TASA-derived peptides are therapeutic against MC38 colon carcinomas and B16 melanomas in HHD mice.

Given the robust anti-tumor activity noted for vaccines based on a subset of TBVA in the prophylactic model, the efficacy of these vaccines as immunotherapies in mice bearing established day 7 subcutaneous MC38 or B16 tumors was assayed. In the MC38 model, HHD mice were treated with DC.IL12 cells pulsed with (an equimolar mixture of) peptides derived from TBVA shown most capable of regulating tumor growth under prophylactic conditions (FIG. 9B) and exhibiting the highest degree of immunogenicity based on data provided in FIG. 9A (i.e. DLK1$_{326-334}$, EphA2$_{883-891}$, HBB$_{31-39}$, NRP1$_{869-877}$, PDGFRβ$_{890-898}$, RGS5$_{5-13}$ and TEM1$_{691-700}$). As shown in FIG. 11A, the combination peptide vaccine effectively promoted the regression of established MC38 tumors. Furthermore, based on Ab-depletion analyses, therapeutic benefit was largely due to the action of CD8+, but not CD4+, T cells (FIG. 11A).

Figure 11B:
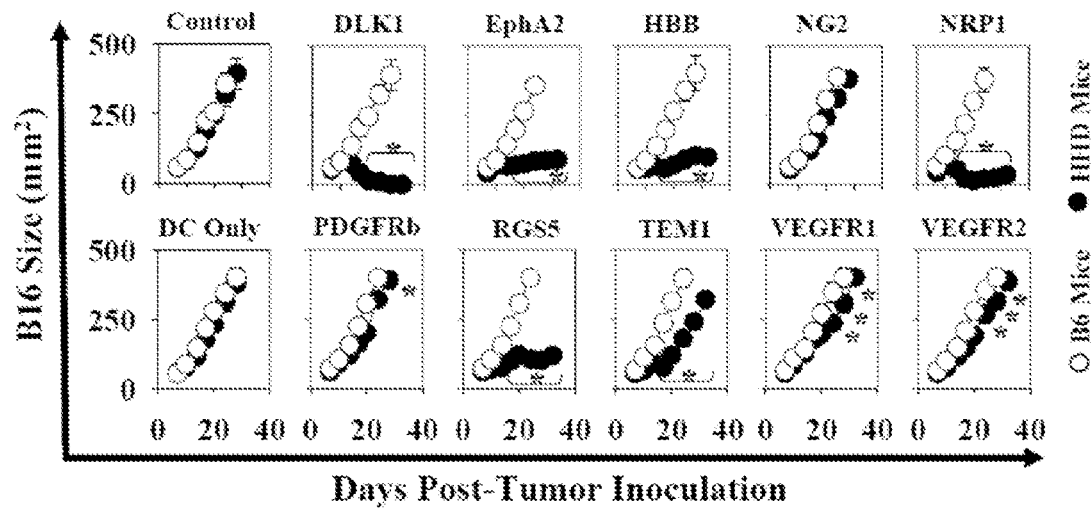

Therapeutic vaccines applied to mice bearing B16 melanomas were also effective in suppressing tumor growth if: i) the vaccine-incorporated peptides derived from the stromal antigens DLK1, EphA2, HBB, NRP1, RGS5 (and to a lesser extent TEM1) and ii) recipient mice were competent to respond to these peptides in an HLA-A2-restricted manner (FIG. 11B). Hence, none of the vaccines evaluated perturbed B16 tumor growth in syngenic B6 mice, which fail to express the relevant HLA-A2 class I restriction element required for CD8+ T cell recognition of the immunizing peptides.

HHD Mice Cured of B16 Tumors by TBVA Peptide-Based Therapeutic Vaccines Exhibit Extended Survival and Durable Tc1 Responses Against Tumor-Associated Pericytes and/or VEC, and Spreading in Anti-TBVA CD8+ T Cell Repertoire.

Figure 11C:
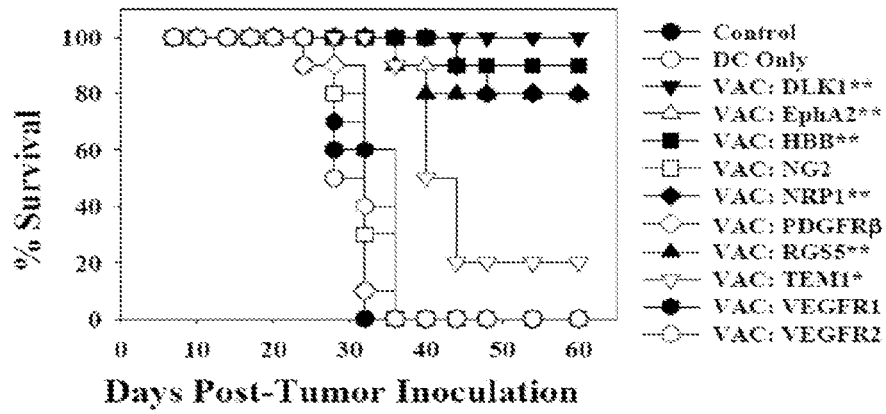
Figure 12:
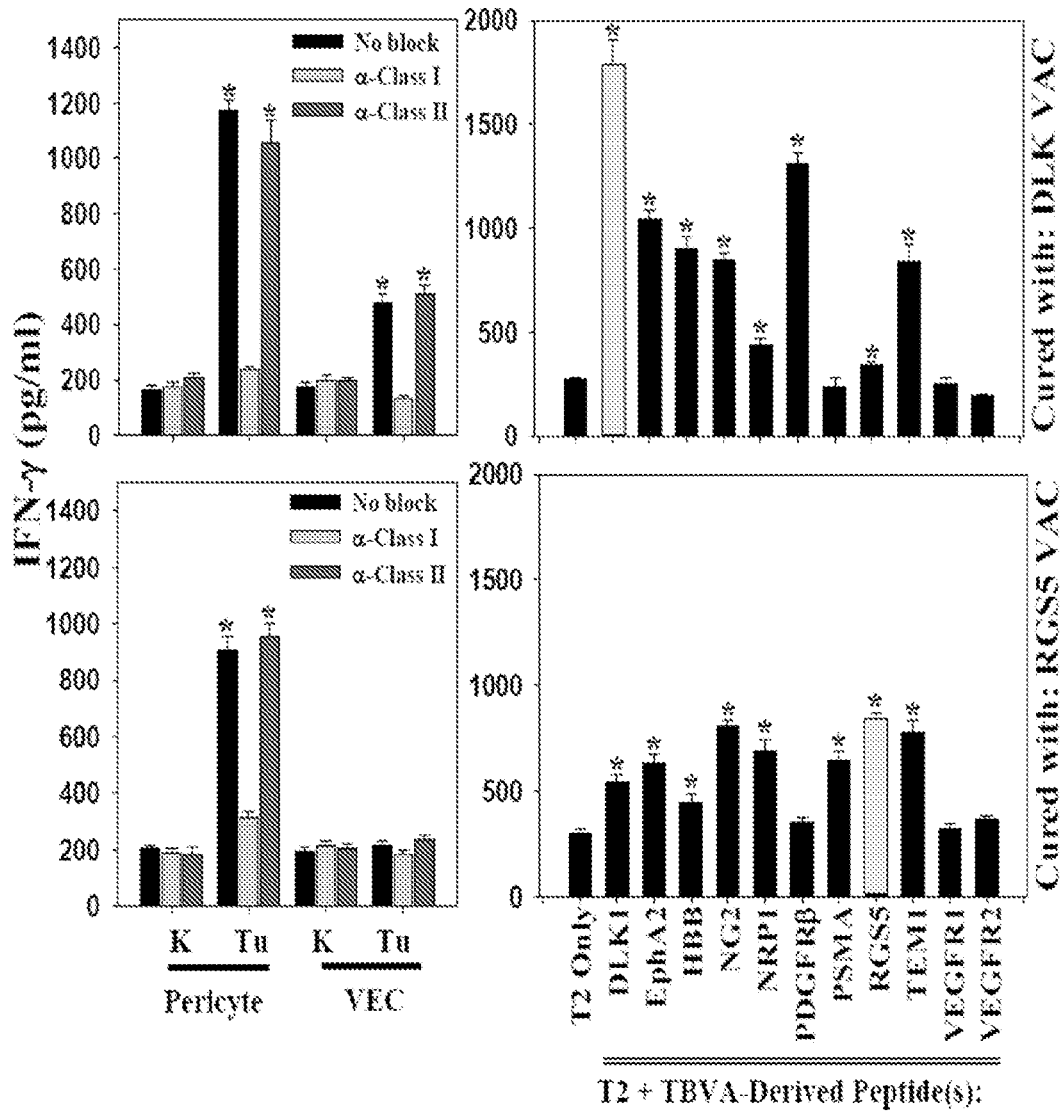
FIG. 12 shows a series of graphs illustrating that HHD mice treated for B16 melanoma by treatment with DC.IL12/peptide vaccination exhibit poly-specific anti-TASA Type-1 $CD8^+$ T (Tc1) responses. HHD mice bearing established day seven B16 melanomas were therapeutically vaccinated with peptides derived from the TASA DLK1 or RGS5 as described in FIG. 11B. Tumors regressed to a non-detectable level over the next two weeks. Sixty days after tumor inoculation, $CD8^+$ T cells were MACS-isolated from the spleens of these animals and evaluated for IFN-γ production (by ELISA) in response to pericytes and VEC (flow-sorted from day 19 untreated B16 tumors or tumor-uninvolved kidneys of B16-bearing HHD mice), as well as, HLA-$A2^+$ T2 cells (control or pulsed with the indicated peptides). *$p<0.05$ versus anti-class I mAb blockade (when evaluating responses against pericytes, VEC or B16 tumor cells) or T2 cells only (when evaluating anti-peptide responses). Data are reflective of responses observed in three independent experiments.

Mice treated as in FIG. 11B were followed through 60 days post-tumor inoculation and observed significant survival benefits if the animals had been treated with vaccines containing peptides derived from the TBVA DLK-1, EphA2, HBB, NRP1, RGS5 or TEM1 (FIG. 11C, Table 6). To analyze the status and specificity of Tc1 cells, HHD mice rendered free of B16 melanoma after therapeutic vaccination with DLK or RGS5 peptide-based vaccines were sacrificed 60 days after tumor inoculation. Fresh MACS-isolated spleen CD8+ T cells were then analyzed for reactivity against HLA-A2+PDGFRβ+CD31$^{neg}$ pericytes, HLA-A2+PDGFRβ$^{neg}$CD31+ VEC or HLA-A2$^{neg}$ tumor cells flow-sorted from day 19 B16 tumors growing progressively in untreated HHD mice. As shown in FIG. 12, splenic Tc1 cells isolated from mice cured after vaccination with DLK1 peptides recognized tumor-associated pericytes and VEC in an MHC class I-restricted manner. They failed to recognize pericytes or VEC isolated from the tumor-uninvolved kidneys of these same donor animals. These Type-1 CD8+ T cells strongly recognized the DLK1 peptides used in the protective vaccine formulation, but also (to a variable degree), a number of additional TBVA-derived peptides that were not included in the therapeutic vaccine. Similarly, B16-bearing HHD mice cured using a vaccine based on the RGS5$_{5-13}$ peptide, demonstrated clear Tc1 recognition of tumor (but not tumor-uninvolved kidney) pericytes, as well as, statistically-significant response against HLA-A2+ T2 cells pulsed with peptides derived from the TBVA DLK1, EphA2, NG2, NRP1, PSMA, RGS5 or TEM1 (FIG. 12).

TABLE 6

In vivo immunogenicity and anti-tumor efficacy of TBVA-based vaccines in HHD models.*

| TASA | AA Positions | Peptide Sequence | SEQ ID NO | Tc1 Response to Peptide Vaccine (HHD)[a] | Anti-tumor efficacy in MC38 protection model[b] | Anti-tumor efficacy in B16 therapy model (survival: pvalue)[c] |
|---|---|---|---|---|---|---|
| DLK1 | 269-277 | RLTPGVHEL | 68 | + | + | .0013 |
|  | 310-318 | ILGVLTSLV | 2 | + |  |  |
|  | 326-334 | FLNKCETWV | 3 | + |  |  |
| EphA2 | 883-891 | TLADFDPRV | 10 | + | + | .0012 |
| HBB | 31-39 | RLLVVYPWT | 70 | + | + | .0012 |
|  | 105-114 | RLLGNVLVCV | 72 | + |  |  |
| NG2 | 770-778 | TLSNLSFPV | 83 | − | + | NS |
|  | 2238-2246 | LILPLLFYL | 14 | + |  |  |
| NRP1 | 331-339 | GLLRFVTAV | 6 | + | + | .0013 |
|  | 433-441 | GMLGMVSGL | 75 | + |  |  |
|  | 869-877 | VLLGAVCGV | 8 | + |  |  |
| NRP2 | 214-222 | DIWDGIPHV | 15 | + | − | NT |
|  | 328-336 | YLQVDLRFL | 16 | − |  |  |
|  | 436-444 | NMLGMLSGL | 17 | − |  |  |
| PDGFRβ | 890-898 | ILLWEIFTL | 81 | + | + | NS |
| PSMA | 441-450 | LLQERGVAYI | 18 | + | − | NT |
| RGS5 | 5-13 | LAALPHSCL | 79 | + | + | .0012 |
| TEM1 | 691-700 | LLVPTCVFLV | 76 | + | + | .0102 |
| VEGFR1 | 770-778 | TLFWLLLTL | 19 | + | +/− | NS |
| VEGFR2 | 773-781 | VIAMFFWLL | 20 | + | +/− | NS |

*Data are summarized from FIG. 9 and FIG. 11.
[a]+, $p < 0.05$ versus DC only.
[b]Vaccines consisted of DC.IL12 pulsed with a pool of 1 or more peptides derived from the indicated TBVA. +/−, $p < 0.05$ versus DC only for 2 consecutive time points; +, $p < 0.05$ versus DC only for >2 consecutive time points; − not significant at any time point analyzed.
[c]p-value versus mice treated with DC only vaccine (from FIG. 11C). NS, not significant; NT, not tested.

HHD Mice Cured of B16 Tumors by TBVA Peptide-Based Therapeutic Vaccines Either Exhibit True "Molecular Cures" or a State of CD8+ T Cell-Mediated Tumor Dormancy.

Figure 13:
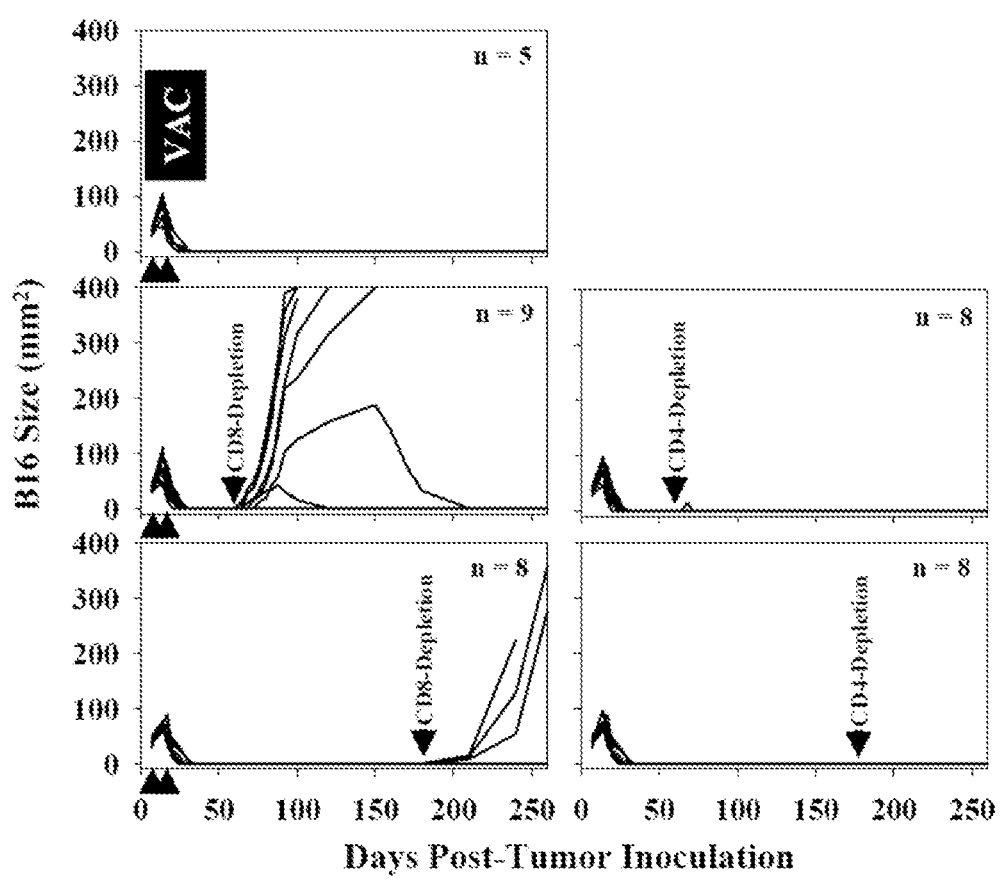
FIG. 13 shows a series of graphs illustrating that in vivo depletion of $CD8^+$, but not $CD4^+$, T cells from a cohort of HHD mice effectively treated with TASA peptide-based vaccines results in recurrence of disease at the site of primary tumor inoculation. HHD mice harboring established subcutaneous B16 melanomas received vaccines consisting of syngenic DC.IL12 pulsed with a mixture of TASA peptides on days 7 and 14 (post-tumor inoculation) as outlined in FIG. 11A, resulting in tumor regression in 100% of treated animals. On days 60 and 67 or days 180 and 187 (post-tumor inoculation) mice were depleted of $CD4^+$ or $CD8^+$ T cells by intraperitoneal injection with specific antibodies. Control animals received i.p. injections of isotype control antibodies. Specific T cell subset depletions were confirmed by flow cytometry analyses performed on peripheral blood obtained by tail. Animals were then monitored for the reappearance and size of melanomas every 4-7 days. The number of animals evaluated per cohort is indicated within a given panel, with each line representing longitudinal data from a given animal. Data are cumulative from three experiments performed.

Effectively-treated HHD mice with no evidence of (macroscopic) disease were depleted of CD8+ or CD4+ T cells on days 60 and 67, or 180 and 187 by injection of specific antibodies in vivo. As shown in FIG. 13, depletion of CD8+ T cells, but not CD4+ T cells, resulted in the re-establishment of melanoma growth at sites of the primary tumor placement in 7/9 (i.e. 78% for depletions on days 60/67) and 3/8 (i.e. 38% for depletions on days 180/187) cases, respectively. Interestingly, 2/9 (22%) mice in the day 60/67 CD8+ T cell-depleted group exhibited transient tumor expansion and then "spontaneous" regression over a period of weeks-to-months (FIG. 13); a non-limiting explanation for this finding is that TBVA/tumor-specific CD8+ T effector cells recovered in these animals. Additionally, at the time of primary disease recurrence in CD8+ T cell-depleted animals, melanomas did not present in distal cutaneous sites and that metastases were not detected in the lung, liver or brain based on a histopathology examination of resected tissues.

To show that that prior vaccination against TASA does not inhibit wound-healing in HHD mice, female HHD mice (5 animals/cohort) were vaccinated in the right flank on d-14 and d-7 with saline, 106 DC.IL12 alone or 106 DC.IL12 pulsed with peptides derived from the indicated TASA. In cases where more than one peptide is identified for a given TASA, an equimolar pool of the indicated peptides (each 10 μM) was pulsed onto DC.IL12 and used for vaccination in the relevant cohort. On d0, mice were anesthetized, with skin on the upper back shaved and sterilized topically, before placement of two 3-mm diameter wounds using a sterilized punch biopsy instrument. Wounds were not treated consequently and no infections were observed in any animals. The time to closure for the 10 wounds/cohort (2 sites/animal×5 mice/group) was assessed daily and is reported as the mean number of days+/− SD for complete wound closure (FIG. 18).

Figure 15:
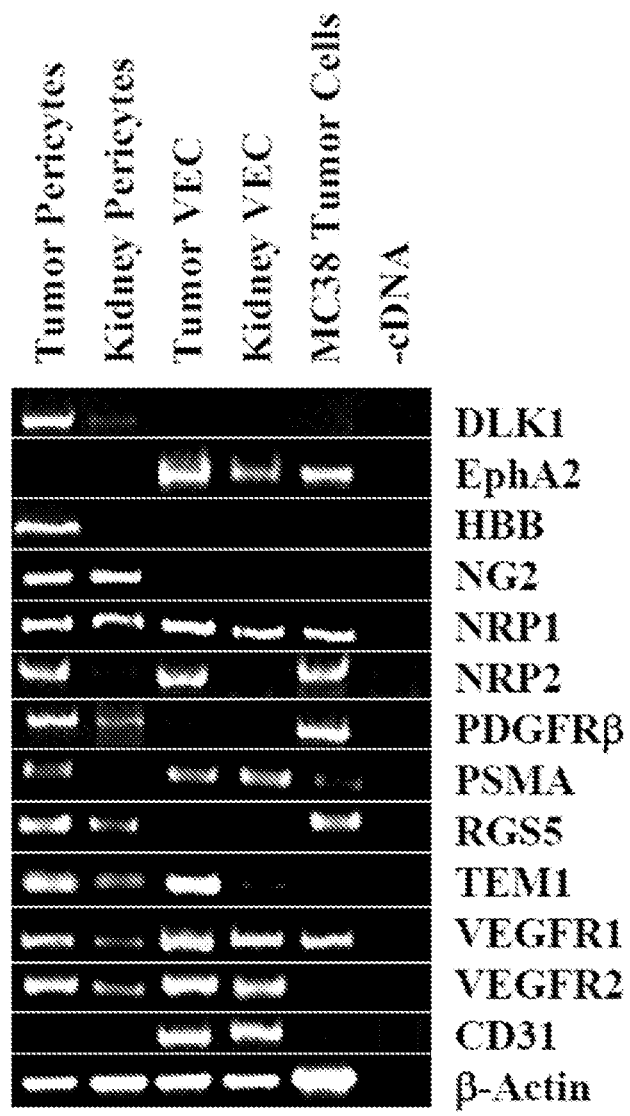
FIG. 15. shows a series of digital images illustrating RT-PCR analysis of "stromal" antigen expression by pericytes, VEC and tumor cells in MC38 tumor-bearing mice. MC38 colon carcinoma cell lines, as well as, flow-sorted tumor- and tumor-uninvolved kidney-associated pericytes and VEC (isolated from HHD mice bearing untreated day 14 tumors) were analyzed for expression of the indicated mRNAs using RT-PCR.

To determine expression of selected TASA in tissue, RT-PCR analysis of "stromal" antigen expression by pericytes, VEC and tumor cells in MC38 tumor-bearing mice was examined (FIG. 15). MC38 colon carcinoma cell lines, as well as, flow-sorted tumor- and tumor-uninvolved kidney-associated pericytes and VEC (isolated from HHD mice bearing untreated day 14 tumors) were analyzed for expression of the indicated mRNAs using RT-PCR. As shown in FIG. 15, several of the selected TASA were expressed in the examined tissue.

Thus, a subset of TBVA-derived peptides elicit protective/therapeutic immunity against HLA-A2[neg] (MC38 or B16) transplantable tumors in HHD mice due to the apparent CD8+ T cell targeting of HLA-A2+ pericytes or VEC in the TME. Without being bound by theory, because similar peptide-based vaccines applied to CD8-depleted HHD mice or HLA-A2$^{neg}$ recipient (C57BL/6) mice failed to yield treatment benefit, indicating involvement of CD8$^+$ T cells and the need for these effector cells to target HLA-A2$^+$ stromal cells in vivo. Additionally, many responders in the therapeutic vaccine models retained occult disease, since CD8$^+$, but not CD4$^+$, T cell depletion of such animals resulted in the rapid recurrence of tumors selectively at the site of the original primary lesion in many cases. While in most instances, recurrent tumors grew quickly and proved lethal, in some cases (i.e. 2/10), tumors grew slowly and subsequently underwent spontaneous regression presumably after the Ab-depleted CD8$^+$ T cell repertoire had recovered. Without being bound by theory, these data indicate that TBVA peptide-based vaccines can promote either complete eradication of tumors or the establishment of a state of (occult) tumor dormancy over extended periods of time which is regulated by vaccine-instigated CD8$^+$ T cells.

Example 3

Therapeutic Vaccination Against Tumor Pericyte-Associated Antigen DLK1

This example provides evidence that the NOTCH antagonist delta-like kinase-1 (DLK1) peptides can be used therapeutically, such as, but not limited to, in treatments for renal cell carcinoma.

Renal cell carcinoma is highly-vascularized and refractory to conventional chemo-/radio-therapy (Motzer and Bukowski, *J Clin Oncol.* 2006; 24:5601-5608). Current first-line therapeutic agents for RCC patients include anti-angiogenic drugs (such as tyrosine kinase inhibitors (TKI) or anti-VEGF antibodies) have yielded high rates of objective clinical response (Escudier et al., *J Clin Oncol.* 2009; 27:4068-4075; Naijar and Rini, *Ther Adv Med Oncol.* 2012; 4:183-194). However, responder patients typically relapse quickly based on the evolution of treatment-refractory disease (Helfrich et al., *J Exp Med.* 2010; 207:491-503). Given such limitations in durable clinical benefits associated with existing treatment options, there remains a great need to develop alternative and/or improved therapies for patients with RCC. In this regard, RCC is considered an immunogenic cancer as patients may exhibit immune-associated spontaneous or therapeutic tumor regression (Finke et al., *Ann NY Acad Sci.* 1988; 532:387-394; Muul et al., *J Immunol.* 1987; 138:989-995; Lokich, *Am J Clin Oncol.* 1997; 20:416-418). Hence, novel therapies capable of improving the magnitude and recruitment of protective immunity into the TME could expand and prolong clinical benefits, and their development remains a mandate.

High-dose cytokine therapy promotes durable complete responses in a minority of treated RCC patients, however, off-target toxicities have limited general use of this approach (Biswas and Eisen, *Nat Rev Clin Oncol.* 2009; 6:478-487), and more specific/focused immunotherapy approaches are warranted. Vaccines targeting cancer cell-associated antigens are safe and immunogenic in the clinical setting, but they have limited curative value (Vjuanovic and Butterfield, *J Cell Biochem.* 2007; 102:301-310). While many factors could limit the effectiveness of current cancer vaccines, major obstacles to success include poor delivery and/or functional stability of vaccine-induced tumor infiltrating lymphocytes (TIL) and phenotypic heterogeneity of tumor cell populations permitting immune evasion in vivo (Ahmed et al., *Curr Cancer Drug Targets.* 2008; 8:447-453, Zhao et al., *J Immunol.* 2012; 188:1782-1788). To circumvent such limitations to treatment success, vaccines promoting specific Tc1 recognition of tumor vascular cell (i.e. pericytes, VEC) populations can be used (see, for example, Komita et al., 2008, *Cancer Res.* 2008; 68:8076-8084).

As disclosed below, pericytes isolated from RCC, but not normal kidney tissue, express the DLK1 antigen in vivo. Using immunofluorescence microscopy and real-time PCR the NOTCH antagonist delta-like kinase-1 (DLK1) was identified as an antigen differentially expressed by blood vessel pericytes in highly-vascularized renal cell carcinoma (RCC) tumors, but not in normal kidney tissue. DLK1 peptide- and gene-based vaccines applied to mice bearing established RCC tumors provided therapeutic benefits in association with tumor blood vessel normalization (based on decreased vascular permeability and intratumoral hypoxia) and the activation and recruitment of CD8$^+$ T cells into the tumor microenvironment (TME). Post DLK1-based vaccination, the TME was characterized by increased expression of VCAM1$^+$ CD31$^+$ vascular endothelial cells and the CXCL10 (IP-10) chemokine associated with superior recruitment of Type-1 (IFN-γ producing) proinflammatory T effector cells and a dramatic reduction in Jarid1B$^+$, CD133$^+$ and CD44$^+$ stem cell populations.

DLK1 peptide- or gene-based vaccines are both immunogenic and therapeutic in the RENCA model of RCC. Effectively treated RCC tumors displayed vascular normalization based on reduced vascular leak and tissue hypoxia, and were highly-infiltrated by CD8$^+$ TIL in the perivascular space. Residual pericytes in the TME were tightly-approximated to CD31$^+$ VEC and were deficient in expression of DLK1, supportive of vaccine-induced immunoselection of mature mural cell populations in vivo. The results support that vaccines targeting tumor-associated vascular antigens can be used for RCC therapy, and for the treatment of other vascularized solid cancers. Vaccines promoting immune targeting of tumor-associated vascular cells are a therapeutic modality permitting durable normalization of blood vessels in solid cancers, including RCC Material and Methods Mice.

Female 6-8 week old BALB/c mice were purchased from The Jackson Laboratory (Bar Harbor, Me.) and maintained in a pathogen-free animal facility.

Tumor Cells.

The mouse renal cell carcinoma cell line RENCA was purchased from the American Type Culture Collection (ATCC, Manassas, Va.) and cultured in complete media as previously reported (Komita et al. *Cancer Res.* 2008; 68:8076-8084). The cell line was negative for known mouse pathogens, including mycoplasma.

Stromal Cell Isolation.

Human RCC tumor and adjacent (patient-matched) normal kidney specimens were analyzed. Murine RCC tumors and tumor uninvolved kidneys were harvested surgically after euthanasia, 21 days after s.c. injection of 10$^6$ RENCA cells into syngenic BALB/c recipient animals. Human and murine tissues were then minced manually, enzymatically digested, and pericytes and VEC isolated by flow sorting, as previously described (Crisan et al., *Cell Stem Cell.* 2008; 3:301-313). Murine cells were labeled with anti-mouse CD34-FITC (eBioscience, San Diego, Calif.), anti-mouseCD146-PE (BD-Biosciences, San Diego, Calif.), and anti-mouse CD45-APC (BD-Biosciences) prior to sorting into pericyte (CD146$^+$CD34$^{neg}$CD45$^{neg}$) and VEC (CD146$^+$CD34$^+$CD45$^{neg}$) populations using a multi-color fluorescence-activated cell sorter (FACSAria; BD Biosciences). In all cases, cells were >95% pure for the stated phenotype.

Real-Time PCR.

Messenger RNA was isolated from pericytes and VEC using the RNeasy® Plus Micro kit (Qiagen, Valencia, Calif.) according to manufacturer's instructions. cDNA was then generated using High Capacity RNA-to-cDNA kit (Applied Biosystems, Carlsbad, Calif.) according to manufacturer's instructions. Real-time PCR was performed using Fast SYBR® Green Master Mix (Applied Biosystems) with primer pairs for human or mouse HPRT1 (Qiagen), human DLK1 (Applied Biosystems) or mouse DLK1 (forward primer: TGTGACCCCCAGTATGGATT, SEQ ID NO: 63, reverse primer: CCAGGGGCAGTTACACACTT, SEQ ID NO: 64). Reactions were performed in duplicate in a 96-well reaction plate on a StepOnePlus real-time PCR thermocycler (Applied Biosystems). Cycling conditions were 95° C. for 20 min., then 35 cycles of 95° C. for 3 min. and 60° C. for 30 min.

In Vitro Generation of Bone Marrow-Derived Dendritic Cells (DC) and DC.IL12.

DC were generated in 5-day rIL-4+rGM-CSF-supplemented cultures from bone marrow precursors isolated from the tibias/femurs of BALB/c mice infected with recombinant adenovirus encoding mouse IL-12p70 (yielding DC.IL12), as previously described (Zhao et al., *Mol Ther.* 2012; 19:805-814).

Synthetic Peptides.

The H-$2^d$ class I-presented $DLK1_{158-166}$ (CPPGFSGNF; presented by H-$2L^d$), $DLK1_{161-169}$ (GFSGNFCEI; presented by H-$2K^d$), $DLK1_{256-270}$ (TILGVLTSLVVL; containing overlapping $DLK1_{259-267}$ and $DLK1_{262-270}$ sequences presented by H-$2K^d$) peptide were synthesized as previously described (Zhao et al., *J Immunol.* 2012; 188:1782-1788).

Recombinant Lentiviral Vector Production.

Genes encoding mDLK1 and the reverse sequence of mRGSS (as a negative control) were cloned into the pLenti6/V5 D-TOPO vector downstream of the CMV promoter using the Lentiviral Directional TOPO® Expression Kit (Invitrogen, Grand Island, N.Y.). To determine insert presence in the plasmid, expression of the V5 tag was detected by immunofluorescence using an anti-V5 FITC antibody (Invitrogen) and by Western blot using an anti-V5 HRP antibody (Invitrogen). In the initial production of the lentiviruses, 293FT cells (Invitrogen) were transfected with plasmid DNA pLenti-DLK1 (or pLenti-NEG) using VIRAPOWER™ Packaging Mix (Invitrogen) combined with Lipofectamine 2000 (Invitrogen) according to the manufacturer's instructions. After 48 hours, lentivirus was collected and concentrated using a Fast-Trap Virus Purification and Concentration kit (Millipore). Lentiviral (lvDLK1 and lvNEG) titers, reported in transduction units (TU), were determined by quantitating blasticidin (Invitrogen)-resistance in HT-1080 cells according to the manufacturer's instructions. Expanded lentiviral production was performed by the University of Pittsburgh Cancer Institute Lentiviral Vector Core Facility. Lentivirus quality was assessed by infecting HT-1080 cells for 24 h and monitoring cells for coordinate V5 protein expression (Western blot) and cell-surface expression of DLK1 (flow cytometry using an anti-DLK1-PE antibody; Adipogen, San Diego, Calif.).

Animal Therapy Experiments.

BALB/c mice received s.c. injection of $10^6$ RENCA tumor cells (right flank) on day 0. Six days later, the animals were randomized into cohorts of 5 mice with comparable mean tumor sizes. On days 7 and 14 after tumor implantation, mice were treated with 100 µl s.c. injections (left flank) of PBS, $10^6$ DC.IL12 or $10^6$ DC.IL12 that had been pre-pulsed for 2 h at 37° C. with an equimolar (10 µM) mixture of the $DLK1_{158-166}$, $DLK1_{161-169}$ and $DLK1_{259-270}$ peptides. For lentivirus vaccination experiments, randomized BALB/c mice bearing established (day 10; right flank) s.c. RENCA tumors received a single left flank intradermal injection of lvDLK1 or negative control lvNEG at a dose of 40 TU or 200 TU in a total volume of 50 µl PBS. For all animal experiments, tumor size was assessed every 3 to 4 days and recorded in mm², as determined by the product of orthogonal measurements taken using vernier calipers. Data are reported as mean tumor area ±SD.

Evaluation of Specific CD8$^+$ T Cell Responses In Vitro.

Spleens were harvested from 3 mice per group 7 days after the second DC injection. Splenocytes were then stimulated in vitro for 5 days with syngenic DC pulsed with an equimolar (10 µM) mix of the 3 DLK1 peptides applied in the vaccine. Responder CD8$^+$ T cells were then isolated using magnetic bead cell sorting (Miltenyi Biotec) and co-cultured with DC pulsed with individual DLK1 peptides for 72 h, 37° C. and 5% $CO_2$, at which time cell-free supernatants were analyzed for IFN-γ content using a cytokine-specific ELISA (BD-Biosciences).

Fluorescent Imaging of Tumors.

Tumor tissue samples were prepared and sectioned as previously reported (Komita et al., *Cancer Res.* 2008; 68:8076-8084). Six-micron tissue sections were analyzed for expression of CD31 (BD-Biosciences), VCAM1 (R & D Systems, Minneapolis, Minn.), CXCL10 (R & D Systems), NG2 (Millipore, Billerica, Mass.), DLK1 (Santa Cruz), RGS5, Jarid1b (all from Abcam; Cambridge, Mass.), CD133 (BD-Biosciences), CD44 (Abcam) by immunofluorescence microscopy. For analysis of cellular apoptosis, tissue sections were labeled using TUNEL kit (Roche; Indianapolis, Ind.) as per manufacturer's instructions, followed by incubation with secondary anti-streptavidin Cy3 antibody (Jackson Immunoresearch, West Grove, Pa.). Some sections were analyzed by confocal microscopy to generate 30 µm 3-dimensional reconstructions of images. For the vascular permeability imaging, animals received retro-orbital intravenous injections of FITC-labeled tomato lectin (Sigma) and red 20 nm FLUOSPHERES® (Invitrogen), followed by cardiac perfusion of PBS and 4% paraformaldehyde. Tumors were then immediately resected and imaged by confocal microscopy to generate 17 µm 3-dimensional reconstructions.

Hemoglobin Quantitation.

The amount of hemoglobin contained in tissues was quantitated using the Drabkin method (Klungsoyr et al., *Scand J Clin Lab Invest.* 1954; 6:270-276). Hemoglobin content is reported as µg Hb per mg wet weight of tissue.

Measurement of Tumor Hypoxia Using Pimonidazole.

BALB/c mice bearing established (treated or untreated) day 21 s.c. RENCA tumors were injected intraperitoneally (i.p.) with 60 mg/kg pimonidazole hydrochloride (HYPDXYPROBE™; HPI Inc., Burlington, Mass.) 30 min prior to euthanasia and tumor harvest and 6 µm tissue sections prepared and analyzed by immunohistochemistry as previously reported (Komita et al., *Cancer Res.* 2008; 68:8076-8084).

Statistical Analysis.

Comparisons between groups were performed using a two-tailed Student's t test or one-way Analysis of Variance (ANOVA) with Tukey post-hoc analysis, as indicated. All data were analyzed using SigmaStat software, version 3.5 (Systat Software, Chicago, Ill.). Differences between groups with a p-value <0.05 were considered significant.

Results

RCC-Associated Pericytes Differentially Express the DLK1 Antigen.

In the previous analysis of the therapeutic vaccines incorporating peptides derived from each of twelve individual tumor blood vessel-associated antigens, it was noted that vaccines targeting delta-like kinase-1 (DLK1) were most effective in HLA-A2 transgenic recipient mice. To apply DLK1 peptide and gene-based vaccines to the only available transplantable murine model of RCC, RENCA, the pattern of DLK1 expression by cells within the TME was first investigated. RENCA tumors and tumor-uninvolved normal kidneys were removed from syngenic BALB/c mice and processed into single cell suspensions. Pericytes and VEC were then isolated via flow sorting (FIG. 19A) and their extracted mRNA (along with mRNA from the cultured RENCA cell line) analyzed by real-time PCR for DLK1 and housekeeping control, HPRT1, transcript content (FIG. 19B). It was observed that pericytes derived from RCC tumors were uniquely enriched for DLK1 transcripts versus pericytes isolated from the animal-matched, tumor-uninvolved kidneys or VEC or RENCA cells (FIG. 19B). Immunofluorescence microscopy performed on day 21 RENCA tumor sections confirmed that DLK1 protein expression was associated with $NG2^+$ pericytes but not $CD31^+$ VEC in the tumor vasculature in situ (FIG. 19C).

Therapeutic Treatment of RENCA Tumor-Bearing Mice with a DLK1 Peptide-Based Vaccine is Effective and Associated with Specific Tc1 Activation and Recruitment into the TME.

The superior immunogenicity of a vaccine formulation composed of DC.IL12 pulsed with MHC class I-presented peptides to promote T helper-independent priming of specific $CD8^+$ T cells (see above and Zhao et al., *J Immunol.* 2012; 188:1782-1788, Zhao et al., *Mol Ther.* 2012; 19:805-814). Using $H-2^d$ class I-presented peptide epitopes derived from the murine DLK1 protein (i.e. $DLK1_{158-166}$, $DLK1_{161-169}$ and $DLK1_{259-270}$), the impact of treating BALB/c mice bearing established RENCA tumors with a DLK1 peptide-based vaccine was analyzed. As depicted in FIG. 20A, mice treated with the DLK1 peptide-based vaccines, but not the control vaccine (DC.IL12, no peptide) or PBS, exhibited a significant reduction in RENCA tumor growth (FIG. 20A; $p<0.05$ (ANOVA) on days >13). On day 21 (i.e. 7 days after the booster immunization), $CD8^+$ splenocytes were isolated and analyzed for their ability to produce IFN-γ in response to stimulation with specific DLK1 peptides in vitro. A superior level of IFN-γ secretion was observed from $CD8^+$ T cells isolated from mice treated with the DC.IL12+DLK1 peptide vaccines (versus mice treated with DC.IL12 only or PBS) after stimulation with the individual DLK1 peptides (FIG. 20B).

A coordinate fluorescence microscopy analysis if tumor sections revealed that RENCA-bearing mice treated with the DLK1 peptide-based vaccine had fewer $CD31^+$ blood vessels in the TME than control treatment cohorts, and these vessels contained VEC with an activated, VCAMV phenotype (FIG. 20C). RENCA tumors from DC.IL12+DLK1 peptide-treated mice contained abundant locoregional expression of the Tc1-recruiting chemokine CXCL10/IP-10 when compared to control tumors (FIG. 20D).

Vaccination with a Recombinant Lentivirus Encoding Murine DLK1 cDNA is Therapeutic in the RENCA Model.

Clinical trials implementing synthetic peptide-based vaccines are only applicable to subsets of cancer patients given the need to restrict accrual to individuals expressing relevant HLA class I (peptide-presenting) allotypes. The anti-tumor efficacy of a genetic vaccine was evaluated that would allow host antigen-presenting cells to process and present DLK1 peptides in a manner conducive to activate a broad anti-DLK1 ($CD8^+$ and $CD4^+$) T cell repertoire in any individual, regardless of their HLA type. Lentiviral-based vaccines promote prolonged antigen-specific $CD8^+$ T cell responses after a single administration in vivo (He et al. *Immunity.* 2006; 24:643-656). Thus, a recombinant lentivirus encoding full-length murine DLK1 (lvDLK1) and a negative control virus (lvNEG) was engineered.

To assess the therapeutic efficacy of specific genetic vaccination against the DLK1 antigen, RENCA-bearing mice were injected s.c. at a distal site with 40 TU or 200 TU of lvDLK1 or lvNEG in PBS Animals injected with lvDLK1 at either dose exhibited significant reductions in tumor growth compared to animals treated with lvNEG (FIG. 21A). As was the case for the DLK1 peptide-based vaccine, immunofluorescence microscopy analysis of tumor sections supported decreased vascularity and loss of ($DLK1^+$) vascular pericytes (FIG. 21B), and increased presence of $VCAM1^+CD31^+$ VEC and CXCL10 chemokine in the TME of mice treated with lvDLK1 versus lvNEG (FIG. 21C, 21D). Since VCAM1 and CXCL10 play important roles in the extravasation of recruited $VLA-4^+CXCR3^+$ Tc1 from blood into the TME (Bose et al., *Int J Cancer.* 2011; 129:2158-2170), levels of infiltrating $CD8^+$ T cells in RENCA tumors were evaluated. As depicted in FIG. 21E, tumors isolated from mice treated with lvDLK1 contained greater numbers of $CD8^+$ TIL.

Vaccination with a lvDLK1 Normalizes the RENCA Vasculature.

It has been suggested that in the absence of pericytes, the tumor vasculature appears "normalized," with lower densities of blood vessels and reduced vascular permeability in the TME (24), supporting therapeutic strategies designed to selectively reduce or eradicate vascular pericytes within sites of tumor. Given the ability of the lvDLK1-based genetic vaccine to reduce the content of $DLK1^+$ cells in the tumor stroma, further evidence was sought supporting therapeutic vascular "normalization" as a consequence of treatment with the lvDLK1 genetic vaccine. It was initially noted that RENCA tumors harvested from mice treated with lvDLK1 appeared anemic when compared to control tumors (FIG. 22A). This subjective index was confirmed based on analysis of hemoglobin content in tumor lysates (FIG. 22A).

Tumors were analyzed for expression of NG2 (a general pericyte marker in both normal and tumor tissues; Stallcup, *J Neurocytol.* 2002; 31:423-435) using immunofluorescence microscopy, it was observed that animals receiving injections of lvDLK1 displayed tumors with significant reductions in $NG2^+$ pericytes versus tumors from animals vaccinated with lvNEG (FIG. 22B, 22C). Residual tumor pericytes in lvDLK1-treated animals were tightly associated with $CD31^+$ VEC, unlike the randomly-distributed pattern of pericytes detected in the stroma of tumors isolated from control mice (FIG. 22B, 22C). To investigate changes in vascular permeability, animals were labeled with two different dyes, lectin-FITC to bind the vascular endothelium and red 20 nm FLUO-SPHERES® to determine vessel leakiness into tissue. When compared to controls, the tumor blood vessels in mice vaccinated with lvDLK1 displayed a simple tubular architecture devoid of extensive branching (FIG. 22D). Furthermore, while the perivascular stroma of tumors in control treated animals was littered with the red FLUOSPHERES®, these probes were virtually undetected in tumors harvested from lvDLK1 vaccinated mice, consistent with diminished vascular permeability in the TME of these latter animals (FIG. 22D). These data suggest that selective immunization against DLK1 allows for the immunotherapeutic "normalization" of tumor blood vessels in vivo.

Therapeutic Vaccination with lvDLK1 Results in Reduced Hypoxia and a Lower Incidence of Hypoxia-Responsive Cell Populations in the TME.

Hypoxia frequently occurs in solid tumors as a consequence of their "aberrant" blood vessels inefficiently perfusing oxygen into the TME (Matsumoto et al., *Proc Natl Acad Sci USA.* 2009; 106:17898-17903; Jain, *Semin Oncol.* 2002; 29:3-9), resulting in reduced effector T cell (i.e. TIL) function, increased production of immunosuppressive modulators, dysregulated angiogenesis, and an accumulation of cancer stem cells (Wilson and Hay, *Nat Rev Cancer.* 2012; 11:393-410). To investigate changes in hypoxia within tumors after vaccination with lvDK1 versus lvNEG, mice were injected i.p. with pimonidazole, which detects low [<1.3%] $O_2$ tension (Levesque et al., *Stem Cells.* 2007; 25:1954-1965), and performed immunohistochemical analysis. Tumors isolated from mice receiving lvDLK1 vaccines had a very low hypoxic index when compared to tumors culled from control animals (FIG. 23A). Given this large difference in TME hypoxia post-vaccination with lvDLK1, the treatment impact on expression of molecules associated with vascular stromal cells (RGS5) and/or cancer stem cells was investigated (Jarid1B aka histone demethylase lysine demethylase 5b; CD133, CD44), all hypoxia-responsive gene products (Roesch et al., *Cell.* 2010; 141:583-594, Liang et al., *BMC Cancer.* 2012; 12:201, Mathieu et al., *Cancer Res.* 2011; 71:4640-4652). Immuno-fluorescence microscopy analysis of day 27 tumors revealed that all of these markers were reduced in their abundance in the TME after vaccination with lvDLK1 (FIG. 23B-23E).

Therapeutic Vaccination with lvDLK1 Results in Increased Apoptosis of Tumor Cells Distal to Residual Blood Vessels in the Treated TME.

Given the trimming of vascular branches in the RENCA TME and reduction in vascular permeability after vaccination with lvDLK1 (but not lvNEG), it was hypothesized that plasma nutrients required for sustaining tumor cell viability would be limited to regions proximal to the residual, normalized blood vessel network. TUNEL analyses revealed that indeed, the level of cellular apoptosis in the TME of lvDLK1-treated mice was substantially increased when compared with tumors isolated from control treated animals (FIG. 24). Furthermore, virtually all apoptotic events in RENCA tumors isolated from lvDLK1-vaccinated mice were located in tissue regions distal (>60 microns) to residual CD31$^+$ blood vessels (FIG. 24).

Thus, it has been documented that DLK1 is a tumor pericyte-associated antigen that can be immunologically targeted via specific peptide- or gene-based vaccination in vivo, leading to the effective "normalization" of the tumor vasculature and the TME. Effective therapeutic vaccination resulted in the activation of Type-1 (IFN-γ producing) DLK1-specific CD8$^+$ T cells in the periphery (spleen) and the improved recruitment of CD8$^+$ T cells into the TME with a focused localization around residual tumor blood vessels. After treatment with DLK1-based vaccines, the therapeutically-normalized blood vessels in RENCA tumors exhibited a simple conduit design with tightly-approximated (abluminal) DLK1-deficient pericyte populations and activated VCAM1$^+$ VEC that appeared improved in their structural integrity based on reductions in vascular leakiness/permeability. As a consequence, progressively-growing RENCA tumors became normoxic after treatment with DLK1-based vaccines, with regions of the tumor mass that were distal to the residual normalized blood vessel network undergoing apoptotic death. Concomitantly, the CXCL10 chemokine responsible for recruiting Type 1 proinflammatory effector cells was dramatically upregulated only in DLK1-vaccinated mice, which coincided with improved accumulation of CD8$^+$ TIL. These findings support a paradigm in which specific immune effector T cells may serve as regulators of the "angiogenic switch" by monitoring and controlling the status of DLK1$^+$ pericytes within the TME.

Conditional activation of the Wnt/β-catenin/NOTCH signaling pathway leads to vascular normalization (Reis et al. *J Exp Med.* 2012; 209:1611-1627), as indicated by reduced vascular density and improved mural cell attachment, in intracranial murine gliomas. Without being bound by theory, since DLK1 serves as a functional antagonist to NOTCH signaling (Falix et al., *Biochim Biophys Acta.* 2012; 1822: 988-995), its therapeutic removal from the TME as a consequence of DLK1-based vaccination in the present studies would be expected to lead to the de-repression of NOTCH signaling in RENCA tumors. As such, immune-mediated inhibition of DLK1 expression in the TME may represent a protector of NOTCH signaling, thereby maintaining the tumor angiogenic-switch in the "off" position (Leslie et al., *Development.* 2007; 134:839-844, Siekmann and Lawson, *Cell Adh Migr.* 2007; 1:104-106).

The therapeutically "normalized" TME post-vaccination with lvDLK1 was largely devoid of cell populations harboring stem-like phenotypes, regardless of whether such cells represented bona fide cancer stem cells or mesenchymal stem cells or alternate stem cell populations recruited into the TME. Without being bound by theory, the treatment-associated difference in tumor-associated stem cells could reflect the ability of vaccine-induced T cells to: i.) alter the supportive TME thereby limiting the recruitment, accumulation or expansion of such stem cell populations in the TME; ii.) promote the loss of hypoxia in the TME, leading to transcriptional silencing of stem cell markers, many of which have hypoxia-responsive elements (HRE) in their promoter regions (Liang et al., *BMC Cancer.* 2012; 12:201; Mathieu et al., *Cancer Res.* 2011; 71:4640-4652); iii.) promote the corollary cross-priming (Mathieu et al., supra) of specific immune responses against alternate tumor-associated stromal antigens (including stem cell antigens like Jarid1B, CD133 and CD44 among others) leading to specific stem cell regulation/eradication in vivo. Additionally, without being bound by theory, it is possible that stem cells are directly targeted by anti-DLK1 Tc1, since cells expressing DLK1 may also co-express stem cell markers, including CD133, c-kit, and SOX2 (Metsyanim et al., *PLoS One.* 2009; 4:e6709). Cancer stem cells employ many of the same signaling pathways as normal stem cells, including NOTCH (Takebe et al., *Nat Rev Clin Oncol.* 2011; 8:97-106); therefore, it is also feasible that effective silencing of DLK1 leads to a maturation event (and altered phenotypes) in stem cell populations within the TME. These mechanisms are clearly not mutually-exclusive and a combination of these may be involved in the biologic outcomes disclosed herein.

The anti-angiogenic action mediated by the DLK1 vaccine-induced CD8$^+$ T cell repertoire would differ, and likely complement, that of alternative anti-angiogenic treatment modalities such as anti-VEGF antibodies (i.e. bevacizumab) and small molecule tyrosine kinase inhibitors (i.e. sunitinib) (Helfrich et al., *J Exp Med.* 2010; 207:491-503; Rini and Atkins, *Lancet Oncol.* 2009; 10:992-1000; Faivre et al., *Nat Rev Drug Discov.* 2007; 6:734-745). DLK1-based vaccines could represent a logical second-line approach in the many cases of developed resistance to bevacizumab or sunitinib. Pericytes freshly-isolated from human RCC (but not patient-matched normal adjacent kidney tissue) display differential DLK1 expression. DLK1-based vaccines can be used as treatment of patients with vascularized forms of cancer.

Example 4

Clinical Trial

This example provides a clinical trial to study intradermal administration of αDC1s loaded with a mixture of six TBVA-derived peptides at the time of, or a cycle prior to, starting study treatment with the TKI dasatinib. Current therapeutic approaches available for patients with advanced-stage melanoma remain inadequate, and existing approaches including those involving immunotherapy with cytokines and/or targeted strategies have resulted in disappointingly low rates of durable and complete responses. Correcting immune dysfunction in advanced-stage melanoma patients using TKI such as dasatinib is proposed to relicense the patient's immune system to respond optimally to specific immunization. The integration of antigens expressed by tumor-associated blood vessel cells provides a means to selectively target the genetically-/antigenically-heterogeneous population of tumor cells in the advanced-stage melanoma patient.

$CD8^+$ T cell responses are analyzed against the TBVA DLK1, EphA2, HBB, NRP1, RGS5, and TEM1 in peripheral blood of HLA-A2$^+$ melanoma patients prior to, during the course of, and one month after the last dose of dasatinib. Based on the strong Type-1 polarizing potential of αDC1 in vitro, these vaccines enhance Type-1 $CD8^+$ T cell responses against at least 3 of the 6 peptides included in the vaccine (particularly when patients receive concurrent dasatinib administration, as this removes the regulatory action of MDSC/Treg suppressor cells).

A mixture of six TBVA-derived epitopes is evaluated to be applied to αDC1s as an intradermal vaccine injection into 28 HLA-A2$^+$ patients with advanced-stage melanoma. This choice is based on the finding of superior anti-tumor efficacy in HLA-A2 transgenic tumor models for the pooled peptide vaccine approach and the relevance of the TBVA-derived peptides (which share sequence identity in both human and mouse TBVA) in the HLA-A2$^+$ human patient setting. The combinational vaccine+dasatinib modeling suggest that optimal therapeutic benefit against established M05 melanoma occurred when sunitinib administration was initiated at the time of initial vaccination or at the time of boosting.

Systemic review and meta-analysis of previous DC-based vaccine trials in cancer patients suggests that: i.) vaccine-induced T cell responses are associated with beneficial clinical outcome; ii.) mature DC (such as αDC1) were superior activators of specific immunity and a better clinical prognosis when compared to immature DC; iii.) while a threshold dose of DC is required in the vaccine in order to promote specific immunity, a vast increase in DC number over that threshold did not generally yield superior efficacy (Eggert et al., *Cancer Res.* 1999; 59: 3340-3345; Linette et al., *Clin Cancer Res.* 2005; 11: 7692-7699; Verdijk et al., *Clin Cancer Res.* 2009; 15: 2531-2540; Lesterhuis et al., *Clin Cancer Res.* 2011; July 19 [Epub ahead of print]; Castiglione and Piccoli, *J Theor Biol.* 2007; 247: 723-732; Draube et al., *PLoS One.* 2011; 6: e18801). A recent study by Verdijk et al. suggests that intradermal delivery of DC-based vaccines in patients with advanced stage melanoma was clinically equitable to the delivery of these cells directly into lymph nodes (Verdijk et al, op. cit.), while a report from Lesterhuis and colleagues argues that intradermal delivered DC-based vaccines were superior to intranodal delivered vaccines in promoting melanoma-specific T cell activation in vivo (Lesterhuis et al., op cit.). In vivo tracking of intradermal injected DC in melanoma patients suggests that approximately 4% of the administered DC actually migrate to tissue-draining lymph nodes and that the delivery of approximately $5 \times 10^5$ (vaccine) DC are needed to promote clinically-meaningful levels of antigen-specific T cells (Verdijk et al., op. cit.). By extrapolation, these figures indicate that intradermal injection of a vaccine containing approximately $10^7$ mature antigen-loaded αDC1 would be anticipated to provide a quasi-optimal degree of immune stimulation that may be associated with clinical benefit. Preclinical, clinical, and mathematical modeling all suggest that optimal vaccine-induced immunity and benefit to the tumor-bearing host can be best achieved through repeated immunization (3-5 vaccines) provided over a regular-interval schedule. Since there is no consensus in the literature for an optimal time interval between the individual vaccinations, a protocol was adopted involving 4 intradermal vaccines every 2 weeks, which is a commonly employed schedule for DC-based vaccines (Lesterhus et al., op cit.).

A single-center, prospective randomized, pilot, Phase 2 trial is conducted evaluating the activity, safety and immune effects of dasatinib given in combination with an autologous type-1 polarized DC vaccine. Dasatinib is administered at the standard dose and schedule recommended by the FDA (70 mg BID). The autologous type-I DC vaccine is administered either prior to, or concomitant with, the initiation of dasatinib administration. Patients are vaccinated intradermally with the αDC1/peptide mixture on days 1 and 15 of every cycle on an outpatient basis. For those patients starting therapy with vaccine alone, dasatinib is initiated on day 29 after receiving the first immunization. Unless patients are removed from study, they are treated for at least 6 cycles or disease progression. In cases where there is continued clinical benefit and no additional vaccine product is available, patients can continue to be treated on single agent dasatinib.

Leukapheresis

Leukapheresis (90 minutes) is a minimal risk procedure. Prior to the procedure each subject's venous access is evaluated. If a subject does not have acceptable venous access a pheresis catheter is put in place. All selected patients undergo a single 90 minute-long limited leukapheresis once they have been deemed eligible and prior to the first course of vaccination. One time of the subject's blood volume is processed per procedure.

Leukapheresed product is immediately, and a part of it is used for the first vaccination course (Week 1). The remainder of the product is cryopreserved as described. If cytopenia (WBC<2000/mm$^3$ or platelets <40,000/mm$^3$) develops during, or as a result of, leukapheresis, the procedure is postponed until recovery. This will not be considered an adverse event. Samples from each cell product are obtained for hemoglobin, hematocrit, total WBC, and differential and platelet count.

Vaccine

Formulation

Dendritic cells (DC) are derived from autologous (the subject's own) adherent mononuclear cells (monocytes) in the peripheral blood obtained from leukapheresis. In this case, "biologic product" and "biologic substance" are the same.

Storage and Preparation

The final product is placed in vials with labels identifying each unique vaccine lot and cryopreserved. DCs used in the vaccine are suspended in 5% human serum albumin (HSA) and delivered to the clinic for administration. For preparation of the vaccines, the labeled vials of cryopreserved αDC1 are removed from storage in liquid nitrogen and quickly thawed in a 37° C. water bath. After 3 washes in sterile medium, thawed αDC1 are suspended in saline with 5% human serum albumin (HSA), placed in sterile syringes for administration to the subject and delivered to the clinic for administration. Each syringe is labeled with a custom-designed label, identifying the subject and the vaccine. Both saline and HSA are clinical grade.

Administration

The autologous type-I DC vaccine are administered intradermally either prior to, or concomitant with, the initiation of dasatinib administration. The injections are performed on an outpatient basis.

Dendritic cell-based vaccines have been extensively evaluated in thousands of cancer patients over the past 15 years) and found to be safe and extremely well-tolerated.

Study Treatment Plan

No investigational or commercial agents or therapies other than those described below are administered with the intent to treat the patient's malignancy.

Dasatinib Administration

All patients receive dasatinib at a starting dose of 70 mg twice daily by mouth in the outpatient setting. Dasatinib is supplied as 50 mg and 20 mg tablets. Patients take 1 of the 50 mg tablets and 1 of the 20 mg tablets twice daily, approximately every 12 hours, at the same time each day. Dasatinib may be taken with or without food. Patients swallow the tablets whole.

Patients on Arm A start dasatinib administration on cycle 2, day 1 (week 5), while those patients in Arm B start dasatinib administration on cycle 1, day 1 (week 1). Study treatment continues for at least 6 cycles or disease progression. In case of vaccine depletion patients may continue on dasatinib alone and there is evidence of clinical benefit.

The dosing time is adjusted as required for subject convenience. If doses are missed for toxicity, they are not replaced. If a dose is not taken due to an error, it may be taken up to 12 hours later. If vomiting occurs within 30 minutes of intake, that dose is repeated.

| Agent | Premedications/ Precautions | Dose | Route | Schedule | Cycle Length |
|---|---|---|---|---|---|
| αDC1 Vaccine | None | $10^7$ cells | Intradermal injection | Arms A and B: every 2 weeks starting on Cycle 1, day 1 | 28 days (4 weeks) |
| Dasatinib | Take with or without food | 70 mg | Orally, twice a day | Arm A: Daily starting on Cycle 2, day 1 Arm B: daily starting on Cycle 1, day 1 | |

Vaccine Administration

The DC vaccine is administered by a single intradermal injection of approximately $10^7$ cells (a minimum of $5 \times 10^6$ cells is allowable due to manufacturing limitations), with all the DCs being administered on days 1 and 15 of each cycle. The intradermal administration is in the vicinity of the four nodal drainage groups of the four extremities and performed on an outpatient basis. Study treatment will continue for at least 6 cycles or disease progression.

Duration of Study Treatment

In the absence of treatment delays due to adverse events, treatment continues for at least 6 cycles until one of the following criteria applies: Disease progression, Intercurrent illness that prevents further administration of treatment, Unacceptable adverse event(s), Patient decides to withdraw from the study, or General or specific changes in the patient's condition render the patient unacceptable for further treatment in the judgment of the investigator/sub-investigator, Study is terminated, or Loss of ability to freely provide consent Duration of Follow Up Patients are followed for 1 year after removal from study or until death, whichever occurs first.

Study Calendar

Schedules Shown in the Study Calendar Below are Provided as an Example and should be Modified as Appropriate.

Baseline evaluations are conducted within 1 week prior to start of protocol therapy. Scans and x-rays are done ≤4 weeks prior to the start of therapy. In the event that the patient's condition is deteriorating, laboratory evaluations are repeated within 48 hours prior to initiation of the next cycle of therapy.

| | | Week | | | | | | | | Off Study Treatment[f] |
|---|---|---|---|---|---|---|---|---|---|---|
| | Up to -4[d] | 1 | 2 | 3 | 4 | 5 | 6 | 7 | 8 | |
| Informed consent | X | | | | | | | | | |
| HLA-A2 Screening[a] | X | | | | | | | | | |
| BRAF, c-KIT mutation[a] | X | | | | | | | | | |
| Demographics | X | | | | | | | | | |
| Medical history | X | | | | | | | | | |
| Physical exam | X | X | | | | X | | X | | X |
| Vital signs | X | X | | | | X | | X | | X |
| Height | X | | | | | | | | | |
| Weight | X | X | | | | X | | X | | X |
| Performance status | X | X | | | | X | | X | | X |
| CBC w/diff, platelets | X | X | X | X | X | X | X | X | X | X |
| Serum chemistry[b] | X | X | X | X | X | X | X | X | X | X |
| B-HCG[c] | X | | | | | | | | | |
| EKG (as indicated) | X | | | | | | | | | |
| Leukapheresis | X | | | | | | | | | |

-continued

|  | Up to −4[d] | Week | | | | | | | | Off Study Treatment[f] |
|---|---|---|---|---|---|---|---|---|---|---|
|  |  | 1 | 2 | 3 | 4 | 5 | 6 | 7 | 8 | |
| Dasatinib | | | | | | | | | | |
| Arm A |  |  |  |  |  | X | X | X | X | |
| Arm B |  | X | X | X | X | X | X | X | X | |
| DC Vaccine |  | X |  | X |  | X |  | X |  | |
| Immune monitoring-PBMC | X |  | X |  | X |  | X |  | X | X |
| Tumor Biopsy | X |  |  |  |  | X |  |  |  | |
| AE evaluation |  |  |  |  | ←X→ |  |  |  |  | X |
| Tumor measurements | X | Tumor measurements are repeated every 8 weeks. Documentation (radiologic) must be provided for patients removed from study for progressive disease. | | | | | | | | X |
| Radiologic evaluation | X | Radiologic measurements should be performed every 8 weeks. | | | | | | | | X[g] |

[a]Not necessary if already known;
[b]Albumin, alkaline phosphatase, total bilirubin, bicarbonate, BUN, calcium, chloride, creatinine, glucose, LDH, phosphorus, potassium, total protein, SGOT [AST], SGPT [ALT], sodium, magnesium;
[c]Serum pregnancy test (women of childbearing potential);
[d]Screening is to be performed in the UPCI-CTRC;
e: Treatment with DC vaccine and dasatinib will continue for at least 6 cycles (or until disease progression), the weeks of those cycles will follow the tests and procedures listed for weeks 5 through 8 above for each subsequent cycle;
[f]Four weeks after the last dasatinib administration;
[g]If removed from the study for reasons other than DP.

Dose-Limiting Toxicities
Definition of Dose-Limiting Toxicity
  Toxicities are scored according to the NCI Common Terminology Criteria for Adverse Events (NCI CTCAE) v4.0.
  Dose-limiting toxicity (DLT) is defined as the following study drug-related events experienced during Cycle 1:
    Grade 4 neutropenia or thrombocytopenia which lasts more than 7 days;
    Grade 3 or 4 febrile neutropenia; or
    Grade 3 or greater non-hematological toxicities; this includes grade 3 or greater diarrhea, nausea or vomiting which last more than 7 days despite adequate treatment (with loperamide for diarrhea, 5HT3 antagonists, steroids and dopamine antagonist for NN).
Dasatinib Dosing Delays/Modifications

| Dose Level | Dasatinib Dose |
|---|---|
| 0 | 70 mg BID |
| −1 | 50 mg BID |
| −2 | 100 mg QD |

The study uses the CTCAE (Common Terminology Criteria for Adverse Events) version 4.0 for toxicity and serious adverse event reporting.
Patient Selection
Inclusion Criteria
  Patients are HLA-A2$^+$ and have histologically confirmed melanoma that is metastatic (Stage IV) or unresectable Stage IIIB/C and for which standard curative or palliative measures do not exist or are no longer effective.
  Patients have measurable disease by RECIST 1.1, defined as at least one lesion that can be accurately measured in at least one dimension (longest diameter to be recorded for non-nodal lesions and short axis for nodal lesions) as ≥20 mm with conventional techniques or as ≥10 mm with spiral CT scan, MRI, or calipers by clinical exam.
  Patients have at least 2 subcutaneous, intracutaneous, and accessible tumor deposits, lymph node or other site available for biopsy purposes.
  Prior chemotherapy, immunotherapy, or targeted therapy is allowed as long as it did not include dasatinib.
  Age ≥18 years. Because no dosing or adverse event data are currently available on the use of dasatinib in patients <18 years of age, children are excluded.
  ECOG performance status ≤2 (Karnofsky ≥60%)
  Life expectancy of greater than 12 weeks.
  Patients have normal organ and marrow function as defined below:
    Leukocytes ≥3,000/μL
    absolute neutrophil count ≥1,500/μL
    absolute lymphocyte count ≥500/μL
    platelets ≥100,000/μL
    total bilirubin within normal institutional limits
    AST(SGOT)/ALT(SGPT)≤2.5× institutional upper limit of normal
    Creatinine ≤2.0× institutional upper limit of normal
  Serum magnesium, potassium and adjusted (or ionized) calcium ≥the institutional lower limit of normal. (Supplementation of electrolytes prior to screening is allowed).
  Sexually active women and men of childbearing potential agree to use an effective method of birth control during the course of the study and for up to 3 months following the last dose of the study drug, in a manner such that risk of pregnancy is minimized Surgical sterilization, intrauterine device or barrier method (e.g. condom and/or diaphragm with spermicidal agents) are acceptable forms of birth control. Women of childbearing potential have a negative pregnancy test (serum) within 7 days prior to treatment. A pregnancy test is not required for registration. Women who have not menstruated for more than 2 years are considered postmenopausal, thus not of childbearing potential.
Exclusion Criteria
  Patients who have had chemotherapy or radiotherapy within 4 weeks (6 weeks for nitrosoureas or mitomycin C) prior to entering the study or those who have not recovered from adverse events due to agents administered more than 4 weeks earlier.
  Patients with documented c-KIT mutations.

Patients who are receiving any other investigational agents.

Patients with known brain metastases should be excluded from this clinical trial because of their poor prognosis and because they often develop progressive neurologic dysfunction that would confound the evaluation of neurologic and other adverse events.

History of allergic reactions attributed to compounds of similar chemical or biologic composition to dasatinib or any of the components of the vaccine being administered as part of this study.

Women who are pregnant or nursing/breastfeeding.

History of significant bleeding disorder unrelated to cancer, including:
 Diagnosed congenital bleeding disorders (e.g., von Willebrand's disease)
 Diagnosed acquired bleeding disorder within one year (e.g., acquired anti-factor VIII antibodies)

Patients currently taking medications that inhibit platelet function (i.e., aspirin, dipyridamole, epoprostenol, eptifibatide, clopidogrel, cilostazol, abciximab, ticlopidine, and any non-steroidal anti-inflammatory drug) because of a potential increased risk of bleeding from dasatinib.

Patients currently taking anticoagulants (warfarin, heparin/low molecular weight heparin [e.g., danaparoid, dalteparin, tinzaparin, enoxaparin]) because of a potential increased risk of bleeding from dasatinib.

Diagnosis of unstable angina or myocardial infarction within 6 months of study entry.

Patients currently taking one or more of the following drugs that are generally accepted to have a risk of causing Torsades de Pointes:
 quinidine, procainamide, disopyramide
 amiodarone, sotalol, ibutilide, dofetilide
 erythromycins, clarithromycin
 chlorpromazine, haloperidol, mesoridazine, thioridazine, pimozide
 cisapride, bepridil, droperidol, methadone, arsenic, chloroquine, domperidone, halofantrine, levomethadyl, pentamidine, sparfloxacin, lidoflazine.

Diagnosed or suspected congenital long QT syndrome.

Prolonged QTc interval on pre-entry electrocardiogram (>450 msec) within 30 days prior to study registration.

Any history of clinically significant ventricular arrhythmias (such as ventricular tachycardia, ventricular fibrillation, or Torsades de pointes)

Uncontrolled intercurrent illness including, but not limited to, ongoing or active infection, symptomatic congestive heart failure, unstable angina pectoris, cardiac arrhythmia, or psychiatric illness/social situations that would limit compliance with study requirements.

HIV-positive patients on combination antiretroviral therapy are ineligible because of the potential for pharmacokinetic interactions with dasatinib. In addition, these patients are at increased risk of lethal infections when treated with marrow-suppressive therapy. Appropriate studies are undertaken in patients receiving combination antiretroviral therapy when indicated.

Research Samples

Patient peripheral blood and tumor biopsies are obtained at various time points prior to, and after, the initiation of therapy. If the patient is determined to express the HLA-A2 antigen on their peripheral blood cells, to express a wild-type phenotype, and they pass all additional inclusion/exclusion criteria, after written consent, they are entered on trial. Those patients determined to express c-KIT mutations are excluded from study, while BRAF mutational status is used to stratify patients during randomization to ensure a balanced proportion of patients with the mutation on both arms.

Biopsy Tissue.

Melanoma biopsies are obtained prior to the first vaccination (baseline) and week 5 (date of the third vaccination). Patients should have at least 2 subcutaneous, intracutaneous, and accessible tumor deposits, lymph node or other site available for biopsy purposes.

Blood Samples

At least 3 weeks prior to study treatment, peripheral blood is obtained for the screening of patient HLA-A2 expression status and for baseline testing. Peripheral blood is obtained every 2 weeks on trial beginning week 2.

Correlative Studies

HLA-A2/TBVA peptide dextramer$^+$ CD8$^+$ T cells (i.e. CD8$^+$ T cells imaged by flow cytometry using a fluorescently-labeled, antigen-specific probe) exhibits higher frequencies in the peripheral blood and a greater propensity to produce IFN-$\gamma$ after the initiation of $\alpha$DC1-based vaccines. Since dasatinib alters the recruiting capacity of the tumor microenvironment based on activation of VCAM-1 expression on the tumor-associated vascular endothelial cells and locoregional production of CXCR3 ligand chemokines, the frequency of TBVA-specific CD8$^+$ T cells selectively declines in the patients peripheral blood if the combined therapy performs as expected. Circulating levels of the CXCR3 ligand CXCL10 (aka IP-10), become elevated under treatment conditions in patients that are more prone to exhibit objective clinical response to effective immunotherapy. As a consequence, levels of serum CXCL10 are analyzed before, during and after combined vaccine+dasatinib therapy to determine correlation with TBVA-specific CD8$^+$ T cells in the blood versus tumor over time post-treatment.

Immune Monitoring Analysis of TBVA-Specific CD8$^+$ T Cell Responses (Primary Endpoint).

Rationale and Hypothesis:

Translation and clinical vaccine trials have demonstrated that DC/peptide-based vaccines effectively activate specific CD8$^+$ T cells in tumor-bearing hosts that may be detected in peripheral blood, and that individuals that exhibit objective clinical response to such vaccine therapies tend to derive from the cohort of patients that display detectable increases in T cell responses post-vaccination (see, for example, Keiholz, *Recent Results Cancer Res.* 2007; 176: 213-218). The effectiveness of DC1/peptide vaccination to elicit protective/therapeutic T cell-mediated immunity in melanoma models in vivo (see above), support the hypothesis that $\alpha$DC1/peptide vaccination of advanced stage melanoma patients results in increased quantities of specific CD8$^+$ T cells in patient peripheral blood and that those individuals in which improved response to many peptides can be observed are those that are more likely to demonstrate clinical benefit.

Method:

Using fluorescently-labeled HLA-A2/peptide dextramer probes and intracellular staining for the Type-1 cytokine IFN-$\gamma$, how the frequency of CD8$^+$ T cells specific for TBVA peptides changes over time post-vaccination and how many of these T cells are Type-1 effector T cells is determined.

Quantitation of CD8$^+$ T cells, Treg, MDSC and Blood Vessels in Melanoma Biopsy Tissue Rationale and Hypothesis:

Without being bond by theory, tumor progression is believed to be linked to the accumulation of suppressor cell populations (both MDSC and Treg) and strong pro-angiogenic signals, as well as, "prevention" of Type-1 T cell recruitment within the tumor microenvironment (see, for example, Wolf et al., *Clin Cancer Res.* 2005; 11: 8326-8331).

The data in murine melanoma models support the ability of dasatinib (particularly when combined with DC1/peptide vaccines) to counteract these biologic endpoints in vivo. These changes may also be evidenced in effectively treated melanoma patients by analyzing melanoma biopsies taken post- versus pre-treatment and that the greatest "normalization" of the tumor microenvironment is observed after treatment with combined dasatinib+vaccine therapy.

Method:

Immunofluorescence microscopy is used to analyze tumor sections of melanoma biopsies for expression of the markers CD8α (T effector cells), CD11b+CD33+lack of HLA-DR (lineage-negative MDSC), CD11b+CD15+lack of CD14 (neutrophilic MDSC), CD11b+CD14+lack of CD15 (myeloid MDSC), CD4+Foxp3 (Treg cells) and CD31+NG2 (blood vessels). After staining and washing, sections are covered in Gelvatol (Monsanto, St. Louis, Mo.) and a coverslip applied. Positively-stained cells are quantitated by analyzing the images at a final magnification of ×20 using Metamorph Imaging software (Molecular Devices, Sunnyvale, Calif.).

Treg Analysis in PBMC

Rationale and Hypothesis:

Cancer patients have commonly also been shown to have elevated populational frequencies of Treg (based on the $CD4^+$ $Foxp3^+$ phenotype) circulating in theor peripheral blood. Alternate TKI, such as sunitinib, have been shown capable of reducing peripheral blood Treg levels within the first 4 week cycle of drug administration, in concert with a rebound in Type-1 T cell numbers and function in PBMC (Finke et al., *Clin Cancer Res.* 2008; 14: 6674-6682). Dasatinib provides a similar effect in melanoma patients and that those patients exhibiting the greatest degree of Treg reduction post-therapy respond favorably against the peptide epitopes contained in the vaccine formulation.

Method:

Peripheral blood cells are analyzed by flow cytometry using specifc antibodies against CD3 (all T cells), CD4+Foxp3 (Treg), $CD4+CD25^{hi}$(Treg) Results are expressed as percentage of $CD25^{+hi}/Foxp3^+$ cells out of total $CD3^+/CD4^+$ viable cells.

MDSC Analysis in PBMC

Rationale and Hypothesis:

Similar to Treg, levels of cells expressing an MDSC phenotype have been reported to be elevated in the peripheral blood of cancer patients, including patients with advanced-stage melanoma (see, for example, Ko et al., *Clin Cancer Res.* 2009; 15: 2148-2157). TKI, such as sunitinib and dasatinib can reduce the frequency of such suppressor cells to a variable degree when used as a therapy, Melanoma patients treated with dasatinib exhibit reduction in MDSC frequencies in PBMC, with the degree of loss correlating with the patient's ability to respond favorably against the peptide epitopes contained in the vaccine formulation.

Method:

Analysis of MDSC percentages in patient PBMC is performed using flow cytometry and anti-human antibodies against CD11b, CD11c, CD14, CD15, CD33 and HLA-DR.

EphA2 Protein Levels in Tumor Biopsies

Rationale and Hypothesis:

Drug treatments (including dasatinib in vitro) that promote the proteasome-dependent degradation of the tumor (and tumor vascular endothelial) cell-associated protein EphA2 lead to improved recognition by specific $CD8^+$ T cells (see, for example, Kawabe et al., *Cancer Res.* 2009; 69: 6995-7003). Administration of dasatinib to melanoma patients promotes the loss of EphA2 protein within the tumor lesion, leading to an enhancement in the sensitivity of $EphA2^+$ cells in the tumor microenvironment to EphA2-specific $CD8^+$ T cells that have been activated as a consequence of αDC1/peptide-based vaccination.

Method:

Western blotting and immunofluorescence microscopy are used to quantitate EphA2 protein expression in melanoma biopsies pre- versus post-vaccination.

CXCL10 Levels in Patient Serum

Rationale and Hypothesis:

Therapeutic $CD8^+$ T cells require the production of CXCR3 ligand chemokines within the tumor microenvironment in order to effectively home to these disease sites. Two recent clinical trials, including a αDC1/glioma peptide vaccination trial in patients with brain tumors strongly support CXCL10 (aka IP-10) as a chemokine associated with superior clinical outcome to immune-based therapy (see, for example, Schwaab et al., *Clin Cancer Res.* 2009; 15: 4986-4992). This will also be the case in the αDC1/TBVA peptide vaccinated patients with melanoma where Type-1 $CXCR3^+$ responder T cells require a gradient of CXCL10/IP-10 (as detected in serum) in order to traffick to tumor sites in vivo.

Method: Patient serum levels of CXCL10 are monitored using Luminex fluorescent bead technology according to manufacturer's protocol.

Measurement of Effect

Patients with measurable disease are assessed by standard criteria. Patients are re-evaluated every 8 weeks. In addition to a baseline scan, confirmatory scans are obtained ≥4 weeks following initial documentation of an objective response.

Antitumor Effect

Patients are re-evaluated for response every 8 weeks. In addition to a baseline scan, confirmatory scans are obtained no less than 4 weeks following initial documentation of objective response.

Response and progression are evaluated using the new international criteria proposed by the revised Response Evaluation Criteria in Solid Tumors (RECIST) guideline (version 1.1; ref. 104). Changes in the largest diameter (unidimensional measurement) of the tumor lesions and the shortest diameter in the case of malignant lymph nodes are used in the RECIST criteria.

Definitions

Evaluable for toxicity. All patients are evaluable for toxicity from the time of their first treatment.

Evaluable for objective response. Only those patients who have measurable disease present at baseline, have received at least one cycle of therapy, and have had their disease re-evaluated are considered evaluable for response. These patients have their response classified according to the definitions stated below. (Note: Patients who exhibit objective disease progression prior to the end of cycle 1 will also be considered evaluable.)

Evaluable Non-Target Disease Response. Patients who have lesions present at baseline that are evaluable but do not meet the definitions of measurable disease, have received at least one cycle of therapy, and have had their disease re-evaluated are considered evaluable for non-target disease. The response assessment is based on the presence, absence, or unequivocal progression of the lesions.

Disease Parameters

Measurable disease. Measurable lesions are defined as those that can be accurately measured in at least one dimension (longest diameter to be recorded) as ≥20 mm by chest x-ray or as ≥10 mm with CT scan, MRI, or calipers by clinical exam. All tumor measurements must be recorded in millimeters (or decimal fractions of centimeters). Tumor lesions that are situated in a previously irradiated area might or might not be considered measurable.

Malignant lymph nodes. To be considered pathologically enlarged and measurable, a lymph node must be ≥15 mm in short axis when assessed by CT scan (CT scan slice thickness recommended to be no greater than 5 mm) At baseline and in follow-up, only the short axis is measured and followed.

Non-measurable disease. All other lesions (or sites of disease), including small lesions (longest diameter <10 mm or pathological lymph nodes with ≥10 to <15 mm short axis), are considered non-measurable disease. Bone lesions, leptomeningeal disease, ascites, pleural/pericardial effusions, lymphangitis cutis/pulmonitis, inflammatory breast disease, and abdominal masses (not followed by CT or MRI), are considered as non-measurable. Cystic lesions that meet the criteria for radiographically defined simple cysts sare not be considered as malignant lesions (neither measurable nor non-measurable) since they are, by definition, simple cysts. 'Cystic lesions' thought to represent cystic metastases can be considered as measurable lesions, if they meet the definition of measurability described above. However, if non-cystic lesions are present in the same patient, these are preferred for selection as target lesions.

Target lesions. All measurable lesions up to a maximum of 2 lesions per organ and 5 lesions in total, representative of all involved organs, should be identified as target lesions and recorded and measured at baseline. Target lesions are selected on the basis of their size (lesions with the longest diameter), are representative of all involved organs, but in addition lend themselves to reproducible repeated measurements. It may be the case that, on occasion, the largest lesion does not lend itself to reproducible measurement in which circumstance the next largest lesion which can be measured reproducibly is selected. A sum of the diameters (longest for non-nodal lesions, short axis for nodal lesions) for all target lesions is calculated and reported as the baseline sum diameters. If lymph nodes are included in the sum, then only the short axis is added into the sum. The baseline sum diameters are used as reference to further characterize any objective tumor regression in the measurable dimension of the disease.

Non-target lesions. All other lesions (or sites of disease) including any measurable lesions over and above the 5 target lesions are identified as non-target lesions and are recorded at baseline. Measurements of these lesions are not required, but the presence, absence, or in rare cases unequivocal progression of each is noted throughout follow-up.

Methods for Evaluation of Measurable Disease

All measurements are taken and recorded in metric notation using a ruler or calipers. All baseline evaluations are performed as closely as possible to the beginning of treatment and never more than 4 weeks before the beginning of the treatment.

The same method of assessment and the same technique is used to characterize each identified and reported lesion at baseline and during follow-up. Imaging-based evaluation is preferred to evaluation by clinical examination unless the lesion(s) being followed cannot be imaged but are assessable by clinical exam.

Clinical lesions. Clinical lesions are only considered measurable when they are superficial (e.g., skin nodules and palpable lymph nodes) and ≥10 mm diameter as assessed using calipers (e.g., skin nodules). In the case of skin lesions they are documented by color photography, including a ruler to estimate the size of the lesion.

Chest x-ray. Lesions on chest x-ray are measurable lesions when they are clearly defined and surrounded by aerated lung, but CT is preferable.

Conventional CT and MRI. This guideline has defined measurability of lesions on CT scan based on the assumption that CT slice thickness is 5 mm or less. If CT scans have slice thickness greater than 5 mm, the minimum size for a measurable lesion should be twice the slice thickness. MRI is also acceptable in certain situations (e.g. for body scans). MRI has excellent contrast, spatial, and temporal resolution. As with CT, if an MRI is performed, the technical specifications of the scanning sequences used are optimized for the evaluation of the type and site of disease. Furthermore, as with CT, the modality used at follow-up is the same as was used at baseline and the lesions are measured/assessed on the same pulse sequence.

PET-CT. The low dose or attenuation correction CT portion of a combined PET-CT is not always of optimal diagnostic CT quality for use with RECIST measurements. However, if the CT performed as part of a PET-CT is of identical diagnostic quality to a diagnostic CT (with IV and oral contrast), then the CT portion of the PET-CT can be used for RECIST measurements and can be used interchangeably with conventional CT in accurately measuring cancer lesions over time.

Endoscopy, Laparoscopy. Such techniques are used to confirm complete pathological response when biopsies are obtained or to determine relapse in trials where recurrence following complete response (CR) or surgical resection is an endpoint.

Cytology, Histology. These techniques can be used to differentiate between partial responses (PR) and complete responses (CR) in rare cases (e.g., residual lesions in tumor types, such as germ cell tumors, where known residual benign tumors can remain). The cytological confirmation of the neoplastic origin of any effusion that appears or worsens during treatment when the measurable tumor has met criteria for response or stable disease is mandatory to differentiate between response or stable disease (an effusion may be a side effect of the treatment) and progressive disease.

FDG-PET. FDG-PET response assessments can be incorporated to complement CT scanning in assessment of progression (particularly possible 'new' disease). New lesions on the basis of FDG-PET imaging are identified according to the following algorithm:

Negative FDG-PET at baseline, with a positive FDG-PET at follow-up is a sign of PD based on a new lesion.

No FDG-PET at baseline and a positive FDG-PET at follow-up: If the positive FDG-PET at follow-up corresponds to a new site of disease confirmed by CT, this is PD. If the positive FDG-PET at follow-up is not confirmed as a new site of disease on CT, additional follow-up CT scans are needed to determine if there is truly progression occurring at that site (if so, the date of PD is the date of the initial abnormal FDG-PET scan). If the positive FDG-PET at follow-up corresponds to a pre-existing site of disease on CT that is not progressing on the basis of the anatomic images, this is not PD.

FDG-PET may be used to upgrade a response to a CR in a manner similar to a biopsy in cases where a residual radiographic abnormality is thought to represent fibrosis or scarring. The use of FDG-PET in this circumstance should be prospectively described in the protocol and supported by disease-specific medical literature for the indication. However, it must be acknowledged that both approaches may lead to false positive CR due to limitations of FDG-PET and biopsy resolution/sensitivity.

Note: A 'positive' FDG-PET scan lesion means one which is FDG avid with an uptake greater than twice that of the surrounding tissue on the attenuation corrected image.

Response Criteria

Evaluation of Target Lesions

Complete Response (CR): Disappearance of all target lesions. Any pathological lymph nodes (whether target or non-target) must have reduction in short axis to <10 mm.

Partial Response (PR): At least a 30% decrease in the sum of the diameters of target lesions, taking as reference the baseline sum diameters.

Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm (Note: the appearance of one or more new lesions is also considered progressions).

Stable Disease (SD): Neither sufficient shrinkage to qualify for PR nor sufficient increase to qualify for PD, taking as reference the smallest sum diameters while on study.

Evaluation of Non-Target Lesions

Complete Response (CR): Disappearance of all non-target lesions and normalization of tumor marker level. All lymph nodes must be non-pathological in size (<10 mm short axis).

Note: If tumor markers are initially above the upper normal limit, they must normalize for a patient to be considered in complete clinical response.

Non-CR/Non-PD: Persistence of one or more non-target lesion(s) and/or maintenance of tumor marker level above the normal limits.

Progressive Disease (PD): Appearance of one or more new lesions and/or unequivocal progression of existing non-target lesions. Unequivocal progression should not normally trump target lesion status. It must be representative of overall disease status change, not a single lesion increase.

Evaluation of Best Overall Response

The best overall response is the best response recorded from the start of the treatment until disease progression/recurrence (taking as reference for progressive disease the smallest measurements recorded since the treatment started). The patient's best response assignment depends on the achievement of both measurement and confirmation criteria.

For Patients with Measurable Disease (i.e., Target Disease)

| Target Lesions | Non-Target Lesions | New Lesions | Overall Response | Best Overall Response when Confirmation is Required* |
|---|---|---|---|---|
| CR | CR | No | CR | ≥4 wks. Confirmation** |
| CR | Non-CR/Non-PD | No | PR | ≥4 wks. Confirmation** |
| CR | Not evaluated | No | PR | |
| PR | Non-CR/Non-PD/ not evaluated | No | PR | |
| SD | Non-CR/Non-PD/not evaluated | No | SD | Documented at least once ≥4 wks. from baseline** |
| PD | Any | Yes or No | PD | no prior SD, PR or CR |
| Any | PD*** | Yes or No | PD | |
| Any | Any | Yes | PD | |

*See RECIST 1.1 manuscript for further details on what is evidence of a new lesion.
**Only for non-randomized trials with response as primary endpoint.
***In exceptional circumstances, unequivocal progression in non-target lesions may be accepted as disease progression.
Note:
Patients with a global deterioration of health status requiring discontinuation of treatment without objective evidence of disease progression at that time should be reported as "symptomatic deterioration." Every effort should be made to document the objective progression even after discontinuation of treatment.

For Patients with Non-Measurable Disease (i.e., Non-Target Disease)

| Non-Target Lesions | New Lesions | Overall Response |
|---|---|---|
| CR | No | CR |
| Non-CR/non-PD | No | Non-CR/non-PD* |
| Not all evaluated | No | not evaluated |
| Unequivocal PD | Yes or No | PD |
| Any | Yes | PD |

*'Non-CR/non-PD' is preferred over 'stable disease' for non-target disease since SD is increasingly used as an endpoint for assessment of efficacy in some trials so to assign this category when no lesions can be measured is not advised Duration of Response Duration of Overall Response:

The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that progressive disease is objectively documented.

Duration of Stable Disease:

Stable disease is measured from the start of the treatment until the criteria for progression are met, taking as reference the smallest measurements recorded since the treatment started, including the baseline measurements.

Progression-Free Survival

Progression-free survival (PFS) is defined as the duration of time from start of treatment to time of progression or death, whichever occurs first.

Statistical Considerations

Study Design

The effects of combination therapy of dasatinib and vaccine on immune response rate are evaluated. A patient who responded to at least 3 of the 6 peptides is considered to have a positive immune response. The secondary objectives include evaluation of clinical response rate, overall survival (OS), progression free survival (PFS), and immunological endpoints, which include number of $CD8^+$ T cells, MDSC/Treg regulatory cells and blood vessels in tumor lesions, level of EphA2 protein expressed within the tumor lesion and the level of the CXCL10/IP-10 chemokine in patient serum pre- versus post-treatment.

Up to 28 evaluable patients are randomized in 1:1 ratio to receive either:

A. Vaccine alone starting in the first 28-day cycle followed by vaccine combined with daily dasatinib starting on the first day of the second cycle (Arm A)

B. Vaccine combined with daily dasatinib starting on the first day of cycle 1 (Arm B)

Patients not evaluable for immune response are replaced. Randomization is stratified by BRAF mutation status.

Data Analysis

Analysis Sets.

Evaluable Patients are patients who meet all of the protocol inclusion/exclusion criteria and begin treatment with the protocol assigned regimen. All evaluable patients are used in the analysis of safety, immune response, clinical response, OS and PFS.

Baseline Characteristics

Baseline characteristics on all evaluable patients are provided on demographic variables (age, sex, race/ethnicity), performance status, laboratory parameters, prior treatments, and disease characteristics, including tumor size, number of nodes involved, and metastatic sites.

Safety Profile

NCI CTCAE version 4.0 is used to evaluate the serious adverse events (SAEs) in each cycle of the treatment, and for 30 days beyond the last protocol specified treatment. Sever AEs rate for each treatment arm are calculated and the corresponding exact 95% confidence interval (CI) are provided. All adverse events that are determined to be possibly, probably or definitely related to treatment are tabulated according to grade and type (according to the NCI CTCAE, Version 4.0). For each adverse event category, frequencies are tabulated by treatment group according to the highest grade per patient within 30 days after any study treatment.

Efficacy Analysis

The immune response rate, defined as proportion of patients that responded to 3 out of the 6 peptides, for each study arm is calculated with 95% exact CI. The clinical response rate for each study arm is estimated by the percentage of patients achieving CR or PR by RECIST criteria, with corresponding exact 95% CI. Both immune response rate and clinical response rate of the two treatment groups are compared using Fisher exact test. The immune response for the B-raf mutant carrier and non-carrier in is also evaluated.

The Kaplan-Meier estimate of PFS and OS with corresponding 95% confidence band is provided for each dose level. The corresponding median survival time (with 95% confidence limits) is determined, along with OS and PFS estimates at selected time points. The exact log rank test is used to compare the PFS and OS between the two study arms.

The association between the positive immune response and:
a. Objective clinical response.
b. CD8+ T cell infiltration in tumor after cycle 1.
c. Reduction in suppressor cells in the tumor and blood.
d. Reduction in blood vessel density in the tumor after cycle 1.
e. Reduction in EphA2 protein expression in tumor after cycle 1.
f. Increased level of the CXCR3 ligand chemokine CXCL 10/IP-10 in patient serum after cycle 1 is evaluated.

Chi-square (or Fisher exact) test is used to test the association between immune response and the categorical outcomes (e.g. objective clinical response). Wilcoxon test is used to compare the continuous outcomes (e.g. CD8+ T cell infiltration, suppressor cell populations, tumor blood vessel density, EphA2 protein expression, chemokine level) between the immune responders and non-responders.

It will be apparent that the precise details of the methods or compositions described may be varied or modified without departing from the spirit of the described invention. We claim all such modifications and variations fall within the scope and spirit of the claims below.

We claim:

1. A method for eliciting an immune response to a tumor in a subject, comprising administering to a subject a therapeutically effective amount of
   a composition comprising a plurality of polypeptides, wherein each polypeptide in the plurality is at most twelve amino acids in length, wherein the plurality of polypeptides comprises:
   (a) a Protein Delta Homolog 1 (DLK1) polypeptide comprising the amino acid sequence set forth as ILGVLTSLV (SEQ ID NO: 2);
   (b) a Neuropilin 1 (NRP1) polypeptide comprising the amino acid sequence set forth as $GX_4LGMVSGL$ (SEQ ID NO: 7), wherein $X_4$ is a leucine (L) or a methionine (M); and
   (c) a Tumor Endothelial Marker 1 (TEM1) polypeptide comprising the amino acid sequence set forth as $LLVPTCVFX_5V$ (SEQ ID NO: 9), wherein $X_5$ is a leucine (L) or a valine (V),
   thereby eliciting the immune response to the tumor in the subject, wherein the tumor expresses DLK1, NRP1 and TEM1.

2. The method of claim 1, further comprising administering to the subject a therapeutically effective amount of dasatinib, bevacizumab, sunitinib, axitinib, an HSP90 inhibitor, or gemcitabine/fludarabine.

3. The method of claim 1, wherein the immune response decreases growth of the tumor in the subject.

4. The method of claim 1, wherein the immune response decreases vascularization of the tumor.

5. The method of claim 1, wherein the tumor is a colorectal cancer.

6. The method of claim 1, wherein the plurality of polypeptides comprises:
   (a) a Protein Delta Homolog 1 (DLK1) polypeptide comprising the amino acid sequence set forth as ILGVLTSLV (SEQ ID NO: 2);
   (b) a Neuropilin 1 (NRP1) polypeptide comprising the amino acid sequence set forth as $GX_4LGMVSGL$ (SEQ ID NO: 7), wherein $X_4$ is a methionine (M); and
   (c) a Tumor Endothelial Marker 1 (TEM1) polypeptide comprising the amino acid sequence set forth as $LLVPTCVFX_5V$ (SEQ ID NO: 9), wherein $X_5$ is a leucine (L).

7. The method of claim 1, wherein the cancer is a lung cancer.

8. A method for inhibiting the growth of a cancer, the method comprising
   culturing cytotoxic T lymphocytes (CTLs) or CTL precursor cells with a composition and an antigen presenting cell in vitro to produce activated CTLs or CTL matured from the CTL precursors that recognize tumor associated stromal cell antigens, wherein the composition comprises a plurality of polypeptides, wherein each polypeptide in the plurality is at most twelve amino acids in length, wherein the plurality of polypeptides comprises:
   (a) a Protein Delta Homolog 1 (DLK1) polypeptide comprising the amino acid sequence set forth as ILGVLTSLV (SEQ ID NO: 2);
   (b) a Neuropilin 1 (NRP1) polypeptide comprising the amino acid sequence set forth as $GX_4LGMVSGL$ (SEQ ID NO: 7), wherein $X_4$ is a leucine (L) or a methionine (M); and
   (c) a Tumor Endothelial Marker 1 (TEM1) polypeptide comprising the amino acid sequence set forth as $LLVPTCVFX_5V$ (SEQ ID NO: 9), wherein $X_5$ is a leucine (L) or a valine (V); and
   contacting the cancer, with the activated CTLs or CTLs matured from the CTL precursors, wherein the cancer expresses DLK1, NRP1 and TEM1, thereby inhibiting the growth of the cancer.

9. The method of claim 8, wherein the cancer is a colorectal cancer.

10. The method of claim 8, wherein the plurality of polypeptides comprises:
    (a) a Protein Delta Homolog 1 (DLK1) polypeptide comprising the amino acid sequence set forth as ILGVLTSLV (SEQ ID NO: 2);
    (b) a Neuropilin 1 (NRP1) polypeptide comprising the amino acid sequence set forth as $GX_4LGMVSGL$ (SEQ ID NO: 7), wherein $X_4$ is a methionine (M); and
    (c) a Tumor Endothelial Marker 1 (TEM1) polypeptide comprising the amino acid sequence set forth as $LLVPTCVFX_5V$ (SEQ ID NO: 9), wherein $X_5$ is a leucine (L).

11. The method of claim 8, wherein the cancer is lung cancer.

12. A method for eliciting an immune response to a tumor in a subject, comprising administering to a subject a therapeutically effective amount of a composition comprising a plurality of polypeptides, wherein each polypeptide in the plurality is at most twelve amino acids in length, wherein the plurality of polypeptides comprises:
    (a) a Protein Delta Homolog 1 (DLK1) polypeptide comprising the amino acid sequence set forth as ILGVLTSLV (SEQ ID NO: 2);
    (b) a Neuropilin 1 (NRP1) polypeptide comprising the amino acid sequence set forth as $GX_4LGMVSGL$ (SEQ ID NO: 7), wherein $X_4$ is a leucine (L) or a methionine (M); and
    (c) a Tumor Endothelial Marker 1 (TEM1) polypeptide comprising the amino acid sequence set forth as $LLVPTCVFX_5V$ (SEQ ID NO: 9), wherein $X_5$ is a leucine (L) or a valine (V),
    wherein the tumor expresses DLK1, NRP1 and TEM1 and wherein the tumor is a melanoma, thereby eliciting the immune response to the tumor.

13. The method of claim 12, wherein the melanoma is a superficial spreading melanoma, a nodular melanoma, an acral lentiginous melanoma, a lentigo maligna, a clear cell sarcoma, a mucosal melanoma or a uveal melanoma.

14. The method of claim 12, wherein the plurality of polypeptides comprises:
    (a) a Protein Delta Homolog 1 (DLK1) polypeptide comprising the amino acid sequence set forth as ILGVLTSLV (SEQ ID NO: 2);
    (b) a Neuropilin 1 (NRP1) polypeptide comprising the amino acid sequence set forth as $GX_4LGMVSGL$ (SEQ ID NO: 7), wherein $X_4$ is a methionine (M); and
    (c) a Tumor Endothelial Marker 1 (TEM1) polypeptide comprising the amino acid sequence set forth as $LLVPTCVFX_5V$ (SEQ ID NO: 9), wherein $X_5$ is a leucine (L).

15. The method of claim 14, further comprising administering to the subject a therapeutically effective amount of dasatinib.

16. A method for inhibiting the growth of a cancer cell, the method comprising
    culturing cytotoxic T lymphocytes (CTLs) or CTL precursor cells with a composition and an antigen presenting cell in vitro to produce activated CTLs or CTL matured from the CTL precursors that recognize tumor associated stromal cell antigens, wherein the composition comprises a plurality of polypeptides, wherein each polypeptide in the plurality is at most twelve amino acids in length, wherein the plurality of polypeptides comprises:
(a) a Protein Delta Homolog 1 (DLK1) polypeptide comprising the amino acid sequence set forth as ILGVLTSLV (SEQ ID NO: 2);
(b) a Neuropilin 1 (NRP1) polypeptide comprising the amino acid sequence set forth as $GX_4LGMVSGL$ (SEQ ID NO: 7), wherein $X_4$ is a leucine (L) or a methionine (M); and
(c) a Tumor Endothelial Marker 1 (TEM1) polypeptide comprising the amino acid sequence set forth as $LLVPTCVFX_5V$ (SEQ ID NO: 9), wherein $X_5$ is a leucine (L) or a valine (V); and contacting the cancer, with the activated CTLs or CTLs matured from the CTL precursors, thereby inhibiting the growth of the cancer, wherein the cancer expresses DLK1, NRP1 and TEM1 and is a melanoma.

17. The method of claim 16, wherein the melanoma is a superficial spreading melanoma, a nodular melanoma, an acral lentiginous melanoma, a lentigo maligna, a clear cell sarcoma, a mucosal melanoma or a uveal melanoma.

\* \* \* \* \*

SEQUENCE LISTING

```
<160> NUMBER OF SEQ ID NOS: 84

<210> SEQ ID NO 1
<211> LENGTH: 9
<212> TYPE: PRT
<213> ORGANISM: Homo sapiens
<220> FEATURE:
<221> NAME/KEY: Misc_Feature
<222> LOCATION: (9)..(9)
<223> OTHER INFORMATION: X is L or V

<400> SEQUENCE: 1

Arg Leu Thr Pro Gly Val His Glu Xaa
1               5

<210> SEQ ID NO 2
<211> LENGTH: 9
<212> TYPE: PRT
<213> ORGANISM: Homo sapiens

<400> SEQUENCE: 2

Ile Leu Gly Val Leu Thr Ser Leu Val
1               5

<210> SEQ ID NO 3
<211> LENGTH: 9
<212> TYPE: PRT
<213> ORGANISM: Homo sapiens

<400> SEQUENCE: 3
```

Phe Leu Asn Lys Cys Glu Thr Trp Val
1               5

<210> SEQ ID NO 4
<211> LENGTH: 9
<212> TYPE: PRT
<213> ORGANISM: Homo sapiens
<220> FEATURE:
<221> NAME/KEY: Misc_Feature
<222> LOCATION: (9)..(9)
<223> OTHER INFORMATION: X is T or V

<400> SEQUENCE: 4

Arg Leu Leu Val Val Tyr Pro Trp Xaa
1               5

<210> SEQ ID NO 5
<211> LENGTH: 10
<212> TYPE: PRT
<213> ORGANISM: Homo sapiens
<220> FEATURE:
<221> NAME/KEY: Misc_Feature
<222> LOCATION: (9)..(9)
<223> OTHER INFORMATION: X is C or V

<400> SEQUENCE: 5

Arg Leu Leu Gly Asn Val Leu Val Xaa Val
1               5                   10

<210> SEQ ID NO 6
<211> LENGTH: 9
<212> TYPE: PRT
<213> ORGANISM: Homo sapiens

<400> SEQUENCE: 6

Gly Leu Leu Arg Phe Val Thr Ala Val
1               5

<210> SEQ ID NO 7
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: Misc_Feature
<222> LOCATION: (9)..(9)
<223> OTHER INFORMATION: X is L or M

<400> SEQUENCE: 7

Gly Xaa Leu Gly Met Val Ser Gly Leu
1               5

<210> SEQ ID NO 8
<211> LENGTH: 9
<212> TYPE: PRT
<213> ORGANISM: Homo sapiens

<400> SEQUENCE: 8

Val Leu Leu Gly Ala Val Cys Gly Val
1               5

<210> SEQ ID NO 9
<211> LENGTH: 10
<212> TYPE: PRT
<213> ORGANISM: Homo sapiens

```
<220> FEATURE:
<221> NAME/KEY: Misc_Feature
<222> LOCATION: (9)..(9)
<223> OTHER INFORMATION: X is L or V

<400> SEQUENCE: 9

Leu Leu Val Pro Thr Cys Val Phe Xaa Val
1               5                   10

<210> SEQ ID NO 10
<211> LENGTH: 9
<212> TYPE: PRT
<213> ORGANISM: Homo sapiens

<400> SEQUENCE: 10

Thr Leu Ala Asp Phe Asp Pro Arg Val
1               5

<210> SEQ ID NO 11
<211> LENGTH: 9
<212> TYPE: PRT
<213> ORGANISM: Homo sapiens
<220> FEATURE:
<221> NAME/KEY: Misc_Feature
<222> LOCATION: (2)..(2)
<223> OTHER INFORMATION: X is L or A

<400> SEQUENCE: 11

Leu Xaa Ala Leu Pro His Ser Cys Leu
1               5

<210> SEQ ID NO 12
<211> LENGTH: 9
<212> TYPE: PRT
<213> ORGANISM: Homo sapiens
<220> FEATURE:
<221> NAME/KEY: Misc_Feature
<222> LOCATION: (9)..(9)
<223> OTHER INFORMATION: X is L or V

<400> SEQUENCE: 12

Ile Leu Leu Trp Glu Ile Phe Thr Leu
1               5

<210> SEQ ID NO 13
<211> LENGTH: 9
<212> TYPE: PRT
<213> ORGANISM: Homo sapiens
<220> FEATURE:
<221> NAME/KEY: Misc_Feature
<222> LOCATION: (1)..(1)
<223> OTHER INFORMATION: X is I or T

<400> SEQUENCE: 13

Xaa Leu Ser Asn Leu Ser Phe Pro Val
1               5

<210> SEQ ID NO 14
<211> LENGTH: 9
<212> TYPE: PRT
<213> ORGANISM: Homo sapiens

<400> SEQUENCE: 14

Leu Ile Leu Pro Leu Leu Phe Tyr Leu
1               5

<210> SEQ ID NO 15
```

```
<211> LENGTH: 9
<212> TYPE: PRT
<213> ORGANISM: Homo sapiens

<400> SEQUENCE: 15

Asp Ile Trp Asp Gly Ile Pro His Val
1               5

<210> SEQ ID NO 16
<211> LENGTH: 9
<212> TYPE: PRT
<213> ORGANISM: Homo sapiens

<400> SEQUENCE: 16

Tyr Leu Gln Val Asp Leu Arg Phe Leu
1               5

<210> SEQ ID NO 17
<211> LENGTH: 9
<212> TYPE: PRT
<213> ORGANISM: Homo sapiens

<400> SEQUENCE: 17

Asn Met Leu Gly Met Leu Ser Gly Leu
1               5

<210> SEQ ID NO 18
<211> LENGTH: 10
<212> TYPE: PRT
<213> ORGANISM: Homo sapiens

<400> SEQUENCE: 18

Leu Leu Gln Glu Arg Gly Val Ala Tyr Ile
1               5                   10

<210> SEQ ID NO 19
<211> LENGTH: 9
<212> TYPE: PRT
<213> ORGANISM: Homo sapiens

<400> SEQUENCE: 19

Thr Leu Phe Trp Leu Leu Leu Thr Leu
1               5

<210> SEQ ID NO 20
<211> LENGTH: 9
<212> TYPE: PRT
<213> ORGANISM: Homo sapiens

<400> SEQUENCE: 20

Val Ile Ala Met Phe Phe Trp Leu Leu
1               5

<210> SEQ ID NO 21
<211> LENGTH: 383
<212> TYPE: PRT
<213> ORGANISM: Homo sapiens

<400> SEQUENCE: 21

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
                20                  25                  30

Gln Asn Gly Phe Cys Glu Asp Asp Asn Val Cys Arg Cys Gln Pro Gly
```

```
                35                  40                  45

Trp Gln Gly Pro Leu Cys Asp Gln Cys Val Thr Ser Pro Gly Cys Leu
 50                  55                  60

His Gly Leu Cys Gly Glu Pro Gly Gln Cys Ile Cys Thr Asp Gly Trp
 65                  70                  75                  80

Asp Gly Glu Leu Cys Asp Arg Asp Val Arg Ala Cys Ser Ser Ala Pro
                 85                  90                  95

Cys Ala Asn Asn Gly Thr Cys Val Ser Leu Asp Gly Leu Tyr Glu
                100                 105                 110

Cys Ser Cys Ala Pro Gly Tyr Ser Gly Lys Asp Cys Gln Lys Lys Asp
                115                 120                 125

Gly Pro Cys Val Ile Asn Gly Ser Pro Cys Gln His Gly Gly Thr Cys
130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
                180                 185                 190

Arg Cys Arg Cys Pro Ala Gly Phe Ile Asp Lys Thr Cys Ser Arg Pro
                195                 200                 205

Val Thr Asn Cys Ala Ser Ser Pro Cys Gln Asn Gly Gly Thr Cys Leu
210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
                260                 265                 270

His Glu Leu Pro Val Gln Gln Pro Glu His Arg Ile Leu Lys Val Ser
                275                 280                 285

Met Lys Glu Leu Asn Lys Lys Thr Pro Leu Leu Thr Glu Gly Gln Ala
290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Lys Asn Leu Leu Leu Gln
                340                 345                 350

Tyr Asn Ser Gly Glu Asp Leu Ala Val Asn Ile Ile Phe Pro Glu Lys
                355                 360                 365

Ile Asp Met Thr Thr Phe Ser Lys Glu Ala Gly Asp Glu Glu Ile
370                 375                 380

<210> SEQ ID NO 22
<211> LENGTH: 147
<212> TYPE: PRT
<213> ORGANISM: Homo sapiens

<400> SEQUENCE: 22

Met Val His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
                20                  25                  30
```

```
Leu Val Val Tyr Pro Trp Thr Gln Arg Phe Phe Glu Ser Phe Gly Asp
             35                  40                  45

Leu Ser Thr Pro Asp Ala Val Met Gly Asn Pro Lys Val Lys Ala His
 50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
                100                 105                 110

Cys Val Leu Ala His His Phe Gly Lys Glu Phe Thr Pro Pro Val Gln
            115                 120                 125

Ala Ala Tyr Gln Lys Val Val Ala Gly Val Ala Asn Ala Leu Ala His
        130                 135                 140

Lys Tyr His
145

<210> SEQ ID NO 23
<211> LENGTH: 923
<212> TYPE: PRT
<213> ORGANISM: Homo sapiens

<400> SEQUENCE: 23

Met Glu Arg Gly Leu Pro Leu Leu Cys Ala Val Leu Ala Leu Val Leu
  1               5                  10                  15

Ala Pro Ala Gly Ala Phe Arg Asn Asp Lys Cys Gly Asp Thr Ile Lys
                 20                  25                  30

Ile Glu Ser Pro Gly Tyr Leu Thr Ser Pro Gly Tyr Pro His Ser Tyr
             35                  40                  45

His Pro Ser Glu Lys Cys Glu Trp Leu Ile Gln Ala Pro Asp Pro Tyr
         50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Ile Phe Lys Arg Gly
        130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Val Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
        210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255
```

```
Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
            290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670
```

```
Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
            755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
                820                 825                 830

Tyr Glu Gly Glu Gly Glu Gly Asp Lys Asn Ile Ser Arg Lys Pro Gly
            835                 840                 845

Asn Val Leu Lys Thr Leu Asp Pro Ile Leu Ile Thr Ile Ile Ala Met
            850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
                900                 905                 910

Lys Leu Asn Thr Gln Ser Thr Tyr Ser Glu Ala
            915                 920

<210> SEQ ID NO 24
<211> LENGTH: 757
<212> TYPE: PRT
<213> ORGANISM: Homo sapiens

<400> SEQUENCE: 24

Met Leu Leu Arg Leu Leu Leu Ala Trp Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Thr Phe Leu Glu Ala Trp
            35                  40                  45

Arg Ala Cys Arg Glu Leu Gly Gly Asp Leu Ala Thr Pro Arg Thr Pro
50                  55                  60

Glu Glu Ala Gln Arg Val Asp Ser Leu Val Gly Ala Gly Pro Ala Ser
65                  70                  75                  80

Arg Leu Leu Trp Ile Gly Leu Arg Gln Ala Arg Gln Cys Gln Leu
            85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
            115                 120                 125
```

-continued

```
Gln Arg Cys Val Ala Leu Glu Ala Ser Gly Glu His Arg Trp Leu Glu
        130                 135                 140
Gly Ser Cys Thr Leu Ala Val Asp Gly Tyr Leu Cys Gln Phe Gly Phe
145                 150                 155                 160
Glu Gly Ala Cys Pro Ala Leu Gln Asp Glu Ala Gly Gln Ala Gly Pro
                165                 170                 175
Ala Val Tyr Thr Thr Pro Phe His Leu Val Ser Thr Glu Phe Glu Trp
                180                 185                 190
Leu Pro Phe Gly Ser Val Ala Ala Val Gln Cys Gln Ala Gly Arg Gly
            195                 200                 205
Ala Ser Leu Leu Cys Val Lys Gln Pro Glu Gly Gly Val Gly Trp Ser
210                 215                 220
Arg Ala Gly Pro Leu Cys Leu Gly Thr Gly Cys Ser Pro Asp Asn Gly
225                 230                 235                 240
Gly Cys Glu His Glu Cys Val Glu Val Asp Gly His Val Ser Cys
                245                 250                 255
Arg Cys Thr Glu Gly Phe Arg Leu Ala Ala Asp Gly Arg Ser Cys Glu
                260                 265                 270
Asp Pro Cys Ala Gln Ala Pro Cys Glu Gln Gln Cys Glu Pro Gly Gly
                275                 280                 285
Pro Gln Gly Tyr Ser Cys His Cys Arg Leu Gly Phe Arg Pro Ala Glu
            290                 295                 300
Asp Asp Pro His Arg Cys Val Asp Thr Asp Glu Cys Gln Ile Ala Gly
305                 310                 315                 320
Val Cys Gln Gln Met Cys Val Asn Tyr Val Gly Gly Phe Glu Cys Tyr
                325                 330                 335
Cys Ser Glu Gly His Glu Leu Glu Ala Asp Gly Ile Ser Cys Ser Pro
            340                 345                 350
Ala Gly Ala Met Gly Ala Gln Ala Ser Gln Asp Leu Gly Asp Glu Leu
                355                 360                 365
Leu Asp Asp Gly Glu Asp Glu Glu Asp Glu Asp Glu Ala Trp Lys Ala
370                 375                 380
Phe Asn Gly Gly Trp Thr Glu Met Pro Gly Ile Leu Trp Met Glu Pro
385                 390                 395                 400
Thr Gln Pro Pro Asp Phe Ala Leu Ala Tyr Arg Pro Ser Phe Pro Glu
                405                 410                 415
Asp Arg Glu Pro Gln Ile Pro Tyr Pro Glu Pro Thr Trp Pro Pro Pro
                420                 425                 430
Leu Ser Ala Pro Arg Val Pro Tyr His Ser Ser Val Leu Ser Val Thr
            435                 440                 445
Arg Pro Val Val Ser Ala Thr His Pro Thr Leu Pro Ser Ala His
450                 455                 460
Gln Pro Pro Val Ile Pro Ala Thr His Pro Ala Leu Ser Arg Asp His
465                 470                 475                 480
Gln Ile Pro Val Ile Ala Ala Asn Tyr Pro Asp Leu Pro Ser Ala Tyr
                485                 490                 495
Gln Pro Gly Ile Leu Ser Val Ser His Ser Ala Gln Pro Pro Ala His
            500                 505                 510
Gln Pro Pro Met Ile Ser Thr Lys Tyr Pro Glu Leu Phe Pro Ala His
            515                 520                 525
Gln Ser Pro Met Phe Pro Asp Thr Arg Val Ala Gly Thr Gln Thr Thr
            530                 535                 540
```

```
Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
                580                 585                 590

Thr Thr Thr Ser Arg Ser Pro Val Ser Pro Ala His Gln Ile Ser Val
            595                 600                 605

Pro Ala Ala Thr Gln Pro Ala Ala Leu Pro Thr Leu Leu Pro Ser Gln
        610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
                660                 665                 670

Glu Ala Gly Leu Ala Glu His Ser Gln Arg Asp Asp Arg Trp Leu Leu
            675                 680                 685

Val Ala Leu Leu Val Pro Thr Cys Val Phe Leu Val Val Leu Leu Ala
        690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
                740                 745                 750

Cys Arg Thr Ser Val
            755

<210> SEQ ID NO 25
<211> LENGTH: 976
<212> TYPE: PRT
<213> ORGANISM: Homo sapiens

<400> SEQUENCE: 25

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
                20                  25                  30

Asp Phe Ala Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
        50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
                100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
        130                 135                 140

Ile Ala Pro Asp Glu Ile Thr Val Ser Ser Asp Phe Glu Ala Arg His
145                 150                 155                 160
```

-continued

Val Lys Leu Asn Val Glu Glu Arg Ser Val Gly Pro Leu Thr Arg Lys
            165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
            195                 200                 205

Ala His Phe Pro Glu Thr Ile Ala Gly Ser Asp Ala Pro Ser Leu Ala
            210                 215                 220

Thr Val Ala Gly Thr Cys Val Asp His Ala Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
                260                 265                 270

Cys Gln Ala Cys Ser Pro Gly Phe Phe Lys Phe Glu Ala Ser Glu Ser
                275                 280                 285

Pro Cys Leu Glu Cys Pro Glu His Thr Leu Pro Ser Pro Glu Gly Ala
            290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
                340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
            370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
                500                 505                 510

Glu Gly Gln Gly Ala Gly Ser Lys Val His Glu Phe Gln Thr Leu Ser
            515                 520                 525

Pro Glu Gly Ser Gly Asn Leu Ala Val Ile Gly Val Ala Val Gly
            530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

```
Ser Lys Ser Glu Gln Leu Lys Pro Leu Lys Thr Tyr Val Asp Pro His
                580                 585                 590

Thr Tyr Glu Asp Pro Asn Gln Ala Val Leu Lys Phe Thr Thr Glu Ile
            595                 600                 605

His Pro Ser Cys Val Thr Arg Gln Lys Val Ile Gly Ala Gly Glu Phe
        610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 26
<211> LENGTH: 181
<212> TYPE: PRT
```

<213> ORGANISM: Homo sapiens

<400> SEQUENCE: 26

Met Cys Lys Gly Leu Ala Ala Leu Pro His Ser Cys Leu Glu Arg Ala
1               5                   10                  15

Lys Glu Ile Lys Ile Lys Leu Gly Ile Leu Leu Gln Lys Pro Asp Ser
            20                  25                  30

Val Gly Asp Leu Val Ile Pro Tyr Asn Glu Lys Pro Glu Lys Pro Ala
        35                  40                  45

Lys Thr Gln Lys Thr Ser Leu Asp Glu Ala Leu Gln Trp Arg Asp Ser
50                  55                  60

Leu Asp Lys Leu Leu Gln Asn Asn Tyr Gly Leu Ala Ser Phe Lys Ser
65                  70                  75                  80

Phe Leu Lys Ser Glu Phe Ser Glu Glu Asn Leu Glu Phe Trp Ile Ala
                85                  90                  95

Cys Glu Asp Tyr Lys Lys Ile Lys Ser Pro Ala Lys Met Ala Glu Lys
            100                 105                 110

Ala Lys Gln Ile Tyr Glu Glu Phe Ile Gln Thr Glu Ala Pro Lys Glu
        115                 120                 125

Val Asn Ile Asp His Phe Thr Lys Asp Ile Thr Met Lys Asn Leu Val
130                 135                 140

Glu Pro Ser Leu Ser Ser Phe Asp Met Ala Gln Lys Arg Ile His Ala
145                 150                 155                 160

Leu Met Glu Lys Asp Ser Leu Pro Arg Phe Val Arg Ser Glu Phe Tyr
                165                 170                 175

Gln Glu Leu Ile Lys
            180

<210> SEQ ID NO 27
<211> LENGTH: 1106
<212> TYPE: PRT
<213> ORGANISM: Homo sapiens

<400> SEQUENCE: 27

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly Leu
            20                  25                  30

Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln

```
                165                 170                 175
Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
            245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
            325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
            370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
            405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
            485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
            580                 585                 590
```

```
Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser  Pro Leu Asp Thr Ser  Ser Val Leu
        995                 1000                1005
```

```
Tyr Thr Ala Val Gln Pro Asn Glu Gly Asp Asn Asp Tyr Ile Ile
1010                1015                1020

Pro Leu Pro Asp Pro Lys Pro Glu Val Ala Asp Glu Gly Pro Leu
    1025                1030                1035

Glu Gly Ser Pro Ser Leu Ala Ser Ser Thr Leu Asn Glu Val Asn
    1040                1045                1050

Thr Ser Ser Thr Ile Ser Cys Asp Ser Pro Leu Glu Pro Gln Asp
    1055                1060                1065

Glu Pro Glu Pro Glu Pro Gln Leu Glu Leu Gln Val Glu Pro Glu
    1070                1075                1080

Pro Glu Leu Glu Gln Leu Pro Asp Ser Gly Cys Pro Ala Pro Arg
    1085                1090                1095

Ala Glu Ala Glu Asp Ser Phe Leu
    1100                1105

<210> SEQ ID NO 28
<211> LENGTH: 2322
<212> TYPE: PRT
<213> ORGANISM: Homo sapiens

<400> SEQUENCE: 28

Met Gln Ser Gly Arg Gly Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
50                  55                  60

Leu Leu Ala Ala Gly Pro Ala Asp His Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270
```

-continued

```
Leu His Asn Ser Val Pro Val Ala Asp Gly Gln Pro His Glu Val Ser
        275                 280                 285
Val His Ile Asn Ala His Arg Leu Glu Ile Ser Val Asp Gln Tyr Pro
290                 295                 300
Thr His Thr Ser Asn Arg Gly Val Leu Ser Tyr Leu Glu Pro Arg Gly
305                 310                 315                 320
Ser Leu Leu Gly Gly Leu Asp Ala Glu Ala Ser Arg His Leu Gln
                325                 330                 335
Glu His Arg Leu Gly Leu Thr Pro Glu Ala Thr Asn Ala Ser Leu Leu
        340                 345                 350
Gly Cys Met Glu Asp Leu Ser Val Asn Gly Gln Arg Arg Gly Leu Arg
        355                 360                 365
Glu Ala Leu Leu Thr Arg Asn Met Ala Ala Gly Cys Arg Leu Glu Glu
        370                 375                 380
Glu Glu Tyr Glu Asp Asp Ala Tyr Gly His Tyr Glu Ala Phe Ser Thr
385                 390                 395                 400
Leu Ala Pro Glu Ala Trp Pro Ala Met Glu Leu Pro Glu Pro Cys Val
                405                 410                 415
Pro Glu Pro Gly Leu Pro Val Phe Ala Asn Phe Thr Gln Leu Leu
                420                 425                 430
Thr Ile Ser Pro Leu Val Val Ala Glu Gly Gly Thr Ala Trp Leu Glu
        435                 440                 445
Trp Arg His Val Gln Pro Thr Leu Asp Leu Met Glu Ala Glu Leu Arg
        450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
                500                 505                 510
Asp Thr Ser Asp Gln Leu Val Leu Glu Val Ser Val Thr Ala Arg Val
        515                 520                 525
Pro Met Pro Ser Cys Leu Arg Arg Gly Gln Thr Tyr Leu Leu Pro Ile
        530                 535                 540
Gln Val Asn Pro Val Asn Asp Pro Pro His Ile Ile Phe Pro His Gly
545                 550                 555                 560
Ser Leu Met Val Ile Leu Glu His Thr Gln Lys Pro Leu Gly Pro Glu
                565                 570                 575
Val Phe Gln Ala Tyr Asp Pro Asp Ser Ala Cys Glu Gly Leu Thr Phe
                580                 585                 590
Gln Val Leu Gly Thr Ser Ser Gly Leu Pro Val Glu Arg Arg Asp Gln
        595                 600                 605
Pro Gly Glu Pro Ala Thr Glu Phe Ser Cys Arg Glu Leu Glu Ala Gly
        610                 615                 620
Ser Leu Val Tyr Val His Arg Gly Gly Pro Ala Gln Asp Leu Thr Phe
625                 630                 635                 640
Arg Val Ser Asp Gly Leu Gln Ala Ser Pro Ala Thr Leu Lys Val
                645                 650                 655
Val Ala Ile Arg Pro Ala Ile Gln Ile His Arg Ser Thr Gly Leu Arg
                660                 665                 670
Leu Ala Gln Gly Ser Ala Met Pro Ile Leu Pro Ala Asn Leu Ser Val
        675                 680                 685
```

```
Glu Thr Asn Ala Val Gly Gln Asp Val Ser Val Leu Phe Arg Val Thr
    690                 695                 700
Gly Ala Leu Gln Phe Gly Glu Leu Gln Lys Gln Gly Ala Gly Gly Val
705                 710                 715                 720
Glu Gly Ala Glu Trp Trp Ala Thr Gln Ala Phe His Gln Arg Asp Val
                725                 730                 735
Glu Gln Gly Arg Val Arg Tyr Leu Ser Thr Asp Pro Gln His His Ala
            740                 745                 750
Tyr Asp Thr Val Glu Asn Leu Ala Leu Glu Val Gln Val Gly Gln Glu
        755                 760                 765
Ile Leu Ser Asn Leu Ser Phe Pro Val Thr Ile Gln Arg Ala Thr Val
    770                 775                 780
Trp Met Leu Arg Leu Glu Pro Leu His Thr Gln Asn Thr Gln Gln Glu
785                 790                 795                 800
Thr Leu Thr Thr Ala His Leu Glu Ala Thr Leu Glu Glu Ala Gly Pro
                805                 810                 815
Ser Pro Pro Thr Phe His Tyr Glu Val Val Gln Ala Pro Arg Lys Gly
            820                 825                 830
Asn Leu Gln Leu Gln Gly Thr Arg Leu Ser Asp Gly Gln Gly Phe Thr
        835                 840                 845
Gln Asp Asp Ile Gln Ala Gly Arg Val Thr Tyr Gly Ala Thr Ala Arg
    850                 855                 860
Ala Ser Glu Ala Val Glu Asp Thr Phe Arg Phe Arg Val Thr Ala Pro
865                 870                 875                 880
Pro Tyr Phe Ser Pro Leu Tyr Thr Phe Pro Ile His Ile Gly Gly Asp
                885                 890                 895
Pro Asp Ala Pro Val Leu Thr Asn Val Leu Leu Val Val Pro Glu Gly
            900                 905                 910
Gly Glu Gly Val Leu Ser Ala Asp His Leu Phe Val Lys Ser Leu Asn
        915                 920                 925
Ser Ala Ser Tyr Leu Tyr Glu Val Met Glu Arg Pro Arg His Gly Arg
    930                 935                 940
Leu Ala Trp Arg Gly Thr Gln Asp Lys Thr Thr Met Val Thr Ser Phe
945                 950                 955                 960
Thr Asn Glu Asp Leu Leu Arg Gly Arg Leu Val Tyr Gln His Asp Asp
                965                 970                 975
Ser Glu Thr Thr Glu Asp Asp Ile Pro Phe Val Ala Thr Arg Gln Gly
            980                 985                 990
Glu Ser Ser Gly Asp Met Ala Trp Glu Glu Val Arg Gly Val Phe Arg
        995                 1000                1005
Val Ala Ile Gln Pro Val Asn Asp His Ala Pro Val Gln Thr Ile
    1010                1015                1020
Ser Arg Ile Phe His Val Ala Arg Gly Gly Arg Arg Leu Leu Thr
    1025                1030                1035
Thr Asp Asp Val Ala Phe Ser Asp Ala Asp Ser Gly Phe Ala Asp
    1040                1045                1050
Ala Gln Leu Val Leu Thr Arg Lys Asp Leu Leu Phe Gly Ser Ile
    1055                1060                1065
Val Ala Val Asp Glu Pro Thr Arg Pro Ile Tyr Arg Phe Thr Gln
    1070                1075                1080
Glu Asp Leu Arg Lys Arg Arg Val Leu Phe Val His Ser Gly Ala
    1085                1090                1095
Asp Arg Gly Trp Ile Gln Leu Gln Val Ser Asp Gly Gln His Gln
```

-continued

```
                1100                1105                1110
Ala Thr Ala Leu Leu Glu Val Gln Ala Ser Glu Pro Tyr Leu Arg
                1115                1120                1125
Val Ala Asn Gly Ser Ser Leu Val Val Pro Gln Gly Gly Gln Gly
                1130                1135                1140
Thr Ile Asp Thr Ala Val Leu His Leu Asp Thr Asn Leu Asp Ile
                1145                1150                1155
Arg Ser Gly Asp Glu Val His Tyr His Val Thr Ala Gly Pro Arg
                1160                1165                1170
Trp Gly Gln Leu Val Arg Ala Gly Gln Pro Ala Thr Ala Phe Ser
                1175                1180                1185
Gln Gln Asp Leu Leu Asp Gly Ala Val Leu Tyr Ser His Asn Gly
                1190                1195                1200
Ser Leu Ser Pro Arg Asp Thr Met Ala Phe Ser Val Glu Ala Gly
                1205                1210                1215
Pro Val His Thr Asp Ala Thr Leu Gln Val Thr Ile Ala Leu Glu
                1220                1225                1230
Gly Pro Leu Ala Pro Leu Lys Leu Val Arg His Lys Lys Ile Tyr
                1235                1240                1245
Val Phe Gln Gly Glu Ala Ala Glu Ile Arg Arg Asp Gln Leu Glu
                1250                1255                1260
Ala Ala Gln Glu Ala Val Pro Pro Ala Asp Ile Val Phe Ser Val
                1265                1270                1275
Lys Ser Pro Pro Ser Ala Gly Tyr Leu Val Met Val Ser Arg Gly
                1280                1285                1290
Ala Leu Ala Asp Glu Pro Pro Ser Leu Asp Pro Val Gln Ser Phe
                1295                1300                1305
Ser Gln Glu Ala Val Asp Thr Gly Arg Val Leu Tyr Leu His Ser
                1310                1315                1320
Arg Pro Glu Ala Trp Ser Asp Ala Phe Ser Leu Asp Val Ala Ser
                1325                1330                1335
Gly Leu Gly Ala Pro Leu Glu Gly Val Leu Val Glu Leu Glu Val
                1340                1345                1350
Leu Pro Ala Ala Ile Pro Leu Glu Ala Gln Asn Phe Ser Val Pro
                1355                1360                1365
Glu Gly Gly Ser Leu Thr Leu Ala Pro Pro Leu Leu Arg Val Ser
                1370                1375                1380
Gly Pro Tyr Phe Pro Thr Leu Leu Gly Leu Ser Leu Gln Val Leu
                1385                1390                1395
Glu Pro Pro Gln His Gly Ala Leu Gln Lys Glu Asp Gly Pro Gln
                1400                1405                1410
Ala Arg Thr Leu Ser Ala Phe Ser Trp Arg Met Val Glu Glu Gln
                1415                1420                1425
Leu Ile Arg Tyr Val His Asp Gly Ser Glu Thr Leu Thr Asp Ser
                1430                1435                1440
Phe Val Leu Met Ala Asn Ala Ser Glu Met Asp Arg Gln Ser His
                1445                1450                1455
Pro Val Ala Phe Thr Val Thr Val Leu Pro Val Asn Asp Gln Pro
                1460                1465                1470
Pro Ile Leu Thr Thr Asn Thr Gly Leu Gln Met Trp Glu Gly Ala
                1475                1480                1485
Thr Ala Pro Ile Pro Ala Glu Ala Leu Arg Ser Thr Asp Gly Asp
                1490                1495                1500
```

-continued

```
Ser Gly Ser Glu Asp Leu Val Tyr Thr Ile Glu Gln Pro Ser Asn
1505                1510                1515

Gly Arg Val Val Leu Arg Gly Ala Pro Gly Thr Glu Val Arg Ser
    1520                1525                1530

Phe Thr Gln Ala Gln Leu Asp Gly Gly Leu Val Leu Phe Ser His
    1535                1540                1545

Arg Gly Thr Leu Asp Gly Gly Phe Arg Phe Arg Leu Ser Asp Gly
    1550                1555                1560

Glu His Thr Ser Pro Gly His Phe Phe Arg Val Thr Ala Gln Lys
    1565                1570                1575

Gln Val Leu Leu Ser Leu Lys Gly Ser Gln Thr Leu Thr Val Cys
    1580                1585                1590

Pro Gly Ser Val Gln Pro Leu Ser Ser Gln Thr Leu Arg Ala Ser
    1595                1600                1605

Ser Ser Ala Gly Thr Asp Pro Gln Leu Leu Tyr Arg Val Val
    1610                1615                1620

Arg Gly Pro Gln Leu Gly Arg Leu Phe His Ala Gln Gln Asp Ser
    1625                1630                1635

Thr Gly Glu Ala Leu Val Asn Phe Thr Gln Ala Glu Val Tyr Ala
    1640                1645                1650

Gly Asn Ile Leu Tyr Glu His Glu Met Pro Pro Glu Pro Phe Trp
    1655                1660                1665

Glu Ala His Asp Thr Leu Glu Leu Gln Leu Ser Ser Pro Pro Ala
    1670                1675                1680

Arg Asp Val Ala Ala Thr Leu Ala Val Ala Val Ser Phe Glu Ala
    1685                1690                1695

Ala Cys Pro Gln Arg Pro Ser His Leu Trp Lys Asn Lys Gly Leu
    1700                1705                1710

Trp Val Pro Glu Gly Gln Arg Ala Arg Ile Thr Val Ala Ala Leu
    1715                1720                1725

Asp Ala Ser Asn Leu Leu Ala Ser Val Pro Ser Pro Gln Arg Ser
    1730                1735                1740

Glu His Asp Val Leu Phe Gln Val Thr Gln Phe Pro Ser Arg Gly
    1745                1750                1755

Gln Leu Leu Val Ser Glu Glu Pro Leu His Ala Gly Gln Pro His
    1760                1765                1770

Phe Leu Gln Ser Gln Leu Ala Ala Gly Gln Leu Val Tyr Ala His
    1775                1780                1785

Gly Gly Gly Gly Thr Gln Gln Asp Gly Phe His Phe Arg Ala His
    1790                1795                1800

Leu Gln Gly Pro Ala Gly Ala Ser Val Ala Gly Pro Gln Thr Ser
    1805                1810                1815

Glu Ala Phe Ala Ile Thr Val Arg Asp Val Asn Glu Arg Pro Pro
    1820                1825                1830

Gln Pro Gln Ala Ser Val Pro Leu Arg Leu Thr Arg Gly Ser Arg
    1835                1840                1845

Ala Pro Ile Ser Arg Ala Gln Leu Ser Val Val Asp Pro Asp Ser
    1850                1855                1860

Ala Pro Gly Glu Ile Glu Tyr Glu Val Gln Arg Ala Pro His Asn
    1865                1870                1875

Gly Phe Leu Ser Leu Val Gly Gly Gly Leu Gly Pro Val Thr Arg
    1880                1885                1890
```

```
Phe Thr Gln Ala Asp Val Asp Ser Gly Arg Leu Ala Phe Val Ala
1895                1900                1905

Asn Gly Ser Ser Val Ala Gly Ile Phe Gln Leu Ser Met Ser Asp
1910                1915                1920

Gly Ala Ser Pro Pro Leu Pro Met Ser Leu Ala Val Asp Ile Leu
1925                1930                1935

Pro Ser Ala Ile Glu Val Gln Leu Arg Ala Pro Leu Glu Val Pro
1940                1945                1950

Gln Ala Leu Gly Arg Ser Ser Leu Ser Gln Gln Gln Leu Arg Val
1955                1960                1965

Val Ser Asp Arg Glu Glu Pro Glu Ala Ala Tyr Arg Leu Ile Gln
1970                1975                1980

Gly Pro Gln Tyr Gly His Leu Leu Val Gly Gly Arg Pro Thr Ser
1985                1990                1995

Ala Phe Ser Gln Phe Gln Ile Asp Gln Gly Glu Val Val Phe Ala
2000                2005                2010

Phe Thr Asn Phe Ser Ser Ser His Asp His Phe Arg Val Leu Ala
2015                2020                2025

Leu Ala Arg Gly Val Asn Ala Ser Ala Val Val Asn Val Thr Val
2030                2035                2040

Arg Ala Leu Leu His Val Trp Ala Gly Gly Pro Trp Pro Gln Gly
2045                2050                2055

Ala Thr Leu Arg Leu Asp Pro Thr Val Leu Asp Ala Gly Glu Leu
2060                2065                2070

Ala Asn Arg Thr Gly Ser Val Pro Arg Phe Arg Leu Leu Glu Gly
2075                2080                2085

Pro Arg His Gly Arg Val Val Arg Val Pro Arg Ala Arg Thr Glu
2090                2095                2100

Pro Gly Gly Ser Gln Leu Val Glu Gln Phe Thr Gln Gln Asp Leu
2105                2110                2115

Glu Asp Gly Arg Leu Gly Leu Glu Val Gly Arg Pro Glu Gly Arg
2120                2125                2130

Ala Pro Gly Pro Ala Gly Asp Ser Leu Thr Leu Glu Leu Trp Ala
2135                2140                2145

Gln Gly Val Pro Pro Ala Val Ala Ser Leu Asp Phe Ala Thr Glu
2150                2155                2160

Pro Tyr Asn Ala Ala Arg Pro Tyr Ser Val Ala Leu Leu Ser Val
2165                2170                2175

Pro Glu Ala Ala Arg Thr Glu Ala Gly Lys Pro Glu Ser Ser Thr
2180                2185                2190

Pro Thr Gly Glu Pro Gly Pro Met Ala Ser Ser Pro Glu Pro Ala
2195                2200                2205

Val Ala Lys Gly Gly Phe Leu Ser Phe Leu Glu Ala Asn Met Phe
2210                2215                2220

Ser Val Ile Ile Pro Met Cys Leu Val Leu Leu Leu Ala Leu
2225                2230                2235

Ile Leu Pro Leu Leu Phe Tyr Leu Arg Lys Arg Asn Lys Thr Gly
2240                2245                2250

Lys His Asp Val Gln Val Leu Thr Ala Lys Pro Arg Asn Gly Leu
2255                2260                2265

Ala Gly Asp Thr Glu Thr Phe Arg Lys Val Glu Pro Gly Gln Ala
2270                2275                2280

Ile Pro Leu Thr Ala Val Pro Gly Gln Gly Pro Pro Pro Gly Gly
```

```
                2285              2290              2295
Gln Pro Asp Pro Glu Leu Leu Gln Phe Cys Arg Thr Pro Asn Pro
            2300              2305              2310

Ala Leu Lys Asn Gly Gln Tyr Trp Val
            2315              2320

<210> SEQ ID NO 29
<211> LENGTH: 931
<212> TYPE: PRT
<213> ORGANISM: Homo sapiens

<400> SEQUENCE: 29

Met Asp Met Phe Pro Leu Thr Trp Val Phe Leu Ala Leu Tyr Phe Ser
1               5                   10                  15

Arg His Gln Val Arg Gly Gln Pro Asp Pro Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335
```

```
Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Val Phe
            370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
            435                 440                 445

Gln Ile Ser Ala Ser Ser Thr Gln Glu Tyr Leu Trp Ser Pro Ser Ala
            450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Thr Glu Glu Ala Thr
610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
            645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
            675                 680                 685

Leu Gln Ser Asp Ser Gln Arg Glu Gly Gln Tyr Ala Arg Leu Ile Ser
            690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
            725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
```

-continued

```
              755                 760                 765
Gln Ile Val Phe Glu Gly Val Ile Gly Lys Gly Arg Ser Gly Glu Ile
770                 775                 780
Ala Ile Asp Asp Ile Arg Ile Ser Thr Asp Val Pro Leu Glu Asn Cys
785                 790                 795                 800
Met Glu Pro Ile Ser Ala Phe Ala Gly Glu Asn Phe Lys Val Asp Ile
                    805                 810                 815
Pro Glu Ile His Glu Arg Glu Gly Tyr Glu Asp Glu Ile Asp Asp Glu
                820                 825                 830
Tyr Glu Val Asp Trp Ser Asn Ser Ser Ser Ala Thr Ser Gly Ser Gly
            835                 840                 845
Ala Pro Ser Thr Asp Lys Glu Lys Ser Trp Leu Tyr Thr Leu Asp Pro
850                 855                 860
Ile Leu Ile Thr Ile Ile Ala Met Ser Ser Leu Gly Val Leu Leu Gly
865                 870                 875                 880
Ala Thr Cys Ala Gly Leu Leu Leu Tyr Cys Thr Cys Ser Tyr Ser Gly
                    885                 890                 895
Leu Ser Ser Arg Ser Cys Thr Thr Leu Glu Asn Tyr Asn Phe Glu Leu
                900                 905                 910
Tyr Asp Gly Leu Lys His Lys Val Lys Met Asn His Gln Lys Cys Cys
            915                 920                 925
Ser Glu Ala
        930
```

<210> SEQ ID NO 30
<211> LENGTH: 750
<212> TYPE: PRT
<213> ORGANISM: Homo sapiens

<400> SEQUENCE: 30

```
Met Trp Asn Leu Leu His Glu Thr Asp Ser Ala Val Ala Thr Ala Arg
1               5                   10                  15
Arg Pro Arg Trp Leu Cys Ala Gly Ala Leu Val Leu Ala Gly Gly Phe
            20                  25                  30
Phe Leu Leu Gly Phe Leu Phe Gly Trp Phe Ile Lys Ser Ser Asn Glu
        35                  40                  45
Ala Thr Asn Ile Thr Pro Lys His Asn Met Lys Ala Phe Leu Asp Glu
    50                  55                  60
Leu Lys Ala Glu Asn Ile Lys Lys Phe Leu Tyr Asn Phe Thr Gln Ile
65                  70                  75                  80
Pro His Leu Ala Gly Thr Glu Gln Asn Phe Gln Leu Ala Lys Gln Ile
                85                  90                  95
Gln Ser Gln Trp Lys Glu Phe Gly Leu Asp Ser Val Glu Leu Ala His
            100                 105                 110
Tyr Asp Val Leu Leu Ser Tyr Pro Asn Lys Thr His Pro Asn Tyr Ile
        115                 120                 125
Ser Ile Ile Asn Glu Asp Gly Asn Glu Ile Phe Asn Thr Ser Leu Phe
    130                 135                 140
Glu Pro Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
            180                 185                 190
```

```
Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
```

```
             610                 615                 620
Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                    645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
                690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 31
<211> LENGTH: 1338
<212> TYPE: PRT
<213> ORGANISM: Homo sapiens

<400> SEQUENCE: 31

Met Val Ser Tyr Trp Asp Thr Gly Val Leu Leu Cys Ala Leu Leu Ser
1                   5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240
```

```
Lys Leu Leu Arg Gly His Thr Leu Val Leu Asn Cys Thr Ala Thr Thr
            245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
            290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
            325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
            370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
            405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
            485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
            565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
            610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
            645                 650                 655
Asp Gln Glu Ala Pro Tyr Leu Leu Arg Asn Leu Ser Asp His Thr Val
```

```
                660             665             670
Ala Ile Ser Ser Ser Thr Thr Leu Asp Cys His Ala Asn Gly Val Pro
            675             680             685

Glu Pro Gln Ile Thr Trp Phe Lys Asn Asn His Lys Ile Gln Gln Glu
690             695             700

Pro Gly Ile Ile Leu Gly Pro Gly Ser Ser Thr Leu Phe Ile Glu Arg
705             710             715             720

Val Thr Glu Glu Asp Glu Gly Val Tyr His Cys Lys Ala Thr Asn Gln
            725             730             735

Lys Gly Ser Val Glu Ser Ser Ala Tyr Leu Thr Val Gln Gly Thr Ser
            740             745             750

Asp Lys Ser Asn Leu Glu Leu Ile Thr Leu Thr Cys Thr Cys Val Ala
            755             760             765

Ala Thr Leu Phe Trp Leu Leu Leu Thr Leu Phe Ile Arg Lys Met Lys
            770             775             780

Arg Ser Ser Ser Glu Ile Lys Thr Asp Tyr Leu Ser Ile Ile Met Asp
785             790             795             800

Pro Asp Glu Val Pro Leu Asp Glu Gln Cys Glu Arg Leu Pro Tyr Asp
            805             810             815

Ala Ser Lys Trp Glu Phe Ala Arg Glu Arg Leu Lys Leu Gly Lys Ser
            820             825             830

Leu Gly Arg Gly Ala Phe Gly Lys Val Val Gln Ala Ser Ala Phe Gly
            835             840             845

Ile Lys Lys Ser Pro Thr Cys Arg Thr Val Ala Val Lys Met Leu Lys
            850             855             860

Glu Gly Ala Thr Ala Ser Glu Tyr Lys Ala Leu Met Thr Glu Leu Lys
865             870             875             880

Ile Leu Thr His Ile Gly His His Leu Asn Val Val Asn Leu Leu Gly
            885             890             895

Ala Cys Thr Lys Gln Gly Gly Pro Leu Met Val Ile Val Glu Tyr Cys
            900             905             910

Lys Tyr Gly Asn Leu Ser Asn Tyr Leu Lys Ser Lys Arg Asp Leu Phe
            915             920             925

Phe Leu Asn Lys Asp Ala Ala Leu His Met Glu Pro Lys Lys Glu Lys
            930             935             940

Met Glu Pro Gly Leu Glu Gln Gly Lys Lys Pro Arg Leu Asp Ser Val
945             950             955             960

Thr Ser Ser Glu Ser Phe Ala Ser Ser Gly Phe Gln Glu Asp Lys Ser
            965             970             975

Leu Ser Asp Val Glu Glu Glu Glu Asp Ser Asp Gly Phe Tyr Lys Glu
            980             985             990

Pro Ile Thr Met Glu Asp Leu Ile Ser Tyr Ser Phe Gln Val Ala Arg
            995             1000            1005

Gly Met Glu Phe Leu Ser Ser Arg Lys Cys Ile His Arg Asp Leu
            1010            1015            1020

Ala Ala Arg Asn Ile Leu Leu Ser Glu Asn Asn Val Val Lys Ile
            1025            1030            1035

Cys Asp Phe Gly Leu Ala Arg Asp Ile Tyr Lys Asn Pro Asp Tyr
            1040            1045            1050

Val Arg Lys Gly Asp Thr Arg Leu Pro Leu Lys Trp Met Ala Pro
            1055            1060            1065

Glu Ser Ile Phe Asp Lys Ile Tyr Ser Thr Lys Ser Asp Val Trp
            1070            1075            1080
```

```
Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 32
<211> LENGTH: 1356
<212> TYPE: PRT
<213> ORGANISM: Homo sapiens

<400> SEQUENCE: 32

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
```

```
            100                 105                 110
Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
            130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
            210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
                290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Glu Ile Lys Trp Tyr Lys Asn Gly
                355                 360                 365

Ile Pro Leu Glu Ser Asn His Thr Ile Lys Ala Gly His Val Leu Thr
                370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
                450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525
```

-continued

```
Lys Cys Glu Ala Val Asn Lys Val Gly Arg Gly Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu Ile Ile Ile Leu
        755                 760                 765
Val Gly Thr Ala Val Ile Ala Met Phe Phe Trp Leu Leu Leu Val Ile
    770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
            820                 825                 830
Arg Leu Lys Leu Gly Lys Pro Leu Gly Arg Gly Ala Phe Gly Gln Val
        835                 840                 845
Ile Glu Ala Asp Ala Phe Gly Ile Asp Lys Thr Ala Thr Cys Arg Thr
    850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
            900                 905                 910
Met Val Ile Val Glu Phe Cys Lys Phe Gly Asn Leu Ser Thr Tyr Leu
        915                 920                 925
Arg Ser Lys Arg Asn Glu Phe Val Pro Tyr Lys Thr Lys Gly Ala Arg
    930                 935                 940
```

```
Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ala Ser Ser Gly
            965                 970                 975

Phe Val Glu Glu Lys Ser Leu Ser Asp Val Glu Glu Glu Ala Pro
                980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
```

```
           1340           1345           1350
Pro Pro  Val
    1355
```

<210> SEQ ID NO 33
<211> LENGTH: 20
<212> TYPE: DNA
<213> ORGANISM: Homo sapiens

<400> SEQUENCE: 33
agcccaccag agacatggaa                                          20

<210> SEQ ID NO 34
<211> LENGTH: 20
<212> TYPE: DNA
<213> ORGANISM: Homo sapiens

<400> SEQUENCE: 34
ctggctctgt tggaggctgt                                          20

<210> SEQ ID NO 35
<211> LENGTH: 20
<212> TYPE: DNA
<213> ORGANISM: Homo sapiens

<400> SEQUENCE: 35
ctgcacacct gggttctctg                                          20

<210> SEQ ID NO 36
<211> LENGTH: 20
<212> TYPE: DNA
<213> ORGANISM: Homo sapiens

<400> SEQUENCE: 36
gcatgggtta ggggtacagc                                          20

<210> SEQ ID NO 37
<211> LENGTH: 20
<212> TYPE: DNA
<213> ORGANISM: Homo sapiens

<400> SEQUENCE: 37
ggggatgcca acagctataa                                          20

<210> SEQ ID NO 38
<211> LENGTH: 20
<212> TYPE: DNA
<213> ORGANISM: Homo sapiens

<400> SEQUENCE: 38
ctcctgccag taccagaagc                                          20

<210> SEQ ID NO 39
<211> LENGTH: 20
<212> TYPE: DNA
<213> ORGANISM: Homo sapiens

<400> SEQUENCE: 39
catcaatggg agccaggtgt                                          20

<210> SEQ ID NO 40
<211> LENGTH: 20
<212> TYPE: DNA

```
<213> ORGANISM: Homo sapiens

<400> SEQUENCE: 40
tgaaggttga actggcgtga                                               20

<210> SEQ ID NO 41
<211> LENGTH: 22
<212> TYPE: DNA
<213> ORGANISM: Homo sapiens

<400> SEQUENCE: 41
tcagaaacag acatcatggt gc                                            22

<210> SEQ ID NO 42
<211> LENGTH: 22
<212> TYPE: DNA
<213> ORGANISM: Homo sapiens

<400> SEQUENCE: 42
tagacaatag cagaaaaggg gc                                            22

<210> SEQ ID NO 43
<211> LENGTH: 20
<212> TYPE: DNA
<213> ORGANISM: Homo sapiens

<400> SEQUENCE: 43
acagacgcct ttgttctgct                                               20

<210> SEQ ID NO 44
<211> LENGTH: 20
<212> TYPE: DNA
<213> ORGANISM: Homo sapiens

<400> SEQUENCE: 44
tcggaagaaa tgtccaggag                                               20

<210> SEQ ID NO 45
<211> LENGTH: 20
<212> TYPE: DNA
<213> ORGANISM: Homo sapiens

<400> SEQUENCE: 45
tccaagtgga cctgggagat                                               20

<210> SEQ ID NO 46
<211> LENGTH: 20
<212> TYPE: DNA
<213> ORGANISM: Homo sapiens

<400> SEQUENCE: 46
ttcacagccc agtagctcca                                               20

<210> SEQ ID NO 47
<211> LENGTH: 20
<212> TYPE: DNA
<213> ORGANISM: Homo sapiens

<400> SEQUENCE: 47
ccggaagaga cctgtggttg                                               20

<210> SEQ ID NO 48
<211> LENGTH: 20
```

```
<212> TYPE: DNA
<213> ORGANISM: Homo sapiens

<400> SEQUENCE: 48
ccgatcgtcc cttccctatc                                                20

<210> SEQ ID NO 49
<211> LENGTH: 20
<212> TYPE: DNA
<213> ORGANISM: Homo sapiens

<400> SEQUENCE: 49
tgctcctgga gaggcttctg                                                20

<210> SEQ ID NO 50
<211> LENGTH: 22
<212> TYPE: DNA
<213> ORGANISM: Homo sapiens

<400> SEQUENCE: 50
ggaggaagtg ttgacttcat tc                                             22

<210> SEQ ID NO 51
<211> LENGTH: 20
<212> TYPE: DNA
<213> ORGANISM: Homo sapiens

<400> SEQUENCE: 51
cctgcggtga agtcctatcc                                                20

<210> SEQ ID NO 52
<211> LENGTH: 20
<212> TYPE: DNA
<213> ORGANISM: Homo sapiens

<400> SEQUENCE: 52
gtttccagca aagccaggtc                                                20

<210> SEQ ID NO 53
<211> LENGTH: 21
<212> TYPE: DNA
<213> ORGANISM: Homo sapiens

<400> SEQUENCE: 53
aagttgggaa ttctcctcca g                                              21

<210> SEQ ID NO 54
<211> LENGTH: 22
<212> TYPE: DNA
<213> ORGANISM: Homo sapiens

<400> SEQUENCE: 54
ttcctcactg aattcagact tc                                             22

<210> SEQ ID NO 55
<211> LENGTH: 19
<212> TYPE: DNA
<213> ORGANISM: Homo sapiens

<400> SEQUENCE: 55
ttcaccaact gggcccagc                                                 19

<210> SEQ ID NO 56
```

```
<211> LENGTH: 20
<212> TYPE: DNA
<213> ORGANISM: Homo sapiens

<400> SEQUENCE: 56
gttgacacac atctgctggc                                           20

<210> SEQ ID NO 57
<211> LENGTH: 21
<212> TYPE: DNA
<213> ORGANISM: Homo sapiens

<400> SEQUENCE: 57
ccaactacct caagagcaaa c                                         21

<210> SEQ ID NO 58
<211> LENGTH: 20
<212> TYPE: DNA
<213> ORGANISM: Homo sapiens

<400> SEQUENCE: 58
ccaggtcccg atgaatgcac                                           20

<210> SEQ ID NO 59
<211> LENGTH: 19
<212> TYPE: DNA
<213> ORGANISM: Homo sapiens

<400> SEQUENCE: 59
acagacagtg ggatggtcc                                            19

<210> SEQ ID NO 60
<211> LENGTH: 19
<212> TYPE: DNA
<213> ORGANISM: Homo sapiens

<400> SEQUENCE: 60
aaacaggagg tgagcgcag                                            19

<210> SEQ ID NO 61
<211> LENGTH: 19
<212> TYPE: DNA
<213> ORGANISM: Homo sapiens

<400> SEQUENCE: 61
ggcatcgtga tggactccg                                            19

<210> SEQ ID NO 62
<211> LENGTH: 19
<212> TYPE: DNA
<213> ORGANISM: Homo sapiens

<400> SEQUENCE: 62
gctggaaggt ggacagcga                                            19

<210> SEQ ID NO 63
<211> LENGTH: 20
<212> TYPE: DNA
<213> ORGANISM: Homo sapiens

<400> SEQUENCE: 63
tgtgaccccc agtatggatt                                           20
```

-continued

```
<210> SEQ ID NO 64
<211> LENGTH: 20
<212> TYPE: DNA
<213> ORGANISM: Homo sapiens

<400> SEQUENCE: 64
ccaggggcag ttacacactt                                                 20

<210> SEQ ID NO 65
<211> LENGTH: 9
<212> TYPE: PRT
<213> ORGANISM: Homo sapiens

<400> SEQUENCE: 65

Cys Pro Pro Gly Phe Ser Gly Asn Phe
1               5

<210> SEQ ID NO 66
<211> LENGTH: 9
<212> TYPE: PRT
<213> ORGANISM: Homo sapiens

<400> SEQUENCE: 66

Gly Phe Ser Gly Asn Phe Cys Glu Ile
1               5

<210> SEQ ID NO 67
<211> LENGTH: 12
<212> TYPE: PRT
<213> ORGANISM: Homo sapiens

<400> SEQUENCE: 67

Thr Ile Leu Gly Val Leu Thr Ser Leu Val Val Leu
1               5                   10

<210> SEQ ID NO 68
<211> LENGTH: 9
<212> TYPE: PRT
<213> ORGANISM: Homo sapiens

<400> SEQUENCE: 68

Arg Leu Thr Pro Gly Val His Glu Leu
1               5

<210> SEQ ID NO 69
<211> LENGTH: 9
<212> TYPE: PRT
<213> ORGANISM: Homo sapiens

<400> SEQUENCE: 69

Arg Leu Thr Pro Gly Val His Glu Val
1               5

<210> SEQ ID NO 70
<211> LENGTH: 9
<212> TYPE: PRT
<213> ORGANISM: Homo sapiens

<400> SEQUENCE: 70

Arg Leu Leu Val Val Tyr Pro Trp Thr
1               5

<210> SEQ ID NO 71
<211> LENGTH: 9
<212> TYPE: PRT
```

<213> ORGANISM: Homo sapiens

<400> SEQUENCE: 71

Arg Leu Leu Val Val Tyr Pro Trp Val
1               5

<210> SEQ ID NO 72
<211> LENGTH: 10
<212> TYPE: PRT
<213> ORGANISM: Homo sapiens

<400> SEQUENCE: 72

Arg Leu Leu Gly Asn Val Leu Val Cys Val
1               5                   10

<210> SEQ ID NO 73
<211> LENGTH: 10
<212> TYPE: PRT
<213> ORGANISM: Homo sapiens

<400> SEQUENCE: 73

Arg Leu Leu Gly Asn Val Leu Val Val Val
1               5                   10

<210> SEQ ID NO 74
<211> LENGTH: 9
<212> TYPE: PRT
<213> ORGANISM: Homo sapiens

<400> SEQUENCE: 74

Gly Leu Leu Gly Met Val Ser Gly Leu
1               5

<210> SEQ ID NO 75
<211> LENGTH: 9
<212> TYPE: PRT
<213> ORGANISM: Homo sapiens

<400> SEQUENCE: 75

Gly Met Leu Gly Met Val Ser Gly Leu
1               5

<210> SEQ ID NO 76
<211> LENGTH: 10
<212> TYPE: PRT
<213> ORGANISM: Homo sapiens

<400> SEQUENCE: 76

Leu Leu Val Pro Thr Cys Val Phe Leu Val
1               5                   10

<210> SEQ ID NO 77
<211> LENGTH: 10
<212> TYPE: PRT
<213> ORGANISM: Homo sapiens

<400> SEQUENCE: 77

Leu Leu Val Pro Thr Cys Val Phe Val Val
1               5                   10

<210> SEQ ID NO 78
<211> LENGTH: 9
<212> TYPE: PRT
<213> ORGANISM: Homo sapiens

```
<400> SEQUENCE: 78

Leu Leu Ala Leu Pro His Ser Cys Leu
1               5

<210> SEQ ID NO 79
<211> LENGTH: 9
<212> TYPE: PRT
<213> ORGANISM: Homo sapiens

<400> SEQUENCE: 79

Leu Ala Ala Leu Pro His Ser Cys Leu
1               5

<210> SEQ ID NO 80
<211> LENGTH: 9
<212> TYPE: PRT
<213> ORGANISM: Homo sapiens

<400> SEQUENCE: 80

Ile Leu Leu Trp Glu Ile Phe Thr Val
1               5

<210> SEQ ID NO 81
<211> LENGTH: 9
<212> TYPE: PRT
<213> ORGANISM: Homo sapiens

<400> SEQUENCE: 81

Ile Leu Leu Trp Glu Ile Phe Thr Leu
1               5

<210> SEQ ID NO 82
<211> LENGTH: 9
<212> TYPE: PRT
<213> ORGANISM: Homo sapiens

<400> SEQUENCE: 82

Ile Leu Ser Asn Leu Ser Phe Pro Val
1               5

<210> SEQ ID NO 83
<211> LENGTH: 9
<212> TYPE: PRT
<213> ORGANISM: Homo sapiens

<400> SEQUENCE: 83

Thr Leu Ser Asn Leu Ser Phe Pro Val
1               5

<210> SEQ ID NO 84
<211> LENGTH: 5
<212> TYPE: PRT
<213> ORGANISM: Artificial Sequence
<220> FEATURE:
<223> OTHER INFORMATION: Linker

<400> SEQUENCE: 84

Gly Gly Gly Gly Ser
1               5
```